(12) United States Patent
Gerstner

(10) Patent No.: US 11,389,260 B2
(45) Date of Patent: *Jul. 19, 2022

(54) SURGICAL TRAY EFFICIENCY SYSTEM AND RELATED METHODS

(71) Applicant: Flex Operating Room, LLC, Pittsford, NY (US)

(72) Inventor: Jeffrey Gerstner, Pittsford, NY (US)

(73) Assignee: Flex Operating Room, Inc., Pittsford, NY (US)

( * ) Notice: Subject to any disclaimer, the term of this patent is extended or adjusted under 35 U.S.C. 154(b) by 232 days.

This patent is subject to a terminal disclaimer.

(21) Appl. No.: 16/782,699

(22) Filed: Feb. 5, 2020

(65) Prior Publication Data

US 2020/0345442 A1 Nov. 5, 2020

Related U.S. Application Data

(63) Continuation of application No. 16/397,853, filed on Apr. 29, 2019, now Pat. No. 10,575,915, which is a
(Continued)

(51) Int. Cl.
*A61B 50/15* (2016.01)
*A61B 46/10* (2016.01)
(Continued)

(52) U.S. Cl.
CPC .............. *A61B 50/15* (2016.02); *A61B 46/10* (2016.02); *A61B 50/13* (2016.02); *A61B 50/20* (2016.02);
(Continued)

(58) Field of Classification Search
CPC ..................................................... A61B 50/15
See application file for complete search history.

(56) References Cited

U.S. PATENT DOCUMENTS 338,011 A 3/1886 Adams, Jr.
538,145 A 4/1895 Allen
(Continued)

FOREIGN PATENT DOCUMENTS

WO WO 2003081379 10/2003

OTHER PUBLICATIONS

International Search Report and Written Opinion in International Application No. PCT/US2017/025804, dated Jul. 5, 2017, 25 pages.
(Continued)

*Primary Examiner* — Thomas Randazzo
(74) *Attorney, Agent, or Firm* — Fish & Richardson P.C.

(57) ABSTRACT

A surgical tray efficiency system comprising a vertical rack assembly for holding and displaying a plurality of surgical instrument trays, a sterile barrier covering the vertical rack assembly and including tray location identifiers, and a standardization software platform including a customizable interactive planogram is described. The customizable interactive planogram software helps operating room staff arrange the instrument trays on the vertical rack assembly according to a predetermined customizable location ID, and create/load/access information related to the surgical procedure/trays/instruments before, during, and after the surgery.

17 Claims, 41 Drawing Sheets

Related U.S. Application Data continuation of application No. 15/478,219, filed on Apr. 3, 2017, now Pat. No. 10,271,917, which is a continuation-in-part of application No. 15/055,280, filed on Feb. 26, 2016, now Pat. No. 9,895,201.

(60) Provisional application No. 62/317,544, filed on Apr. 2, 2016, provisional application No. 62/121,710, filed on Feb. 27, 2015.

(51) Int. Cl.

| | | |
|---|---|---|
| *A61B 50/33* | (2016.01) | |
| *A61B 90/00* | (2016.01) | |
| *A61B 50/13* | (2016.01) | |
| *A61B 50/22* | (2016.01) | |
| *B25J 9/16* | (2006.01) | |
| *B25J 15/04* | (2006.01) | |
| *F16M 11/42* | (2006.01) | |
| *A61B 50/20* | (2016.01) | |
| *A61B 50/34* | (2016.01) | |
| *F16M 11/22* | (2006.01) | |
| *F16M 13/02* | (2006.01) | |
| *A61B 90/98* | (2016.01) | |
| *A61B 90/94* | (2016.01) | |

(52) U.S. Cl.
CPC .............. *A61B 50/22* (2016.02); *A61B 50/33* (2016.02); *A61B 50/34* (2016.02); *A61B 90/37* (2016.02); *B25J 9/1679* (2013.01); *B25J 15/0491* (2013.01); *F16M 11/22* (2013.01); *F16M 11/42* (2013.01); *F16M 13/027* (2013.01); *A61B 90/94* (2016.02); *A61B 90/98* (2016.02); *A61B 2050/155* (2016.02); *Y10S 901/06* (2013.01)

(56) References Cited

U.S. PATENT DOCUMENTS

| | | |
|---|---|---|
| 725,625 A | 4/1903 | Lurye |
| 907,171 A | 12/1908 | Poles et al. |
| 1,104,004 A | 7/1914 | Rathbone |
| 1,204,286 A | 11/1916 | Lengquist |
| 1,531,540 A | 3/1925 | Calero |
| 1,715,163 A | 5/1929 | Kim |
| 2,002,128 A | 5/1935 | Reidenbaugh |
| 2,148,548 A | 2/1939 | Gregory |
| 2,530,231 A | 11/1950 | Detweiler |
| 2,707,841 A | 5/1955 | Figura |
| 3,294,266 A | 12/1966 | Snow |
| 4,109,892 A | 8/1978 | Hartung |
| 4,113,218 A | 9/1978 | Linder |
| 4,927,214 A | 5/1990 | Kaufman et al. |
| 5,096,072 A | 3/1992 | Link |
| 5,170,804 A | 12/1992 | Glassman |
| 5,289,957 A | 3/1994 | Huang |
| 5,310,066 A | 5/1994 | Konstant |
| 5,454,722 A | 10/1995 | Holland et al. |
| 5,590,796 A | 1/1997 | Herman |
| 5,610,811 A | 3/1997 | Honda |
| 5,927,214 A | 7/1999 | Schwartz et al. |
| 5,991,728 A | 11/1999 | DeBusk et al. |
| 6,019,102 A * | 2/2000 | Becker ................... A61B 50/15 128/849 |
| 6,039,228 A | 3/2000 | Stein |
| 6,105,797 A | 8/2000 | Haisma |
| 6,158,437 A | 12/2000 | Vagley |
| 6,189,459 B1 | 2/2001 | DeAngelis |
| 6,224,072 B1 | 5/2001 | Weck |
| 6,267,345 B1 | 7/2001 | Turner |
| 6,382,434 B1 | 5/2002 | Silberg |
| 6,497,233 B1 * | 12/2002 | DeAngelis ............. A61B 46/10 128/849 |
| 6,823,805 B2 | 11/2004 | Becker |
| 7,249,680 B2 | 7/2007 | Wang |
| 7,624,954 B2 | 12/2009 | Randle, Jr. |
| 7,731,136 B1 | 6/2010 | Chisolm |
| 7,748,802 B2 | 7/2010 | Peruzzi |
| 7,815,202 B2 | 10/2010 | Richards |
| 8,074,815 B2 * | 12/2011 | Gerstner ................ A61B 50/13 108/115 |
| 8,104,787 B2 | 1/2012 | Haley |
| 8,323,034 B1 | 12/2012 | Youngblood |
| 8,371,592 B2 | 2/2013 | Feitel |
| 8,464,994 B2 | 6/2013 | Chiu |
| 8,689,704 B2 * | 4/2014 | Hodges .................. A61B 46/10 312/319.9 |
| 8,763,824 B2 | 7/2014 | Alcock |
| 8,911,677 B2 | 12/2014 | Gerstner et al. |
| 8,950,344 B2 | 2/2015 | Lewis et al. |
| 10,271,917 B2 * | 4/2019 | Gerstner ............. F16M 13/027 |
| 10,575,915 B2 * | 3/2020 | Gerstner ................ A61B 50/15 |
| 2002/0023889 A1 | 2/2002 | Larbaletier |
| 2004/0194673 A1 * | 10/2004 | Comeaux ............... A61B 50/13 108/90 |
| 2005/0229937 A1 * | 10/2005 | Salvaggio ............. A61B 50/13 128/849 |
| 2005/0275178 A1 | 12/2005 | Huesdash |
| 2006/0260515 A1 * | 11/2006 | Hodges .................. A61B 50/13 108/6 |
| 2008/0073304 A1 | 3/2008 | Corbett |
| 2008/0149001 A1 * | 6/2008 | Hodges .................. A61B 50/15 108/6 |
| 2009/0045154 A1 | 2/2009 | Gerstner |
| 2009/0267772 A1 | 10/2009 | Dehnadi |
| 2011/0247634 A1 * | 10/2011 | Young .................... A61B 50/15 128/849 |
| 2012/0042808 A1 * | 2/2012 | Allen ..................... A61B 50/10 108/154 |
| 2012/0137935 A1 * | 6/2012 | Hodges .................. A61B 46/10 108/3 |
| 2012/0248047 A1 | 10/2012 | Tanabe |
| 2013/0328661 A1 | 12/2013 | Phillips et al. |
| 2014/0041669 A1 * | 2/2014 | Houde ................... A61B 50/15 128/849 |
| 2014/0216305 A1 * | 8/2014 | Hodges .................. A61B 50/15 108/3 |
| 2015/0020813 A1 | 1/2015 | Kannan et al. |
| 2016/0249996 A1 * | 9/2016 | Gerstner .................. A47F 5/137 211/130.1 |
| 2017/0202630 A1 | 7/2017 | Gerstner et al. |
| 2019/0254767 A1 | 8/2019 | Gerstner et al. |

OTHER PUBLICATIONS

Office Action in Australian Appln. No. 2017240831, dated Jan. 17, 2022, 3 pages.

AU Office Action in Australian Appln. No. 2017240831, dated Jun. 4, 2021, 2 pages.

* cited by examiner

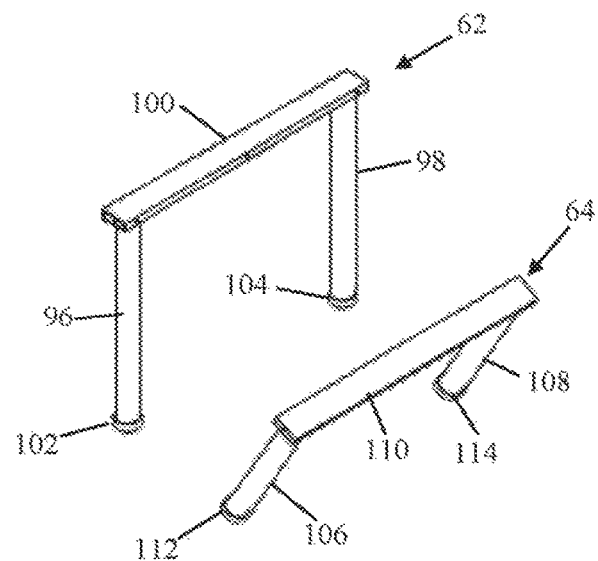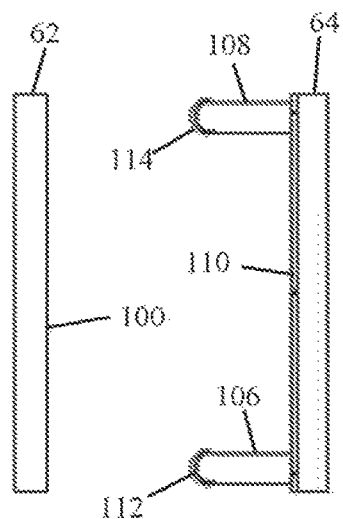
FIG. 12     FIG. 13
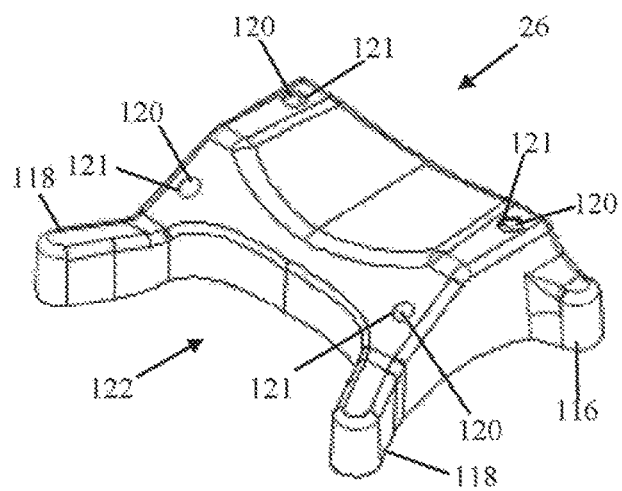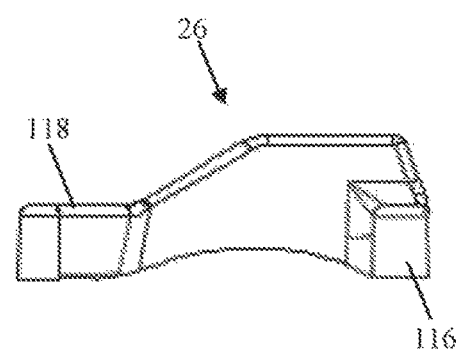
FIG. 14     FIG. 15

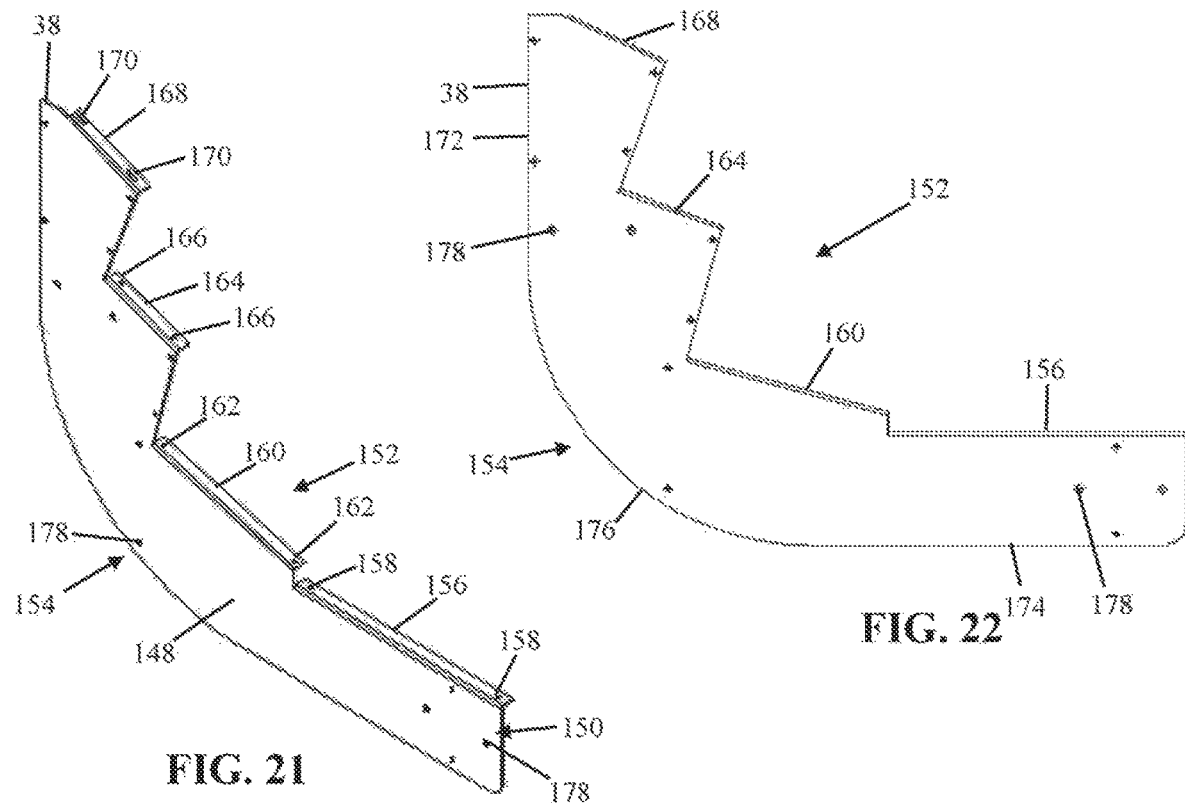
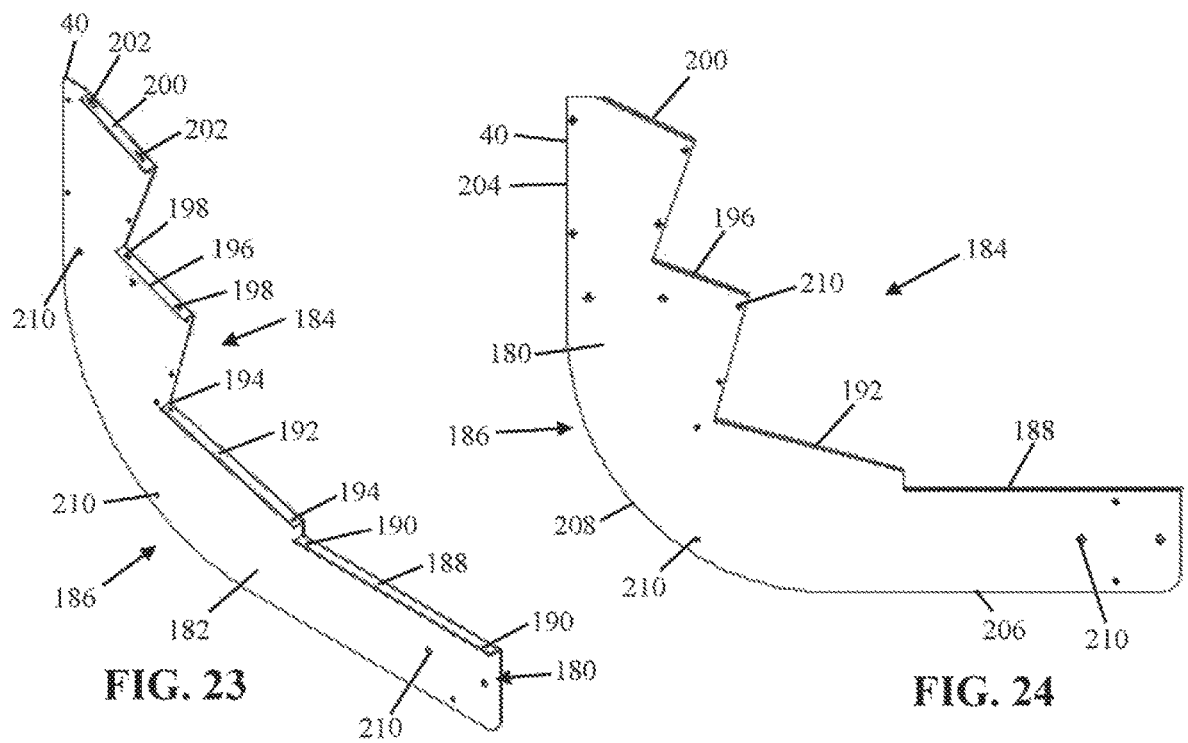

SURGICAL TRAY EFFICIENCY SYSTEM AND RELATED METHODS

CROSS-REFERENCES TO RELATED APPLICATIONS

The present application is a continuation and claims priority to U.S. application Ser. No. 16/397,853, filed on Apr. 29, 2019, which is a continuation and claims priority to U.S. application Ser. No. 15/478,219 filed on Apr. 3, 2017, which is a non-provisional application claiming the benefit of priority from commonly owned U.S. Provisional Application Ser. No. 62/317,544 filed on Apr. 2, 2016 and entitled "SURGICAL TRAY EFFICIENCY SYSTEM," and is a continuation-in-part of U.S. application Ser. No. 15/055,280 filed Feb. 26, 2016 and entitled "CANTILEVER ORGANIZATIONAL RACK SYSTEM FOR SUPPORTING SURGICAL INSTRUMENTATION," which claims the benefit of priority from U.S. Provisional Application Ser. No. 62/121,710 filed on Feb. 27, 2015 and entitled "CANTILEVER ORGANIZATIONAL RACK SYSTEM FOR SUPPORTING SURGICAL INSTRUMENTATION," the entire content of each aforementioned patent application is hereby incorporated by reference into this disclosure as if set forth fully herein.

FIELD

The present invention relates generally to the effective organization and use of surgical instrumentation for a given surgical procedure. In particular, the invention relates to system of component devices; a hardware component, a sterile barrier with location identification, and a software platform.

BACKGROUND

Various cabinets, racks, tables and shelving have been used for assembling, storing, and transporting medical instruments, tools, and implant devices throughout hospitals and surgery centers for medical operations and procedures. Typically surgical instruments, tools and implant devices are washed, sterilized, wrapped, and stored until required instrumentation is set up in the operating room prior to surgery or a medical procedure.

The numerous personnel including but not limited to patients, hospital administration, surgeons, nursing staff, scrub technicians, sterile processing employees, device manufacturers, manufacturers' representatives along with the vast number of tools and instruments required for a specific surgery creates a need for precise coordination. The number of incidents that occur because of miscommunication, lack of teamwork and the extensive level of variables can be hard to quantify and are rarely published, however the monetary cost can be estimated using an average operating cost per min. Incidents that occur in and around the operating room have been found to incur high monetary costs and correlate directly with increased infection rates and lengthened recovery times. The lack of procedure protocols prior to, during, and after surgery increases the risk of incidents and contributes to high health care costs.

SUMMARY

Operating efficiency and production is being propelled by patient expectations, health care regulations, and advancing technology. Despite increasing efforts to capitalize on the glaring complications in the operating environment, miniscule achievements have been developed. The present invention increases efficiency in the operating room by establishing a workflow network within the operating environment by implementing an effective system that creates accountability and standardizes patient care. By focusing on systematic procedural techniques with equipment and personnel workflow, the number of hazardous outcomes can be reduced.

The present invention is directed to various designs for a surgical tray efficiency system for use in the operating room during surgery to hold instruments. Preferred features for the design of the present invention include the following:
  i. multi-level rack design with adjustable angle shelves;
  ii. modular rack units and options allow for customized room set-up based on surgeon, procedure, instrument requirements, and space limitations;
  iii. mobility for easy movement of the racks around the hospital and operating room;
  iv. rack includes a custom sterile drape;
  v. rack allows for co-branding opportunities, such as company and hospital brand, procedure techniques, logos, etc.
  vi. adjustable spine angle and orientation for technician or surgeon comfort and/or visual preferences;
  vii. rack may be designed to support at least 2 or more full instruments trays per shelf level;
  viii. rack ensures a consistent protocol for the use of surgical instruments; and
  ix. rack utilizes a specialized location planogram software system that creates consistency throughout the surgical industry it is being used in.

Various embodiments of the present invention may exhibit one or more of the following objects, features and/or advantages:
  i. reduces or eliminates need for sterile cloth drapes to cover stainless steel tables;
  ii. helps organize equipment trays with increased visibility from across the room and accessibility of instruments inside an operating room;
  iii. reduces occurrence of situations where instruments are lost or misplaced due to a disorganized and inconsistent surgical room set-up and inventory management;
  iv. allows accessible and organized surgery room storage of hundreds of instruments;
  v. prevents instrument trays from being "stacked" together during long surgical procedures and associated risk of bacteria growth;
  vi. reduces or eliminates sterile field violations due to lack of floor space in sterile working area;
  vii. helps reduce hospital infection rate;
  viii. improved portability, instrument work space, efficiency, safety and/or standardization;
  ix. helps to reduce the number of personnel in the operating room during surgery;
  x. reduces inefficiencies associated with instrumentation and implant use;
  xi. creates opportunity for better space management of operating rooms;
  xii. creates a standardized protocol for instrumentation use depending on surgery type, surgeon, and device manufacturer; and
  xiii. allows a manufacturer's representative to be more effective and efficient.

The vertical rack organizational system of the present invention helps to increase efficiency in the operating room by: (1) improving organization (by having a specified location for each instrument tray); (2) increasing the space available for instrument trays; (3) ensuring every tray has the necessary instruments before the procedure begins; (4) increasing visibility of the instruments for the surgeon and support staff; (5) enhancing the tracking of tools; (6) reducing surgery time; and (7) decreasing the incidence of misplaced instruments before, during, or after procedures.

The vertical rack organization system accomplishes this by using a modular hardware system that adapts with seamless integration using a multifaceted software structure including a planogram set up to map tool and tray location. The modular hardware system comprises a vertical rack that includes a base, support arms, instrument shelves, and a header. The base may function to support the load, store or house a power supply and/or systems (mechanical and/or electrical) for adjusting or moving aspects of the modular hardware system, and provide smooth mobility (via attached lockable castors, for example) to enable out of the way storage. The instrument shelves are configured to receive sterile instrument trays, and may be provided in different lengths that would be appropriate for accommodating a single column of trays (e.g. "single-wide"), two columns of trays ("e.g. double-wide"), three columns of trays (e.g. "triple-wide"), and so forth. The instrument shelves may be color-coded and numbered. The numbering and color-coding system corresponds to specific instrument trays, ensuring their proper placement within the vertical rack system.

As additional description to the embodiments described below, the present disclosure describes the following embodiments.

Embodiment 1 is a system for increasing efficiency in an operating room environment during a surgical procedure, comprising: (1) a multi-level shelf assembly comprising a plurality of elongated shelves vertically separated from one another, each elongated shelf configured to hold at least one standard surgical instrument tray; (2) a sterile identification barrier overlaying the multi-level shelf assembly to create a physical barrier between a sterile field of an operating room and the multi-level shelf assembly, the sterile identification barrier including a plurality of tray-receiving areas, each sized and configured to overlay at least a portion of one of the elongated shelves, and each tray-receiving area having a unique tray-receiving area location identifier associated therewith; and (3) computer-readable media including instructions that, when executed by one or more processors, are configured to cause a computer system to: (a) receive surgical planning data that is related to a given surgical procedure and that is input by a user and (b) provide, on a display device, an interactive presentation of the surgical planning data.

Embodiment 2 is the system of embodiment 1, wherein each elongated shelf has a generally planar display surface.

Embodiment 3 is the system of embodiments 1 or 2, wherein the plurality of elongated shelves includes a first shelf having a generally planar display surface oriented parallel to the ground.

Embodiment 4 is the system of embodiment 3, wherein the plurality of elongated shelves includes a second shelf having a generally planar display surface arranged in a nonparallel orientation relative to the first shelf.

Embodiment 5 is the system of any one of embodiments 1 through 4, wherein each tray-receiving area is configured to contain only one standard surgical instrument tray therein.

Embodiment 6 is the system of any one of embodiments 1 through 5, wherein the surgical planning data comprises (i) surgical instrument tray content that indicates surgical instruments to be stored on various surgical instrument trays, and (ii) tray-receiving area location identifiers that correspond directly to the tray-receiving area location identifiers of the sterile identification barrier, and that indicate the locations of the various surgical instrument trays on the sterile identification barrier during the given surgical procedure.

Embodiment 7 is the system of embodiment 6, wherein the interactive presentation includes: (i) the surgical instruments that are to be stored on the various surgical instrument trays, and (ii) the locations of the various surgical instrument trays on the sterile identification barrier during the given surgical procedure.

Embodiment 8 is the system of any one of embodiments 4 through 7, wherein the plurality of elongated shelves further includes a third shelf having a generally planar display surface arranged in a nonparallel orientation relative to the first shelf.

Embodiment 9 is the system of embodiment 8, wherein the generally planar display surface of the third shelf is arranged in a nonparallel orientation relative to the second shelf.

Embodiment 10 is the system of embodiments 8 or 9, wherein the plurality of elongated shelves further includes a fourth shelf having a generally planar display surface arranged in a nonparallel orientation relative to the first shelf.

Embodiment 11 is the system of embodiment 10, wherein the generally planar display surface of the fourth shelf is arranged in a nonparallel orientation relative to the second and third shelves.

Embodiment 12 is the system of embodiment 10 or 11, wherein the first, second, third and fourth shelves are equal in length.

Embodiment 13 is the system of any one of embodiments 10-12, wherein the first shelf has a width dimension that is greater than the width dimensions of the second, third, and fourth shelves.

Embodiment 14 is the system of any one of embodiments 1 through 13, wherein the display device is attached to the multi-level shelf assembly.

Embodiment 15 is the system of any one of embodiments 1 through 14, wherein unique location identifiers on the sterile identification barrier comprise at least one of letters, numbers, colors, symbols, and words.

Embodiment 16 is the system of any one of embodiments 1 through 15, wherein the sterile identification barrier further includes a plurality of bendable wires positioned thereon to secure the sterile identification barrier to the multi-level shelf assembly.

Embodiment 17 is the system of any one of embodiments 1 through 16, wherein the sterile identification barrier is at least partially secured to the multi-level shelf assembly by hook and loop fasteners.

Embodiment 18 is the system of any one of embodiments 1 through 17, wherein the surgical instrument tray content comprises a plurality of surgical instruments.

Embodiment 19 is the system of any one of embodiments 1 through 18, wherein the surgical planning data input by the user further comprises one or more of hospital name, surgeon name, procedure name, procedure-related literature, procedure-related video media, instrument-specific video media, instrument images, and surgery preference notes.

Embodiment 20 is the system of any one of embodiments 1 through 19, wherein the instructions are further configured to cause the computer system to: (i) provide one or more user interface elements that enable a user to search for a surgical instrument by name, and (ii) present, in response to user input that provides a name of a surgical instrument and initiates a search using the one or more user interface elements, information that indicates a surgical instrument tray on which a surgical instrument having the name is located.

Embodiment 21 is the system of embodiment 20, wherein the interactive presentation includes a virtual representation of the location on the sterile identification barrier of the surgical instrument that has the name.

Embodiment 22 is the system of any one of embodiments 1 through 21, wherein the multi-level shelf assembly is mounted to the ceiling of the operating room.

Embodiment 23 is the system of any one of embodiments 1 through 22, wherein the instructions are further configured to cause the computer system to: (i) receive a request to provide a second computer system that coordinates movements of a robotic device with a location of a particular surgical instrument, wherein the request indicates the particular surgical instrument; (ii) identify a surgical instrument tray, of the various surgical instrument trays, at which the particular surgical instrument is located; and (iii) send, for receipt by the computer system that coordinates movements of the robotic device in response to having received the request, information that indicates the surgical instrument tray at which the particular surgical instrument is located.

Embodiment 24 is the system of embodiment 23, wherein the instructions are further configured to cause the computer system to: (iv) receive, from the computer system that coordinates movements of the robotic device, information that indicates that the robotic device has retrieved the particular surgical instrument; and (v) provide, on the display device, an update to the interactive presentation to visually indicate that the particular surgical instrument has been retrieved by the robotic device.

Embodiment 25 is a method for increasing efficiency in an operating room environment during a given surgical procedure, comprising the steps of: (1) providing a plurality of surgical instrument trays, each containing one or more surgical instruments related to the given surgical procedure; (2) providing a multi-level shelf assembly comprising a plurality of elongated shelves vertically separated from one another, each elongated shelf having a generally planar display surface configured to hold at least one surgical instrument tray; (3) draping a sterile identification barrier over the multi-level shelf assembly to create a physical barrier between the sterile field of the operating room environment and the multi-level shelf assembly, the sterile identification barrier including a plurality of tray-receiving areas, each sized and configured to overlay at least a portion of one of the elongated shelves, each tray-receiving area having a unique location identifier associated therewith; (4) inputting surgical planning data related to a given surgical procedure into a computer system; and (5) interacting, with a computer system that is providing, on a display device, an interactive presentation of a compilation of the surgical planning data, to cause the display device to present a particular aspect of the surgical planning data.

Embodiment 26 is the method of embodiment 25, wherein each tray-receiving area is configured to contain only one surgical instrument tray therein.

Embodiment 27 is the method of embodiments 25 or 26, wherein the surgical planning data comprises: (i) surgical instrument tray content that indicates surgical instruments to be stored on various surgical instrument trays, and (ii) tray-receiving area location identifiers that correspond directly to the tray-receiving area location identifiers of the sterile identification barrier, and that indicate the locations of the various surgical instrument trays on the sterile identification barrier during the given surgical procedure.

Embodiment 28 is the method of any one of embodiments 25 through 27, further comprising the step of: affixing a unique location identifier tag to the surgical instrument trays, the unique location identifier tag corresponding to the locations of the various surgical instrument trays on the sterile identification barrier during the given surgical procedure.

Embodiment 29 is the method of any one of embodiments 25 through 28, further comprising the step of: placing the specific surgical instrument tray with affixed location identifier tag within the tray-receiving area having the corresponding tray-receiving area location identifier.

Embodiment 30 is the method of any one of embodiments 25 through 29, wherein the compilation of the surgical planning data includes: (i) the surgical instruments that are to be stored on the various surgical instrument trays, and (ii) the locations of the various surgical instrument trays on the sterile identification barrier during the given surgical procedure.

Embodiment 31 is the method of any one of embodiments 25 through 30, wherein the particular aspect of the surgical planning data includes an enlarged view of the particular surgical instrument tray.

Embodiment 32 is the method of any one of the embodiments 25-31, wherein the display device is attached to the multi-level shelf assembly.

Embodiment 33 is the method of any one of embodiments 25 through 32, wherein unique location identifiers on the sterile identification barrier comprise at least one of letters, numbers, colors, symbols, and words.

Embodiment 34 is the method of any one of embodiments 25 through 33, wherein the surgical planning data input by the user comprises one or more of hospital name, surgeon name, procedure name, procedure-related literature, procedure-related video media, instrument-specific video media, instrument images, and surgery preference notes.

BRIEF DESCRIPTIONS OF THE DRAWINGS

Many advantages of the present disclosure will be apparent to those skilled in the art with a reading of this specification in conjunction with the attached drawings, wherein like reference numerals are applied to like elements and wherein:

FIG. 12 is a perspective view of an example of a pair of vertical supports forming part of the vertical rack assembly of FIG. 8

FIG. 13 is a top plan view of the pair of vertical supports of FIG. 12;

FIG. 14 is a perspective view of an example of a protective shell forming part of the vertical rack assembly of FIG. 8;

FIG. 15 is a side plan view of the protective shell of FIG. 13;

FIGS. 21-22 are perspective and side plan views, respectively, of an example of a first side support panel forming part of the vertical rack assembly of FIG. 8;

FIGS. 23-24 are perspective and side plan views, respectively, of an example of a second side support panel forming part of the vertical rack assembly of FIG. 8;

DETAILED DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The surgical tray efficiency system and related methods disclosed herein boasts a variety of inventive features and components that warrant patent protection, both individually and in combination.

Figure 1:
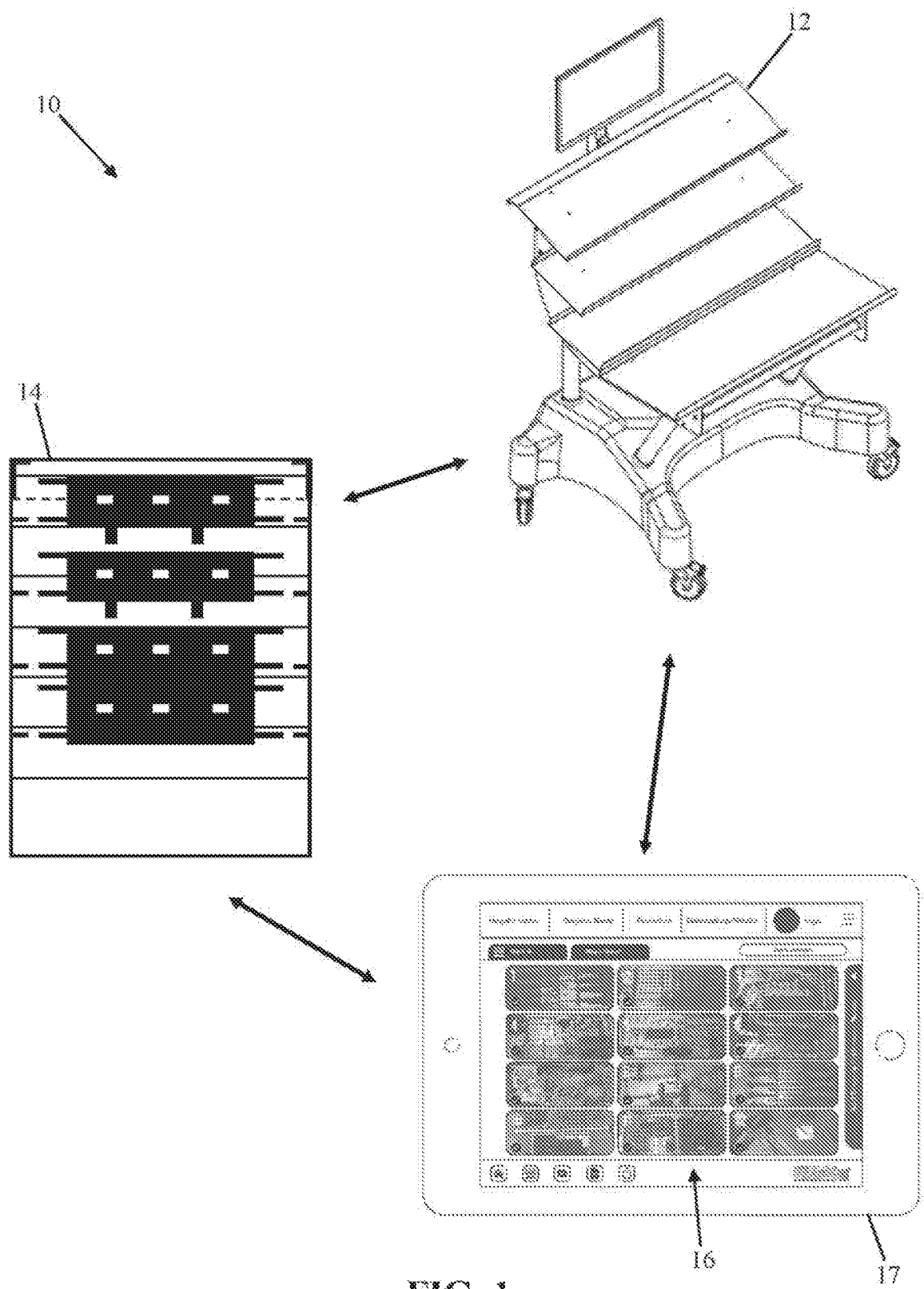
FIG. 1 is a perspective view of an example of a surgical tray efficiency system according to the disclosure.
Figure 2:
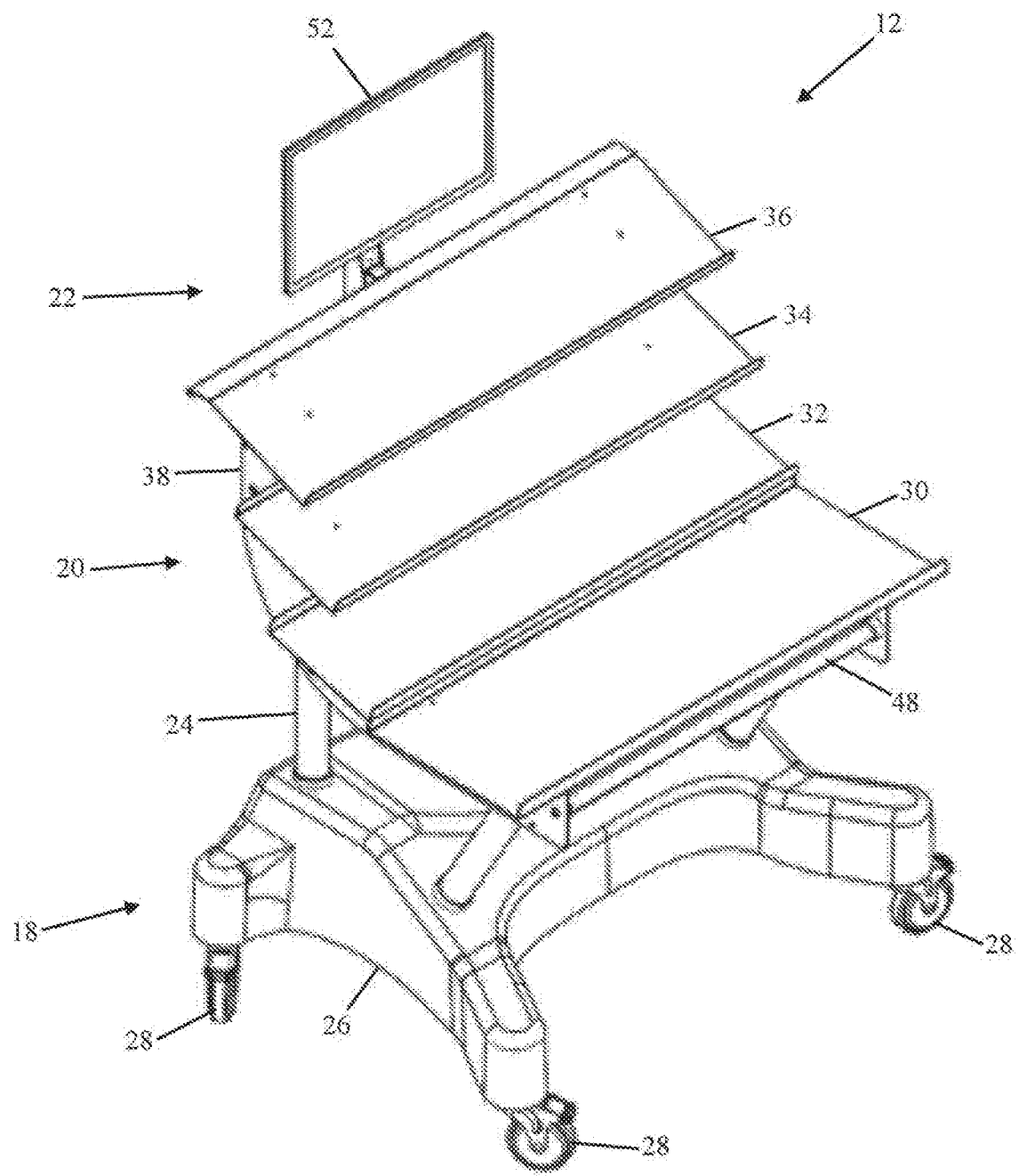
FIG. 2 is a perspective view of one example of vertical rack assembly forming part of the surgical tray efficiency system of FIG. 1.

FIG. 1 illustrates one example of a surgical tray efficiency system 10 designed for use in an operating room during surgery. By way of example, the surgical tray efficiency system 10 includes a vertical rack assembly 12, a sterile identification barrier 14, and a standardization software platform 16, shown by way of example on a portable tablet computer 17. The various components of the surgical tray efficiency system 10 interact with one another to enable operating room personnel to quickly locate and retrieve requested instrumentation during surgery, thereby improving operating room efficiency and reducing surgery time. More specifically, the vertical rack assembly 12 is ergonomically designed to utilize vertical space in the operating room by having a plurality of angled shelves that each support one or more surgical instrument trays. The vertical rack assembly 12 has a relatively small footprint to surface area ratio, which maximizes the number and accessibility of surgical instrument trays while occupying a minimal amount of valuable floor space within the operating room. The sterile identification barrier 14 allows the vertical rack assembly 12 to be positioned inside the sterile field in an operating room by establishing a sterile barrier between the vertical rack assembly 12 and the rest of the operating room. Additionally, the sterile identification barrier 14 may include labels that correlate to a specific location or region on the sterile identification barrier 14 which, in conjunction with the standardization software platform 16, allows the operating room personnel to maintain consistency of the placement of the various instrument trays according to the preferences and/or pre-planning by the surgical team. The standardization software platform 16 guides a user where to place an instrument tray for a given labeled location on the sterile identification barrier 14. Thus, the surgical tray efficiency system 10 increases operating room efficiency by (a) having a consistent, specified location for each instrument tray; (b) increasing the space available for instrument trays; (c) ensuring every tray has the necessary instruments before the procedure begins; (d) increasing visibility of the instruments for the surgeon and support staff; (e) enhancing the tracking of surgical instruments; and (f) decreasing the incidence of misplaced instruments before, during, or after surgical procedures.

FIGS. 2-7 illustrate one example of a vertical rack assembly 12 according to the present disclosure. By way of example, the vertical rack assembly 12 includes a base assembly 18, shelf assembly 20, and a monitor assembly 22. The base assembly includes a support structure 24, a shell 26, and a plurality of mobility elements 28. The shelf assembly 20 includes a plurality of metal shelves, each configured to hold at least one surgical instrument tray. The vertical rack assembly 12 shown by way of example in FIGS. 2-6 includes a first shelf 30, a second shelf 32, a third shelf 34, and a fourth shelf 36, each of which are configured to hold and display at least two standard sized (e.g. 23×11 inches) surgical instrument trays (e.g. "double-wide"). Other shelf configurations are possible, such that the vertical rack assembly 12 may be provided with more shelves or fewer shelves, and/or shorter shelves (e.g. "single-wide" shelves configured to hold at least one standard sized instrument tray per shelf) or longer shelves (e.g. "triple-wide" shelves configured to hold at least three standard sized instrument trays per shelf) depending on the instrumentation needs of a particular surgical procedure. The shelf assembly 20 further includes first and second lateral support panels 38, 40, first, second, and third rear panels 42, 44, 46, a grab handle 48, and a pivot bar 50. The monitor assembly 22 includes a monitor 52, monitor support 54, and a pivot handle 56. Optionally, the vertical rack assembly 12 may include an attached mounting element for at least temporarily receiving the portable electronic device 17 that is used to interface with the standardization software platform 16. The vertical rack assembly 12 may also include an attached container for housing a plurality of sterile identification barriers 14 therein.

Figure 3:
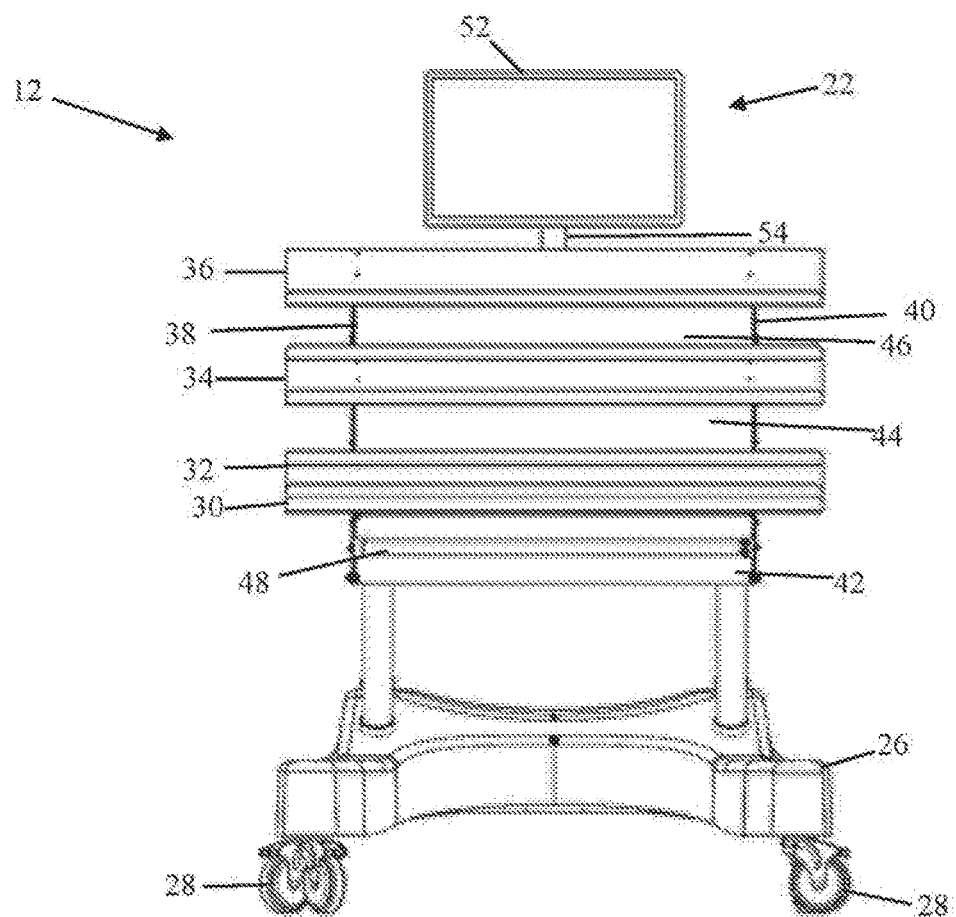
FIG. 3 is a front plan view of the vertical rack assembly of FIG. 2.
Figure 4:
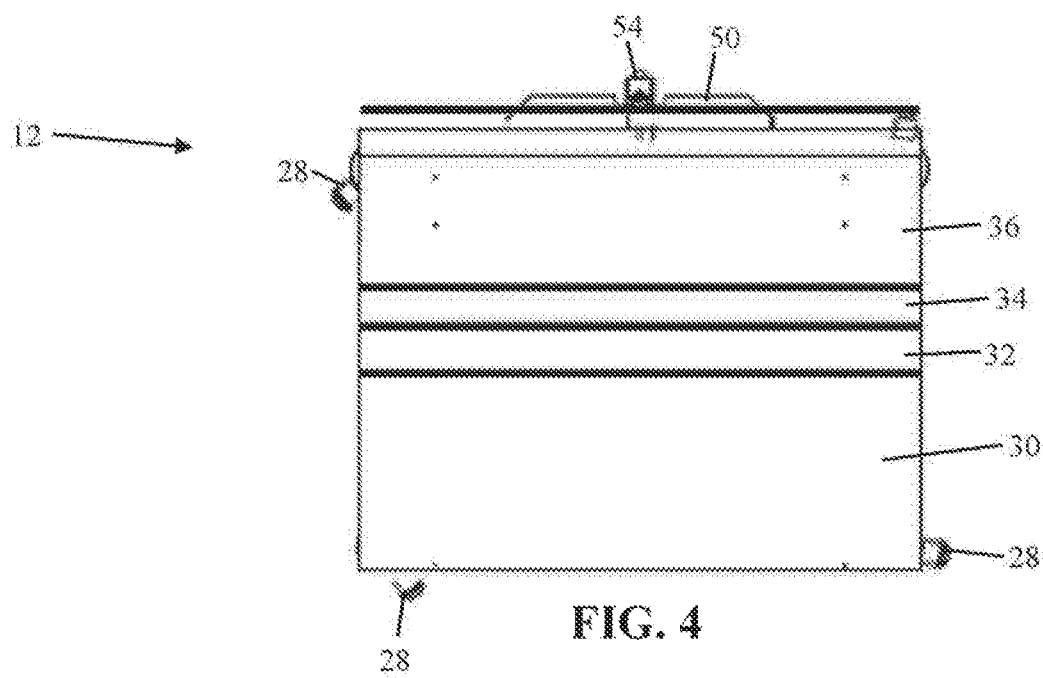
FIG. 4 is a top plan view of the vertical rack assembly of FIG. 2.
Figure 5:
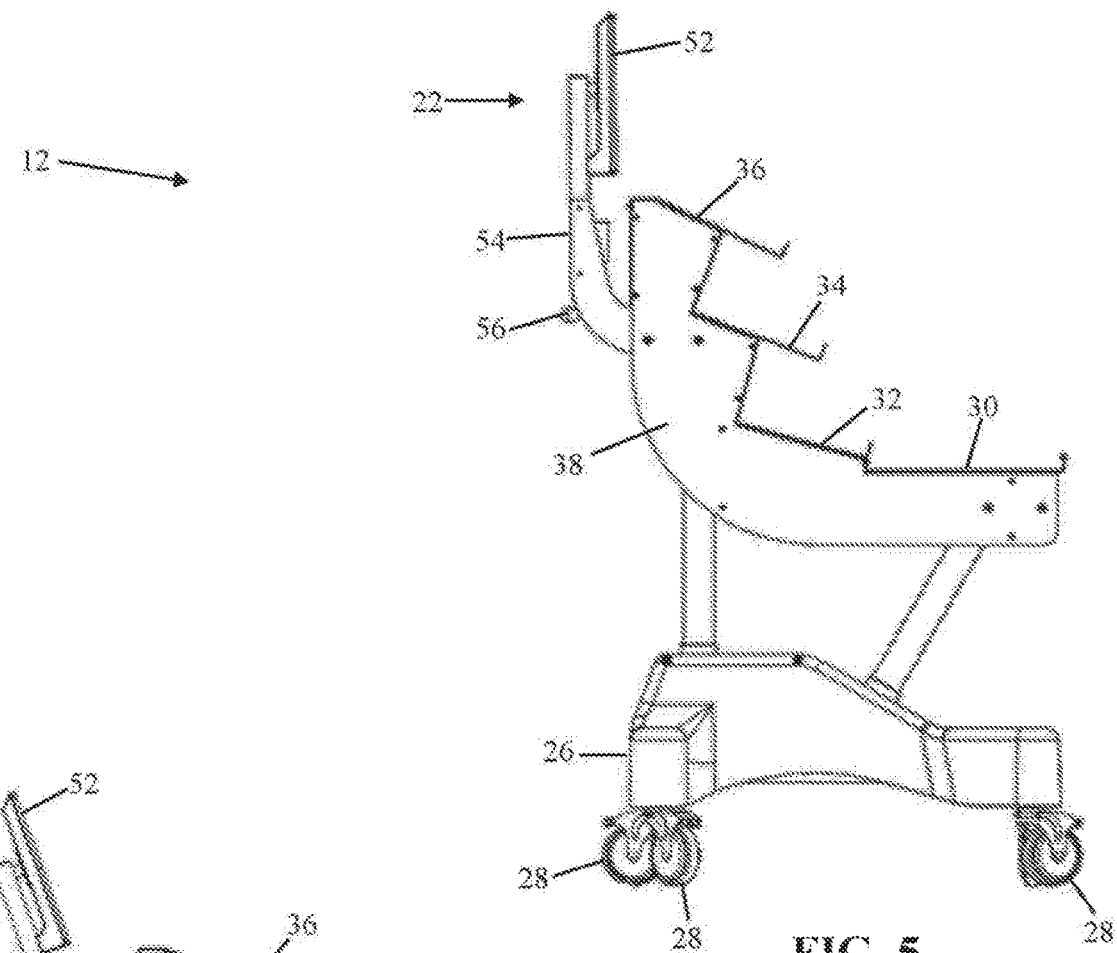
FIGS. 5-6 are side plan views of the vertical rack assembly of FIG. 2.

The various views presented in FIGS. 3-5 not only show different perspectives of the component parts that make up the vertical rack assembly 12, they also highlight certain advantageous characteristics of the vertical rack assembly 12. For example, FIG. 3 is a front view of the vertical rack assembly 12 highlighting in particular the compact height of the vertical rack assembly 12 as well as the width component of the footprint. FIG. 4 is a top view of the vertical rack assembly 12 highlighting in particular the overall compact footprint (e.g. width and depth components) that minimizes operating room floor space that must be dedicated to storing surgical instrument trays. FIG. 5 is a side view of the vertical rack assembly 12 highlighting in particular the cascading multiple angled shelves providing the increased surface area necessary for the ergonomic accessibility of all the surgical instruments inside each instrument tray.

Figure 8:
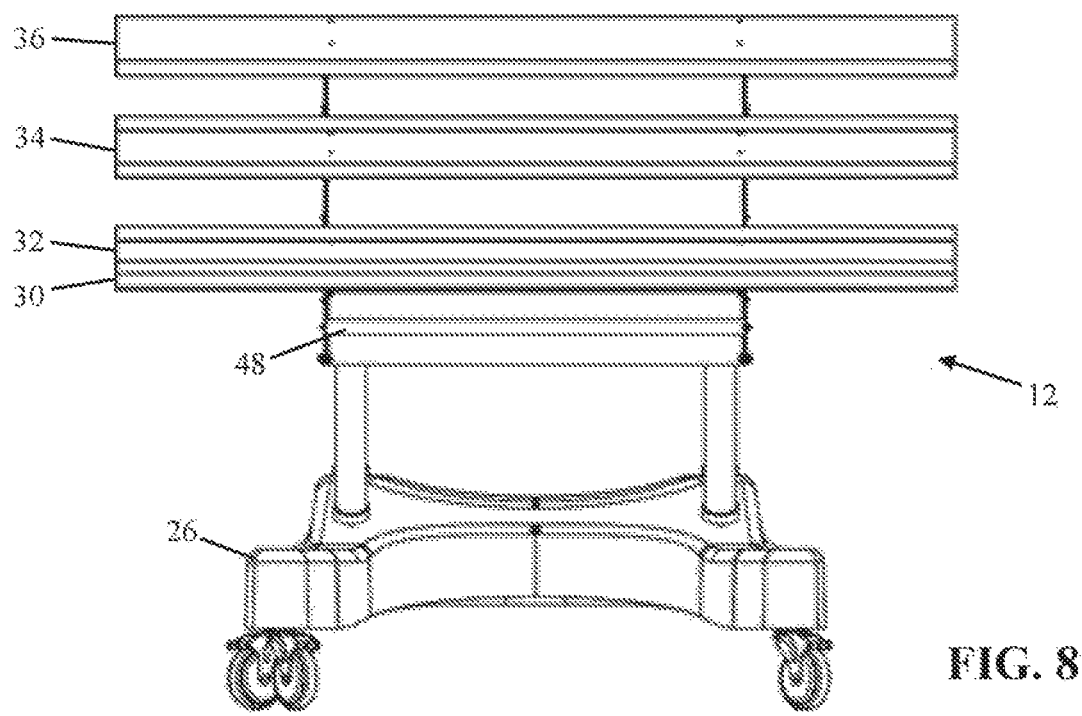
FIG. 8 is a front plan view of another example of a vertical rack assembly forming part of the surgical tray efficiency system of FIG. 1.
Figure 9:
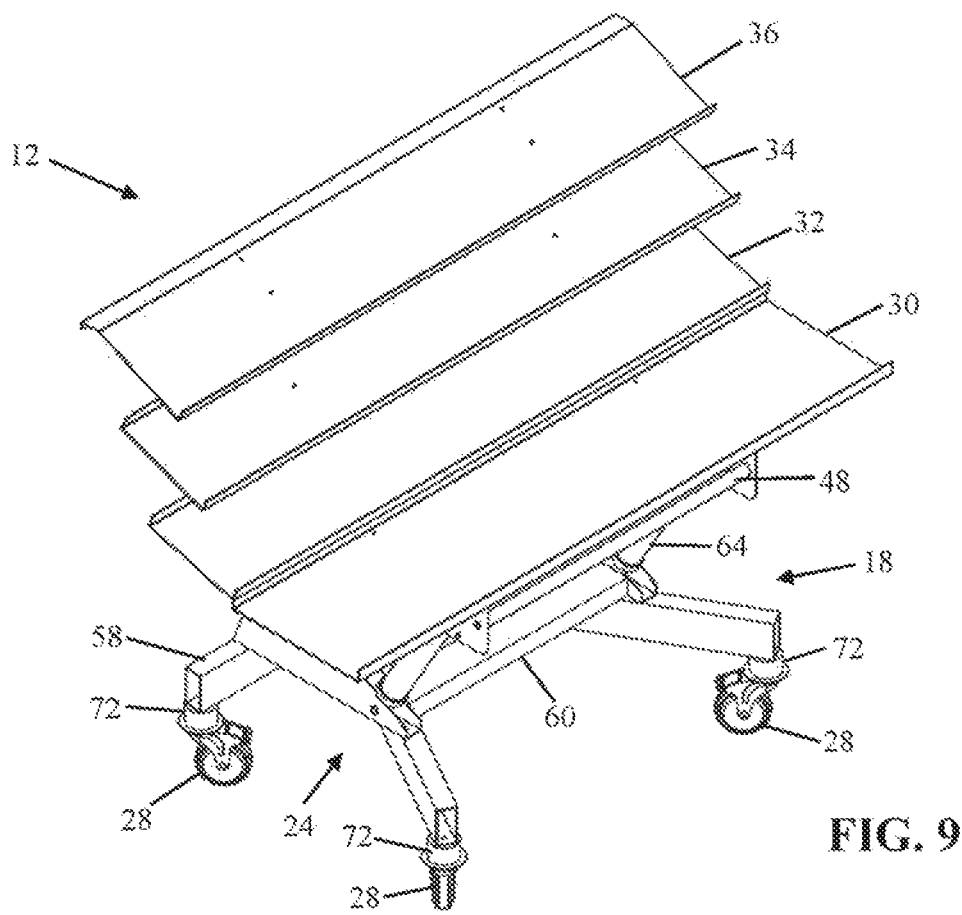
FIG. 9 is a perspective view of the vertical rack assembly of FIG. 8.

Referring to FIGS. 8-15, the base assembly 18 will now be described in further detail. As previously mentioned, the base assembly includes a support structure 24, a shell 26, and a plurality of mobility elements 28. FIG. 8 is a plan view of a "triple-wide" vertical rack assembly 12. FIG. 9 is an isometric view of the "triple-wide" vertical rack assembly 12 shown without the monitor assembly 22 and the shell 26, illustrating in particular (at least partially) the support structure 24. By way of example, the support structure 24 includes a base frame 58, a support base 60, and first and second vertical supports 62, 64.

Figure 10:
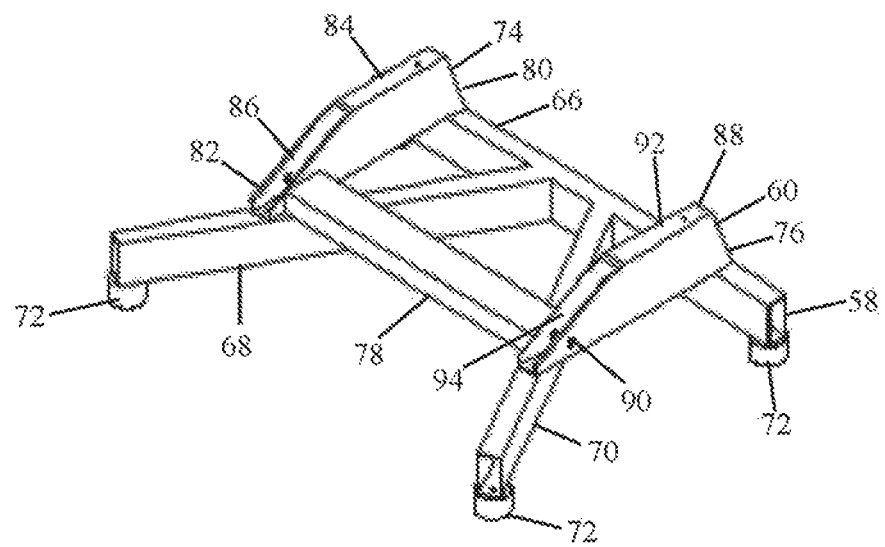
FIG. 10 is a perspective view of an example of a base frame forming part of the vertical rack assembly of FIG. 8.
Figure 11:
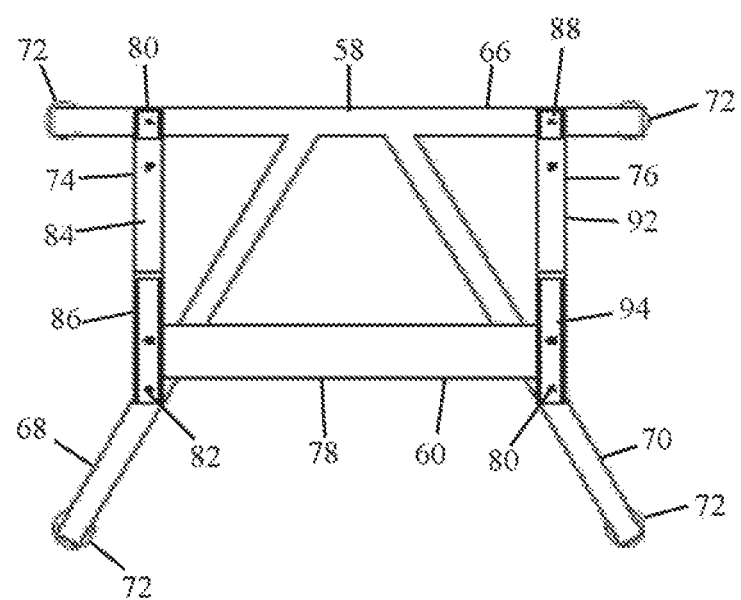
FIG. 11 is a top plan view of the base frame of FIG. 10.

Referring to FIGS. 10 and 11, the base frame 58 includes a lateral support beam 66 and a pair of angled support beams 68, 70. The lateral support beam 66 is positioned such that it forms the back perimeter of the footprint, and includes a mobility element connector 72 at each end. The first angled support beam 68 extends from a first point near the midpoint of the lateral support beam 66 outward toward one of the front corners of the footprint at an approximately 60° angle relative to the lateral support beam 66 and includes a mobility element connector 72 at the distal end. The second angled support beam 70 extends from a second point near the midpoint of the lateral support beam 66 (on the opposite side of the midpoint from the point of attachment of the first angled support beam 68) outward toward the other front corner of the footprint at an approximately 60° angle relative to the lateral support beam 66, and includes a mobility element connector 72 at the distal end.

The support base 60 includes first and second longitudinal support beams 74, 76 and a lateral support beam 78. The first longitudinal support beam 74 is positioned on one side of the base frame 58 and has a proximal end 80, a distal end 82, a planar top surface 84, and a beveled distal surface 86. The proximal end 80 is attached to the horizontal support beam 66 of the base frame 58, and the distal end 82 is attached to the first angled support beam 68. The planar top surface 84 is configured to mechanically engage a portion of the first vertical support 62 to securely maintain the first vertical support 62 in a ninety-degree orientation relative to the floor. The beveled distal surface 86 is configured to mechanically engage a portion of the second vertical support 64 to securely maintain the second vertical support 64 in an angled orientation relative to the floor. The second longitudinal support beam 76 is positioned on the opposite side of the base frame 58 from the first longitudinal support beam 74 and has a proximal end 88, a distal end 90, a planar top surface 92, and a beveled distal surface 94. The proximal end 88 is attached to the horizontal support beam 66 of the base frame 58, and the distal end 90 is attached to the second angled support beam 70. The planar top surface 92 is configured to mechanically engage a portion of the first vertical support 62 to securely maintain the first vertical support 62 in a 90° orientation relative to the floor. The beveled distal surface 94 is configured to mechanically engage a portion of the second vertical support 64 to securely maintain the second vertical support 64 in an angled orientation relative to the floor. By way of example only, this angled orientation may be approximately 60° however other angles are possible.

Referring to FIGS. 12 and 13, the first vertical support 62 includes first and second leg elements 96, 98, and a crossbar 100. The first leg element 96 includes a base 102 that attaches to the planar top surface 84 described above. The attachment may be achieved via any suitable method for secure attachment, including nut and bolt, pin, welding, and the like. The second leg element 98 includes a base 104 that attaches to the planar top surface 92 described above. The attachment may be achieved via any suitable method for secure attachment, including nut and bolt, pin, welding, and the like. The first and second leg elements 96, 98 are attached to opposite ends of the crossbar 100. The crossbar 100 extends between and attaches to the first and second lateral support bars 38, 40, described in further detail below. The second vertical support 64 includes first and second leg elements 106, 108, and a crossbar 110. The first leg element 106 includes a base 112 that attaches to the beveled distal surface 86 described above. The attachment may be achieved via any suitable method for secure attachment, including nut and bolt, pin, welding, and the like. The second leg element 108 includes a base 114 that attaches to the beveled distal surface 94 described above. The attachment may be achieved via any suitable method for secure attachment, including nut and bolt, pin, welding, and the like. The first and second leg elements 106, 108 are attached to opposite ends of the crossbar 110. The crossbar 110 extends between and attaches to the first and second lateral support bars 38, 40, described in further detail below.

Referring to FIGS. 14 and 15, the shell 26 comprises a thermoformed plastic (by way of example) element that covers the base frame 58 and support base 60, to ensure the base assembly 18 is easy to clean while creating a stylized design that is impact resistant and pleasing to the eyes with smooth flowing curvature. The shell 26 includes a pair of lateral extensions 116 that cover the distal ends of the lateral support beam 66, including the mobility element connectors 72 positioned thereon. The shell 26 further includes a pair of angled extensions 118 that cover the distal ends of the first and second angled support beams 68, 70, including the mobility element connectors 72 positioned thereon. Additionally, the shell 26 includes a plurality of apertures 120 formed therethrough to allow for the extension of the various leg elements of the first and second vertical supports 62, 64. The apertures 120 each include an escutcheon ring 121 attached thereto. The escutcheon rings 121 physically engage the vertical supports 62, 64 and mechanically connect the frame assembly to the vertical supports 62, 64 so that the thermoformed shell 26 does not bear any weight. The shell 26 further includes a front cutaway portion 122 that allows a user to stand closer to the instrument trays, minimizing the need for an operating room technician to endure uncomfortable reaching during a surgical procedure.

The mobility elements 28 may be any suitable mechanism to allow for easy movement (e.g. positioning, transfer, storage, etc) of the vertical rack assembly 12 within an operating room, between operating rooms, and/or between a storage room and operating room. Referring again to FIG. 8, and by way of example only, the mobility elements 28 of the current example may be lockable swivel casters.

Figure 16:
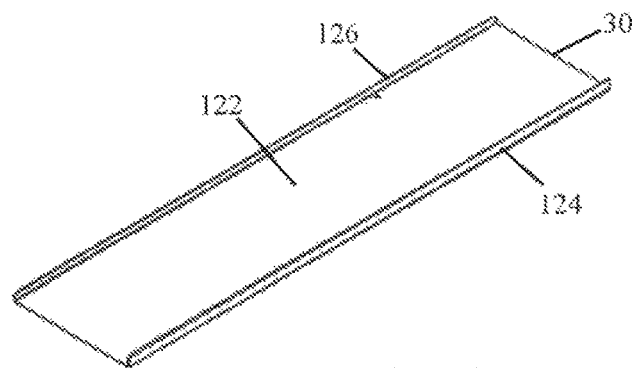
FIG. 16 is a perspective view of an example of a first shelf forming part of the vertical rack assembly of FIG. 8.

Referring now to FIGS. 16-27, the shelf assembly 20 will be described in further detail. FIG. 16 illustrates an example of the first shelf 30. The first shelf 30 includes a generally rectangular, planar panel 122 that serves as the surface upon which the surgical instrument trays are located. A first elongated flange 124 is positioned on one long perimeter edge of the rectangular panel 122 and has a height dimension extending generally perpendicularly from the panel 122 and a length dimension coinciding with the long edge of the rectangular panel 122. A second elongated flange 126 is positioned on the opposite long perimeter edge of the rectangular panel 122 and has a height dimension extending generally perpendicularly from the panel 122 and a length dimension coinciding with the long edge of the rectangular panel 122. The first and second elongated flanges function to prevent migration (e.g. forward and backward) of surgical instrument trays that are placed on the first shelf 30. By way of example only, the first shelf 30 has a length dimension of approximately 68 inches and a width dimension of approximately 16 inches. Other length and/or width dimensions are possible depending upon the size and number of surgical instrument trays required by a surgical procedure. For example, the first shelf 30 in the "double-wide" vertical rack assembly 12 shown in FIGS. 2-7 may have a length dimension of approximately 46 inches. In the example shown and described herein, the first shelf 30 comprises the bottommost shelf on the vertical rack assembly 12 and has a slightly larger width dimension than the other shelves to accommodate larger surgical instrument trays. As can be seen in FIG. 5, the first shelf 30 in the present example is aligned in a generally parallel orientation relative to the operating room floor.

Figure 17:
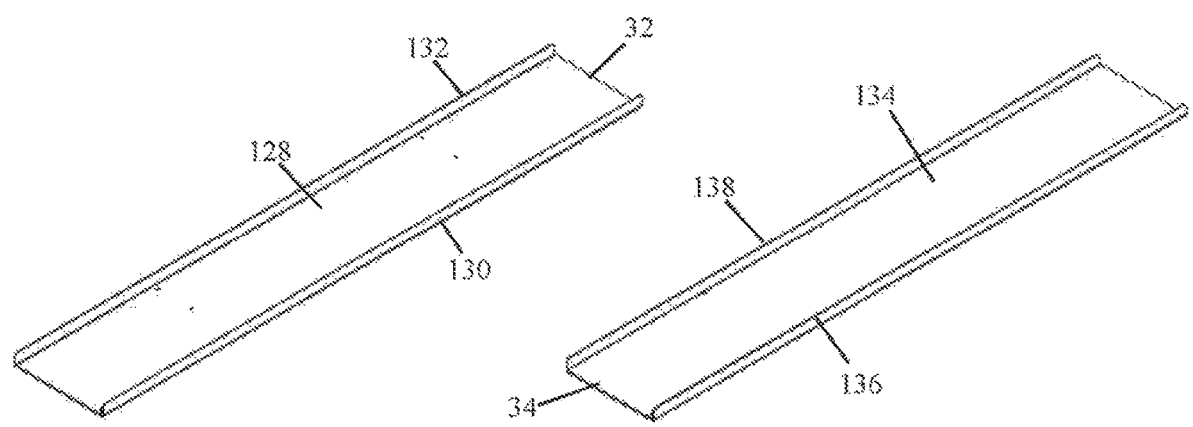
FIG. 17 is a perspective view of an example of a second shelf forming part of the vertical rack assembly of FIG. 8.

FIG. 17 illustrates an example of a second shelf 32. The second shelf 32 includes a generally rectangular, planar panel 128 that serves as the surface upon which the surgical instrument trays are located. A first elongated flange 130 is positioned on one long perimeter edge of the rectangular panel 128 and has a height dimension extending generally perpendicularly from the panel 128 and a length dimension coinciding with the long edge of the rectangular panel 128. A second elongated flange 132 is positioned on the opposite long perimeter edge of the rectangular panel 128 and has a height dimension extending generally perpendicularly from the panel 128 and a length dimension coinciding with the long edge of the rectangular panel 128. The first and second elongated flanges 130, 132 function to prevent migration (e.g. forward and backward) of surgical instrument trays that are placed on the second shelf 32. By way of example only, the second shelf 32 has a length dimension of approximately 68 inches and a width dimension of approximately 11 inches. Other length and width dimensions are possible depending upon the size and number of surgical instrument trays required by a surgical procedure. For example, the second shelf 32 in the "double-wide" vertical rack assembly 12 shown in FIGS. 2-7 may have a length dimension of approximately 45.5 inches. In the example shown and described herein, the second shelf 32 comprises the lower middle shelf (of four total shelves) on the vertical rack assembly 12. As can be seen in FIG. 5, the second shelf 32 in the present example is aligned in a generally non-parallel, angled orientation relative to the first shelf 30.

Figure 18:
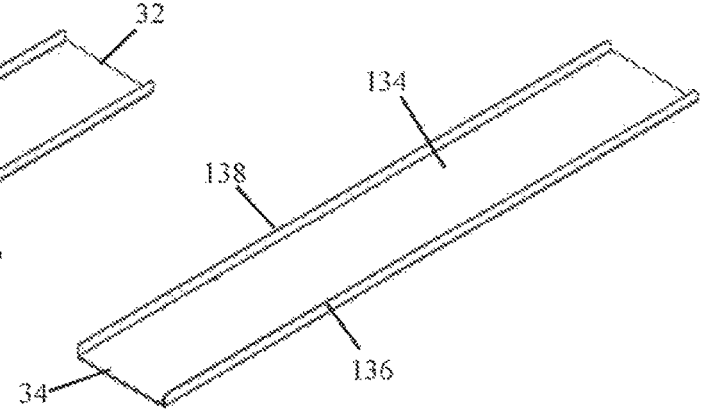
FIG. 18 is a perspective view of an example of a third shelf forming part of the vertical rack assembly of FIG. 8.

FIG. 18 illustrates an example of the third shelf 34. The third shelf 34 includes a generally rectangular, planar panel 134 that serves as the surface upon which the surgical instrument trays are located. A first elongated flange 136 is positioned on one long perimeter edge of the rectangular panel 134 and has a height dimension extending generally perpendicularly from the panel 134 and a length dimension coinciding with the long edge of the rectangular panel 134. A second elongated flange 138 is positioned on the opposite long perimeter edge of the rectangular panel 134 and has a height dimension extending generally perpendicularly from the panel 134 and a length dimension coinciding with the long edge of the rectangular panel 134. The first and second elongated flanges 134, 138 function to prevent migration (e.g. forward and backward) of surgical instrument trays that are placed on the third shelf 34. By way of example only, the third shelf 34 has a length dimension of approximately 68 inches and a width dimension of approximately 11 inches. Other length and width dimensions are possible depending upon the size and number of surgical instrument trays required by a surgical procedure. For example, the third shelf 34 in the "double-wide" vertical rack assembly 12 shown in FIGS. 2-7 may have a length dimension of approximately 45.5 inches. In the example shown and described herein, the third shelf 34 comprises the upper middle shelf (of four total shelves) on the vertical rack assembly 12. As can be seen in FIG. 5, the third shelf 34 in the present example is aligned in a generally angled orientation relative to the first shelf 30. By way of example, the angle of the third shelf 34 may be different than the angle of the second shelf.

Figure 19:
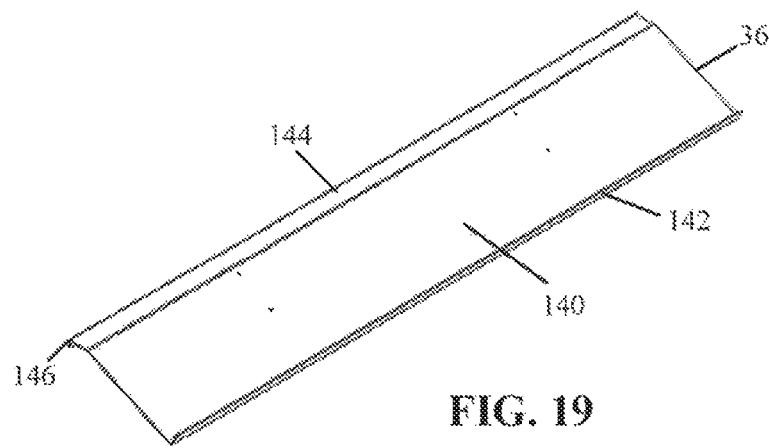
FIG. 19 is a perspective view of an example of a fourth shelf forming part of the vertical rack assembly of FIG. 8.
Figure 20:
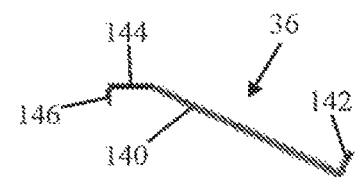
FIG. 20 is a side plan view of the fourth shelf of FIG. 19.

FIGS. 19-20 illustrate an example of the fourth shelf 36. The fourth shelf 36 includes a generally rectangular, planar panel 140 that serves as the surface upon which the surgical instrument trays are located. A first elongated flange 142 is positioned on one long perimeter edge of the rectangular panel 140 and has a height dimension extending generally perpendicularly from the panel 140 and a length dimension coinciding with the long edge of the rectangular panel 140. A second elongated flange 144 is positioned on the opposite long perimeter edge of the rectangular panel 140 and has a width dimension extending angularly away from the panel 134 and a length dimension coinciding with the long edge of the rectangular panel 134. A third elongated flange 146 is positioned on the opposite long perimeter edge of the second elongated flange 144 and has a height dimension extending generally perpendicularly from the second elongated flange 146 in a downward vertical direction and a length dimension coinciding with the long edge of the second elongated flange 144. The first elongated flange 142 functions to prevent migration (e.g. forward) of surgical instrument trays that are placed on the fourth shelf 36. The second and third elongated flanges 144, 146 function to keep bacteria and other surgical debris on the outside of the vertical rack assembly 12. By way of example only, the fourth shelf 36 (e.g. each component thereof) has a length dimension of approximately 68 inches, the rectangular panel 140 has a width dimension of approximately 11 inches, and the second elongated flange has a width dimension of approximately 2 inches. Other length and width dimensions are possible depending upon the size and number of surgical instrument trays required by a surgical procedure. For example, the fourth shelf 36 in the "double-wide" vertical rack assembly 12 shown in FIGS. 2-6 may have a length dimension of approximately 45.5 inches. In the example shown and described herein, the fourth shelf 36 comprises the upper-most shelf (of four total shelves) on the vertical rack assembly 12. As can be seen in FIGS. 5 and 20, the fourth shelf 36 in the present example is positioned in such a way that the rectangular panel 140 is aligned in a generally angled orientation relative to the operating room floor and the second elongated flange 144 is generally parallel to the first shelf 30. By way of example, the angle of the fourth shelf 36 may be different than the angle of the third shelf 34 and/or the angle of the second shelf 32.

FIGS. 21-22 illustrate the first lateral support panel 38 in greater detail. The first lateral support panel 38 comprises a generally planar first (e.g. "outer-facing") surface 148, a second (e.g. "inner-facing") surface 150, a first (e.g. "front-facing") side 152 and a second (e.g. "rear-facing") side 154. The portion of the perimeter of the first lateral support panel 38 that comprises the front-facing side 152 includes a plurality of shelf support flanges oriented in a generally "terraced" manner. For example, the first shelf support flange 156 comprises a generally rectangular planar flange extending generally perpendicularly from the first lateral support panel 38 in the direction of the inner-facing surface 150. The first shelf support flange 156 is oriented generally parallel to the floor and is configured to support a first end of the first shelf 30 described above. The first shelf support flange 156 includes a pair of attachment elements 158 located at either longitudinal end of the support flange 156. By way of example, the attachment elements 158 may comprise any suitable attachment mechanism, for example including but not limited to apertures for receiving a screw, pin, rivet, etc. Optionally, the first lateral support panel 38 may include an additional aperture (not shown) for receiving at least a portion of a holder/receptacle configured to receive the portable electronic device 17 used to interface with the standardization software platform 16 (e.g. tablet computer, smart phone, etc) when not in use.

The second shelf support flange 160 comprises a generally rectangular planar flange extending generally perpendicularly from the first lateral support panel 38 in the direction of the inner-facing surface 150. The second shelf support flange 160 is oriented at a slight angle relative to the floor and is configured to support a first end of the second shelf 32 described above. The second shelf support flange 160 includes a pair of attachment elements 162 located at either longitudinal end of the support flange 160. By way of example, the attachment elements 162 may comprise any suitable attachment mechanism, for example including but not limited to apertures for receiving a screw, pin, rivet, etc.

The third shelf support flange 164 comprises a generally rectangular planar flange extending generally perpendicularly from the first lateral support panel 38 in the direction of the inner-facing surface 150. The third shelf support flange 164 is oriented at a slight angle relative to the floor and is configured to support a first end of the third shelf 34 described above. The third shelf support flange 164 includes a pair of attachment elements 166 located at either longitudinal end of the support flange 164. By way of example, the attachment elements 166 may comprise any suitable attachment mechanism, for example including but not limited to apertures for receiving a screw, pin, rivet, etc.

The fourth shelf support flange 168 comprises a generally rectangular planar flange extending generally perpendicularly from the first lateral support panel 38 in the direction of the inner-facing surface 150. The fourth shelf support flange 168 is oriented at a slight angle relative to the floor and is configured to support a first end of the fourth shelf 36 described above. The fourth shelf support flange 168 includes a pair of attachment elements 168 located at either longitudinal end of the support flange 168. By way of example, the attachment elements 170 may comprise any suitable attachment mechanism, for example including but not limited to apertures for receiving a screw, pin, rivet, etc.

The portion of the perimeter of the first lateral support panel 38 that comprises the rear-facing side 154 includes a vertically oriented straight portion 172 and a horizontally oriented straight portion 174 separated by a gradually arcuate portion 176. This arrangement reduces material used and minimizes the weight and bulkiness of the vertical rack assembly 12. The first lateral support panel 38 further includes a plurality of attachment elements 178 (e.g. apertures for receiving a screw, pin, rivet, and the like) dispersed thereon to enable attachment of the first and second vertical supports 62, 64, grab handle 48, and the horizontal panels 42, 44, 46.

FIGS. 23-24 illustrate the second lateral support panel 40 in greater detail. The second lateral support panel 40 is essentially a mirror image of the first lateral support panel 38 described above. The second lateral support panel 40 comprises a generally planar first (e.g. "outer-facing") surface 180, a second (e.g. "inner-facing") surface 182, a first (e.g. "front-facing") side 184 and a second (e.g. "rear-facing") side 186. The portion of the perimeter of the second lateral support panel 40 that comprises the front-facing side 184 includes a plurality of shelf support flanges oriented in a generally "terraced" manner. For example, the first shelf support flange 188 comprises a generally rectangular planar flange extending generally perpendicularly from the second lateral support panel 40 in the direction of the inner-facing surface 182. The first shelf support flange 188 is oriented generally parallel to the floor and is configured to support a second end of the first shelf 30 described above. The first shelf support flange 188 includes a pair of attachment elements 190 located at either longitudinal end of the support flange 188. By way of example, the attachment elements 190 may comprise any suitable attachment mechanism, for example including but not limited to apertures for receiving a screw, pin, rivet, etc. Optionally, the second lateral support panel 40 may include an additional aperture (not shown) for receiving at least a portion of a holder/receptacle configured to receive the portable electronic device 17 used to interface with the standardization software platform 16 (e.g. tablet computer, smart phone, etc) when not in use.

The second shelf support flange 192 comprises a generally rectangular planar flange extending generally perpendicularly from the second lateral support panel 40 in the direction of the inner-facing surface 182. The second shelf support flange 192 is oriented at a slight angle relative to the floor and is configured to support a second end of the second shelf 32 described above. The second shelf support flange 192 includes a pair of attachment elements 194 located at either longitudinal end of the support flange 192. By way of example, the attachment elements 194 may comprise any suitable attachment mechanism, for example including but not limited to apertures for receiving a screw, pin, rivet, etc.

The third shelf support flange 196 comprises a generally rectangular planar flange extending generally perpendicularly from the second lateral support panel 40 in the direction of the inner-facing surface 182. The third shelf support flange 196 is oriented at a slight angle relative to the floor and is configured to support a second end of the third shelf 34 described above. The third shelf support flange 196 includes a pair of attachment elements 198 located at either longitudinal end of the support flange 196. By way of example, the attachment elements 198 may comprise any suitable attachment mechanism, for example including but not limited to apertures for receiving a screw, pin, rivet, etc.

The fourth shelf support flange 200 comprises a generally rectangular planar flange extending generally perpendicularly from the second lateral support panel 40 in the direction of the inner-facing surface 182. The fourth shelf support flange 200 is oriented at a slight angle relative to the floor and is configured to support a second end of the fourth shelf 36 described above. The fourth shelf support flange 200 includes a pair of attachment elements 202 located at either longitudinal end of the support flange 200. By way of example, the attachment elements 202 may comprise any suitable attachment mechanism, for example including but not limited to apertures for receiving a screw, pin, rivet, etc.

The portion of the perimeter of the second lateral support panel 40 that comprises the rear-facing side 186 includes a vertically oriented straight portion 204 and a horizontally oriented straight portion 206 separated by a gradually arcuate portion 208. This arrangement reduces material used and minimizes the weight and bulkiness of the vertical rack assembly 12. The second lateral support panel 40 further includes a plurality of attachment elements 210 (e.g. apertures for receiving a screw, pin, rivet, and the like) dispersed thereon to enable attachment of the first and second vertical supports 62, 64, grab handle 48, and the rear panels 42, 44, 46.

Figure 25:
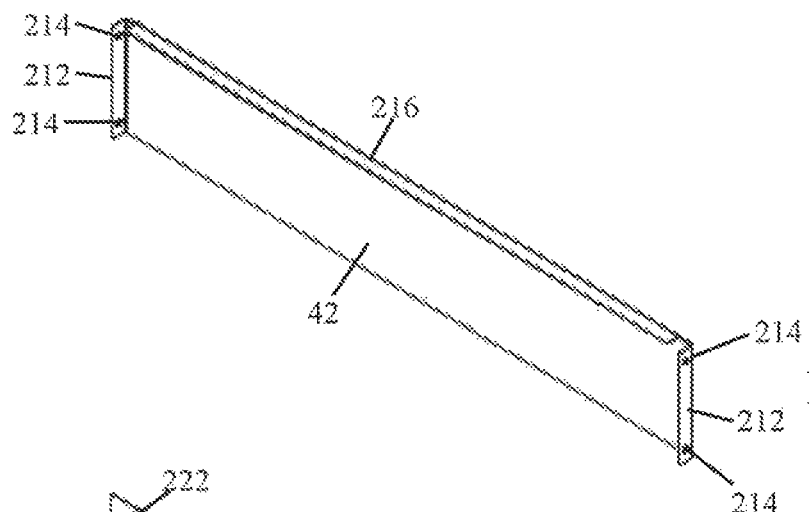
FIG. 25 is a perspective view of an example of a first rear panel forming part of the vertical rack assembly of FIG. 8.
Figure 26:
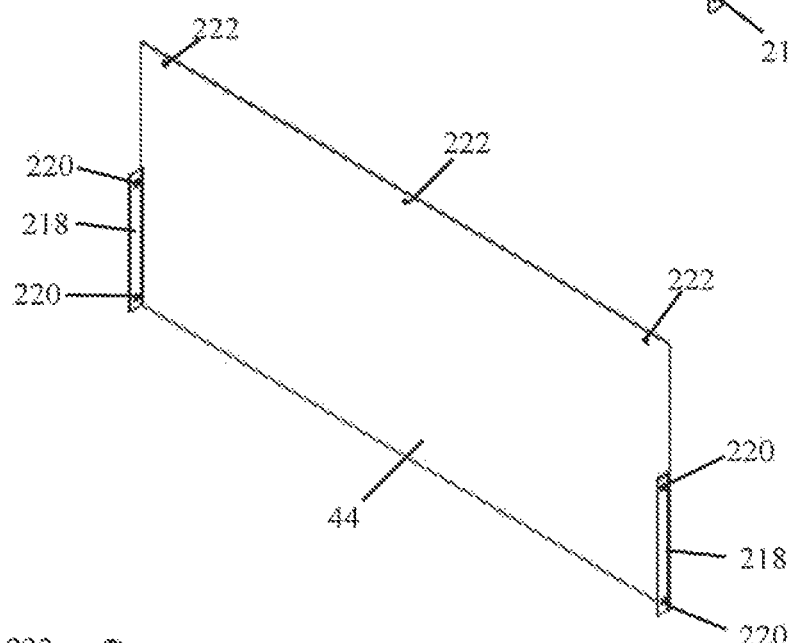
FIG. 26 is a perspective view of an example of a second rear panel forming part of the vertical rack assembly of FIG. 8.
Figure 27:
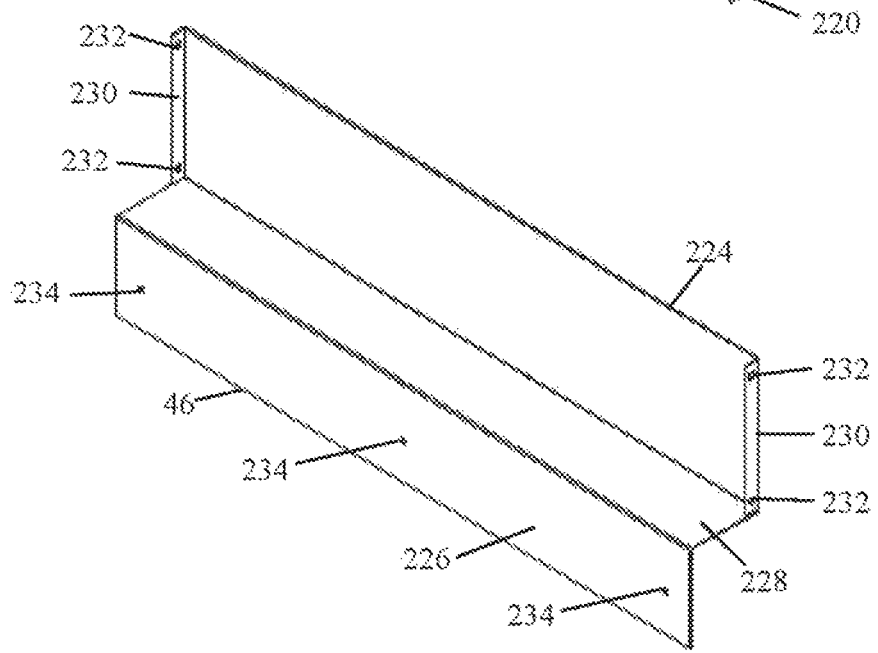
FIG. 27 is a perspective view of an example of a third rear panel forming part of the vertical rack assembly of FIG. 8.

FIGS. 25-27 illustrate several examples of filler panels and curtains (e.g. rear panels) that function to close off the design of the vertical rack assembly 12 so that there are minimal bacterial ingress sites as well as create a rear face that is easy to clean for example with sterilizing solution. FIG. 25 illustrates an example of a first rear panel 42 configured for positioning behind the grab handle 48 (see e.g. FIG. 3). The first rear panel 42 comprises a generally rectangular planar member including a pair of attachment flanges 212 each having a plurality of attachment elements 214 (e.g. apertures for receiving a screw, pin, rivet, and the like) dispersed thereon to enable attachment to the first and second lateral support panels 38, 40. The first rear panel 42 further includes an additional flange 216 positioned along one of the elongated edges to help keep bacteria and other surgical debris on the outside of the vertical rack assembly 12.

Figure 7:
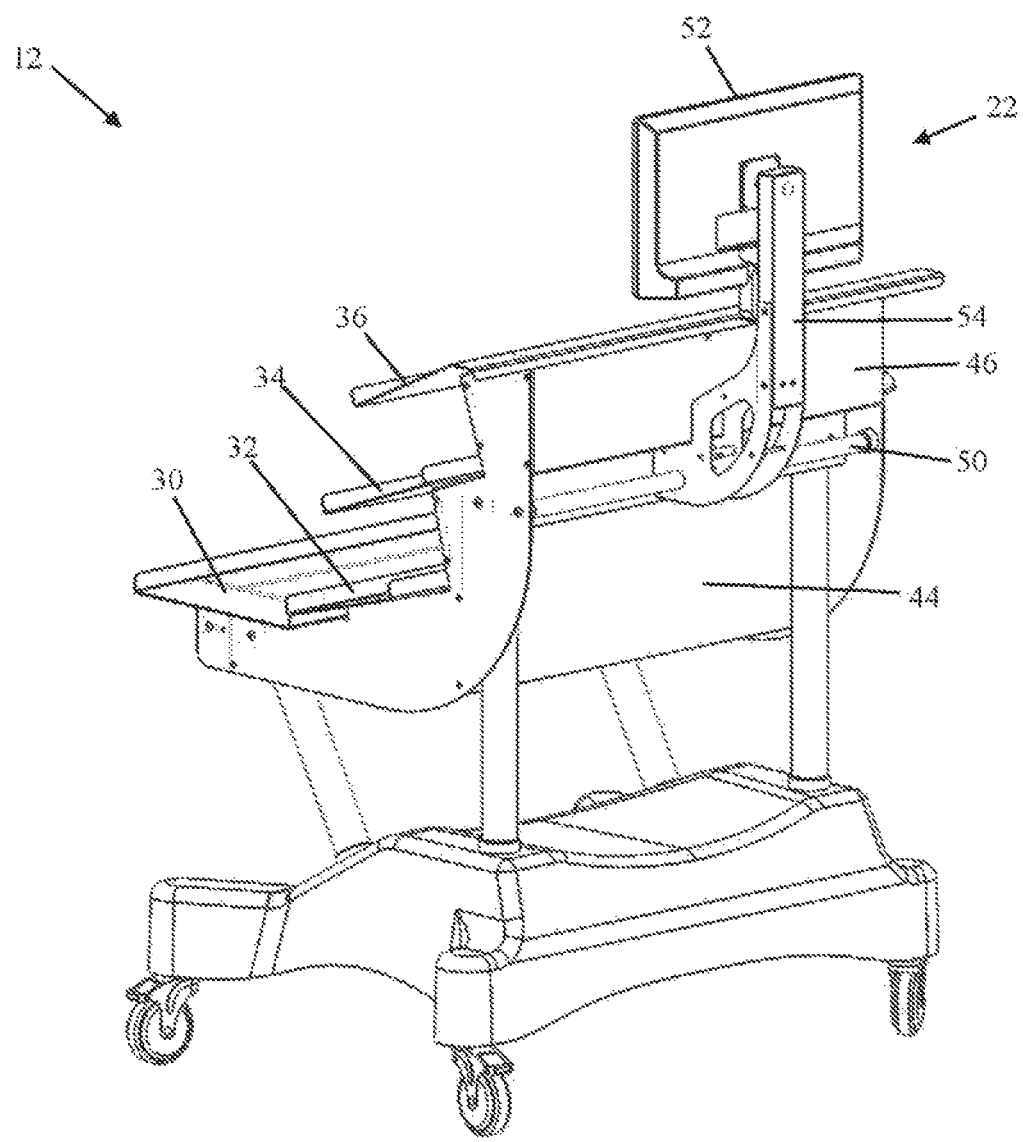
FIG. 7 is a rear perspective view of the vertical rack assembly of FIG. 2.

FIG. 26 illustrates an example of a second rear panel 44 configured for positioning behind the first and second shelves 30, 32 (see e.g. FIGS. 3 and 7). The second rear panel 44 comprises a generally rectangular planar member including a pair of attachment flanges 218 each having a plurality of attachment elements 220 (e.g. apertures for receiving a screw, pin, rivet, and the like) dispersed thereon to enable attachment to the first and second lateral support panels 38, 40. The second rear panel 44 further includes an additional attachment elements 222 positioned along one of the elongated edges to facilitate attachment to the third rear panel 46 to create a continuous rear panel.

FIG. 27 illustrates an example of a third rear panel 46 configured for positioning behind the third and fourth shelves 34, 36 (see e.g. FIGS. 3 and 7). The third rear panel 46 includes a first vertically oriented generally rectangular planar portion 224, a second vertically oriented generally rectangular planar portion 226, and a horizontally oriented generally rectangular planar portion 228 extending between the first and second vertically oriented portions 224, 226. The first vertically oriented portion 224 includes a pair of attachment flanges 230 each having a plurality of attachment elements 232 (e.g. apertures for receiving a screw, pin, rivet, and the like) dispersed thereon to enable attachment to the first and second lateral support panels 38, 40. The second vertical portion 226 includes additional attachment elements 234 positioned therein to facilitate attachment to the second rear panel 44 to create a continuous rear panel.

Figure 28:
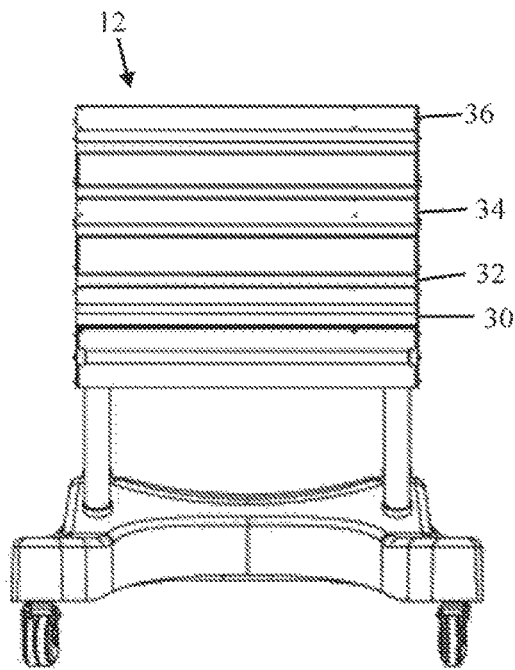
FIG. 28 is a front plan view of another example of a vertical rack assembly forming part of the surgical tray efficiency system of FIG. 1.

FIG. 28 illustrates an example of a vertical rack assembly 12 having first, second, third, and fourth shelves 30, 32, 34, 36 that are configured to hold at least one surgical instrument tray (e.g. "single-wide") per shelf. Such a rack could be used for surgical procedures needing few instrument trays.

Referring again to FIGS. 5-7, the monitor assembly 22 will now be discussed in further detail. FIGS. 5 and 7 show the vertical rack assembly 12 with a monitor assembly 22 attached and in the "in use" position. The monitor 52 can be used to display various aspects of the standardization software platform 16. The monitor 52 may be equipped with touch-screen technology enabling direct data input or alternatively the monitor 52 may be display only. According to one embodiment, the standardization software platform 16 may be loaded on to a portable computer device, for example a portable tablet computer 17 (e.g. FIG. 1), smart phone, laptop computer, and the like. In such a case, the user interfaces with the standardization software platform 16 using the portable computer device, and the monitor displays a mirrored image of the display on the portable computer device, using wireless communication technology such as (by way of example) Bluetooth, Airplay, WiFi, and the like.

The monitor 52 is designed with similar curvature as the cascading shelves while allowing for cord management. The monitor assembly 22 is also mounted to a pivot bar 50 located well below the top of vertical rack assembly 12 in order to create the necessary room for the sterile identification barrier 14 behind the vertical rack assembly 12. The monitor assembly 22 is also designed so that the monitor 52 is above and behind the top of the vertical rack assembly 12 in order to maintain the visibility of the monitor 52 during the surgical procedure.

Figure 6:
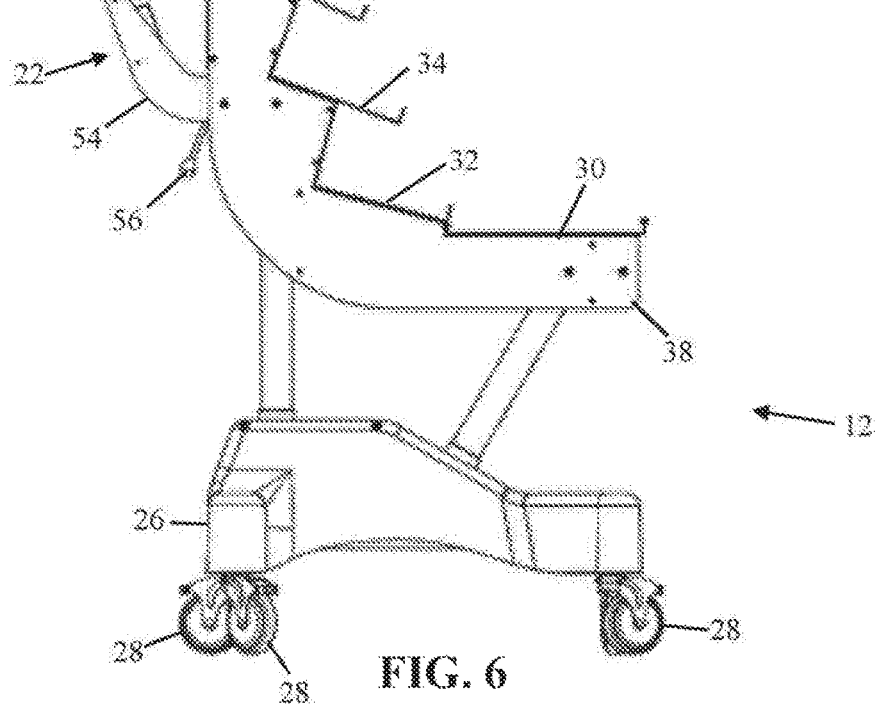

FIG. 6 shows the monitor assembly 22 in a draping position. A pivot handle 56 attached to a rolling cam assembly is used to release the monitor assembly 22 to enable it to pivot about the pivot bar 50 and create a greater angle between the monitor 52 and the back plane of the vertical rack assembly 12. The adjustment of the monitor assembly 22 allows an unsterile person to drape a sterile monitor cover over the monitor 52 and pivot the monitor assembly 22 back into the "in use" position without breaking sterile protocol. The pivot bar 50 may also be used by a person located outside the sterile field to maneuver the vertical rack assembly 12 into or about the sterile field without contaminating the sterile field. Thus, a person in the sterile field does not have to leave the sterile field to move the vertical rack assembly 12.

Figure 29:
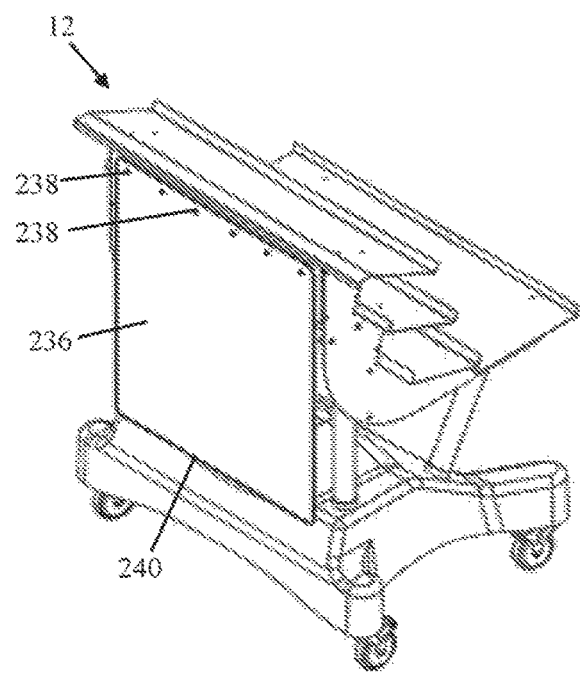
FIG. 29 is a rear perspective view of the vertical rack assembly of FIG. 2 with an example of an attached x-ray shield.
Figure 30:
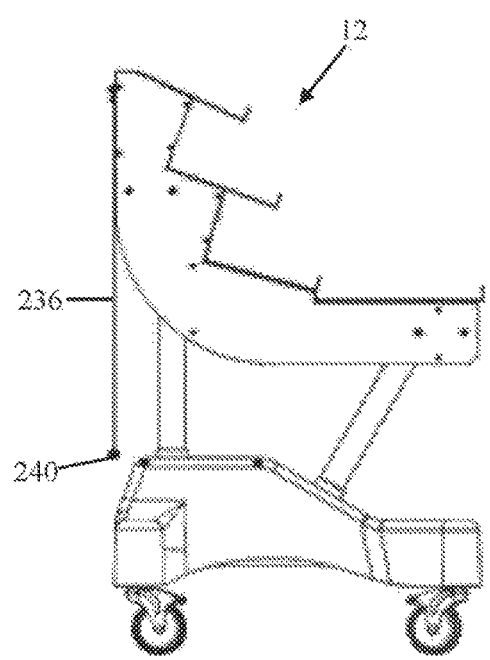
FIG. 30 is a side plan view of the vertical rack assembly of FIG. 29.
Figure 31:
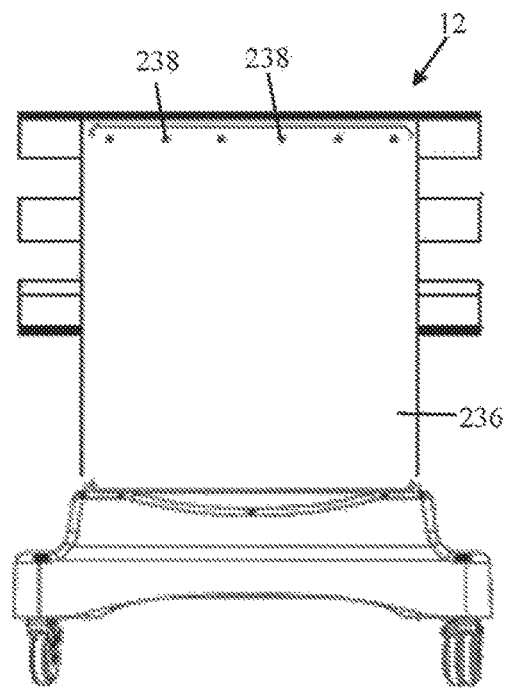
FIG. 31 is a rear plan view of the vertical rack assembly of FIG. 29.

Referring now to FIGS. 29-31, an example of a vertical rack assembly 12 with an attached X-Ray barrier 236 is described. The X-Ray barrier 236 is lined sufficiently in order to limit the penetration of harmful radiation that is used in an operating room during a surgical procedure. The X-Ray barrier 236 allows any person or persons in the operating room to shield themselves from the harmful effects of radiation by positioning themselves such that the X-Ray barrier 236 is between themselves and the radiation source. By way of example, the X-Ray barrier 236 includes a plurality of attachment elements 238 configured to enable attachment of the X-Ray barrier 236 to the vertical rack assembly 12, and a weight element 240 to ensure that the X-Ray barrier 240 is fully extended during the surgical procedure to provide maximum protection to anyone standing behind it.

Additional examples of vertical shelf assemblies may be found in commonly-owned U.S. Pat. No. 8,074,815 to Gerstner (incorporated by reference) and commonly owned U.S. patent application Ser. No. 15/055,280, filed on Feb. 26, 2016, entitled CANTILEVER ORGANIZATIONAL RACK SYSTEM FOR SUPPORTING SURGICAL INSTRUMENTATION (incorporated by reference).

Figure 32:
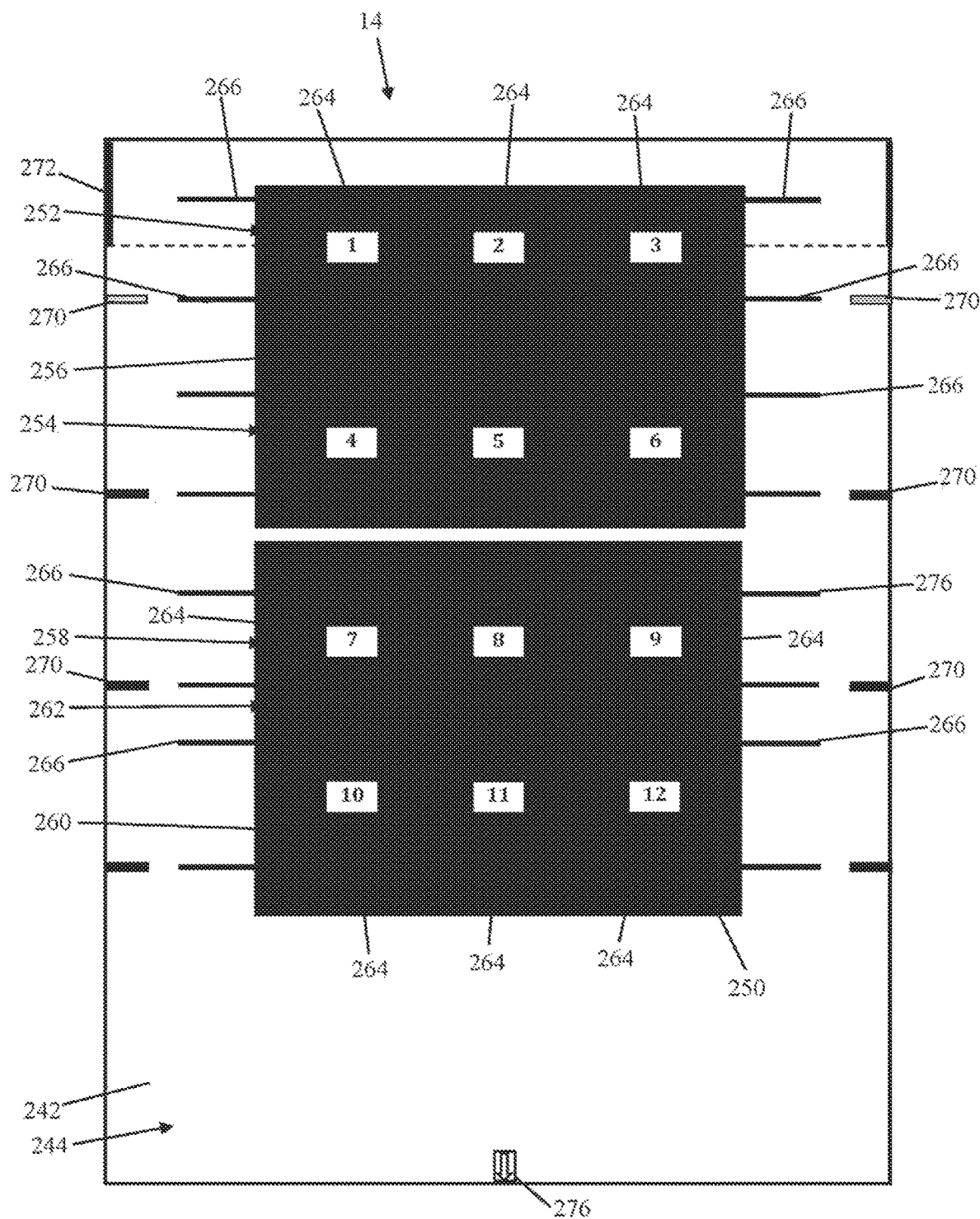
FIG. 32 is a front plan view of an example of a sterile identification barrier forming part of the surgical tray efficiency system of FIG. 1.
Figure 33:
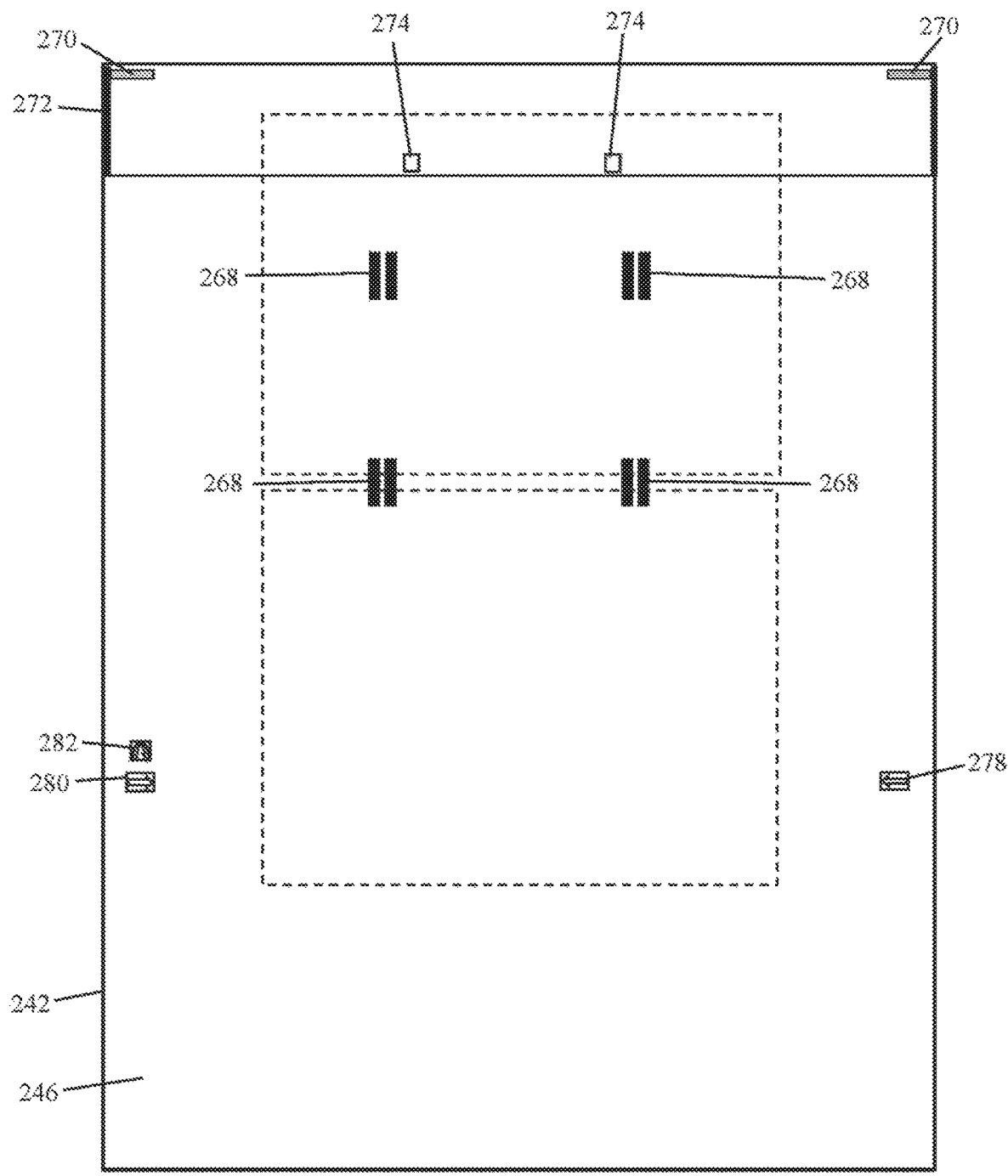
FIG. 33 is a rear plan view of the sterile identification barrier of FIG. 32.

FIGS. 32-33 illustrate one example of a sterile identification barrier 14 sized for use with a "triple-wide" vertical rack assembly 12 having four shelves. By way of example, the sterile identification barrier 14 comprises a large sheet 242 of sterile material (e.g. PE) sized and configured to overlay the vertical rack assembly 12. The sterile identification barrier 14 has an upper-facing surface 244 (FIG. 32) and a lower-facing surface 246 (FIG. 33). The upper facing surface 244 includes a plurality of thicker tray pads sized and configured for positioning within the various shelves of the vertical rack assembly 12 described above. The thicker tray pads are comprised of a resilient absorbent material (e.g. PSB 3030 with PE) to facilitate absorption of liquid as well as prevent perforation of the sterile identification barrier 14 due to contact with surgical instruments. The tray pads may be sized such that a single pad fits within a single shelf, or alternatively the tray pads may be sized such that a single pad covers more than one shelf. The sterile identification barrier 14 of the present example includes a first tray pad 248 and a second tray pad 250. The first tray pad 248 is positioned near one end of the large sheet 242 and is configured to cover the third and fourth shelves 34, 36 of the vertical rack assembly 12. The first tray pad 248 includes a first portion 252 sized and configured to rest within the fourth shelf 36, a second portion 254 sized and configured to rest within the third shelf 34, and a third portion 256 sized and configured to span the gap between the third and fourth shelves 34, 36. The second tray pad 250 is positioned adjacent to the first tray pad 248 and is sized and configured to cover the first and second shelves 30, 32 of the vertical rack assembly 12. The second tray pad 250 includes a first portion 258 sized and configured to rest within the second shelf 32, a second portion 260 sized and configured to rest within the first shelf 30, and a third portion 262 sized and configured to span the gap between the first and second shelves 30, 32.

The sterile identification barrier 14 includes a plurality of location indicia 264 that direct the user to a specific area to place the correct instrument tray so that the instrument tray is in the same location on vertical rack assembly 12 as it is in the planogram 444 (FIG. 59) on the standardization software platform 16. The exact number of location indicia 264 needed is determined by the size and number of shelves on the vertical rack assembly 12. For example, as noted previously the sterile identification barrier 14 of the instant example is configured for use with a "triple-wide" vertical rack assembly 12 having four shelves. Thus, the vertical rack assembly 12 is configured to hold a total of twelve instrument trays, and correspondingly the sterile identification barrier 14 for a "triple-wide" vertical rack assembly includes a total of twelve location indicia 264.

In the current example, the location indicia 264 that is located on the left side of the first portion 252 of the first tray pad 248 (from the perspective of a user looking at the vertical rack assembly 12 with sterile identification barrier 14 employed) has assigned a "1". Thus the identification label 264 includes the marking "1" and may be color-coded. From the user's perspective when looking at the vertical rack assembly 12 with a deployed sterile identification barrier 14, this "position 1" is located in the upper left position, which correspondingly is the same location of "position 1" on the planogram in the standardization software 16. The identification label 264 that is located generally in the center of the first portion 252 of the first tray pad 248 has been assigned to "position 2" and marked with a "2" identifier. The identification label 264 that is located generally on the right side (from the user's perspective looking at the sterile identification barrier 14) of the first portion 252 of the first tray pad 248 has been assigned to "position 3" and marked with a "3" identifier. In the same fashion, the second portion 254 of the first tray pad 248 includes three identification labels 264, one each marked with a "4", "5", and "6" identifier, the first portion 258 of the second tray pad 250 includes three identification labels 264, one each marked with a "7", "8", and "9" identifier, and the second portion 260 of the second tray pad 250 includes three identification labels 264, one each marked with a "10", "11", and "12" identifier.

The location indicia 264 may take any form that quickly and easily conveys information to a user, including but not limited to letters, numbers, symbols, shapes, colors, and/or words, alone or in combination. According to one example, different colors may be used to indicate which shelf a specific instrument is located on. For instance, the location indicia 264 positioned in the first portion 252 of the first tray pad 248 may be sequentially numbered 1, 2, 3 and may also be blue in color, while the location indicia 264 positioned within the second portion 254 of the first tray pad 248 may be sequentially numbered 4, 5, 6 and may also be red in color, and so on. In some instances, for example when multiple vertical rack assemblies 12 are in use for the same surgical procedure, a location indicia 264 may be a combination of numbers and letters (e.g. A1, A2, A3 . . . ) in addition to being color-coded as described above. By way of example only, the location indicia 264 on the sterile identification barrier 14 of the instant example comprise labels containing sequential numbers (e.g. 1, 2, 3 . . . 12). It is important for the correct tray to be associated with a specific identification label 264, so that the information is coordinated with preset planogram of the standardized software platform 16. To help ensure this outcome, matching location-indicia labels, tags or clips may be affixed to the instrument trays once a tray is assigned a location in the planogram 444 during initial setup (see, e.g. FIG. 36).

The sterile identification barrier 14 further includes a plurality of coated wires 266 mounted partially on the large sheet 242 and partially on portions of the tray pads 248, 250. The coated wires 266 can be manipulated in order to conform the sterile identification barrier 14 to vertical rack assembly 12 and secure the positioning of the tray pads 248, 250 and/or tray pad portions 252, 254, 258, 260 within the respective shelves 36, 34, 32, 30. More specifically, the coated wires 256 are bendable so that once a particular tray pad or tray pad portion is positioned within the correct shelf on the vertical rack assembly 12 (for example tray pad portion 252 positioned over fourth shelf 36) the group of four coated wires 264 immediately adjacent to the tray pad portion 252 (two coated wires 264 on each side of the tray pad portion) are bent around the lateral edge of the fourth shelf 36, thus securing that portion of the sterile identification barrier 16 to the vertical rack assembly 12.

The sterile identification barrier 14 may include additional anti-migration features 268 (e.g. hook-and-loop fasteners) positioned on the lower facing surface 246 that interact with corresponding anti-migration features (not shown) on the vertical rack assembly 12 to help prevent shifting of the sterile identification barrier 14 during use. Additionally, a plurality of adhesive strips 270 placed about the perimeter of the sterile identification barrier 14 on both the upper-facing surface 244 and lower-facing surface 246 may be used to reduce any stack that might occur when the sterile identification barrier 14 is employed on the vertical rack assembly 12. A portion of material at the top of the sterile identification barrier 14 is folded over and heat-sealed to create a cuff 272 that fits over the back of the vertical rack assembly 12. The sterile identification barrier 14 may further include additional visual indicators to help direct users in the proper way to unfold the sterile identification barrier 14. For example, a pair of visual indicators 274 (e.g. hand icons) may be positioned on the cuff 272 (on the lower-facing surface 246) to indicate to a user the proper spot for placement of hands during the unfolding process. Another visual indicator 276 (e.g. downward pointing arrow) may be positioned on the upper-facing surface 244 at the opposite end of the large sheet 242 from the cuff 272, indicating the direction in which the user must unfold that portion of the folded sterile identification barrier 14. Additional visual indicators 278 (right-pointing arrow), 280 (left-pointing arrow) and 282 (U-shaped arrow) are positioned on the lower-facing surface 246 and perform similar functions to that of the visual indicator 276.

Figure 34:
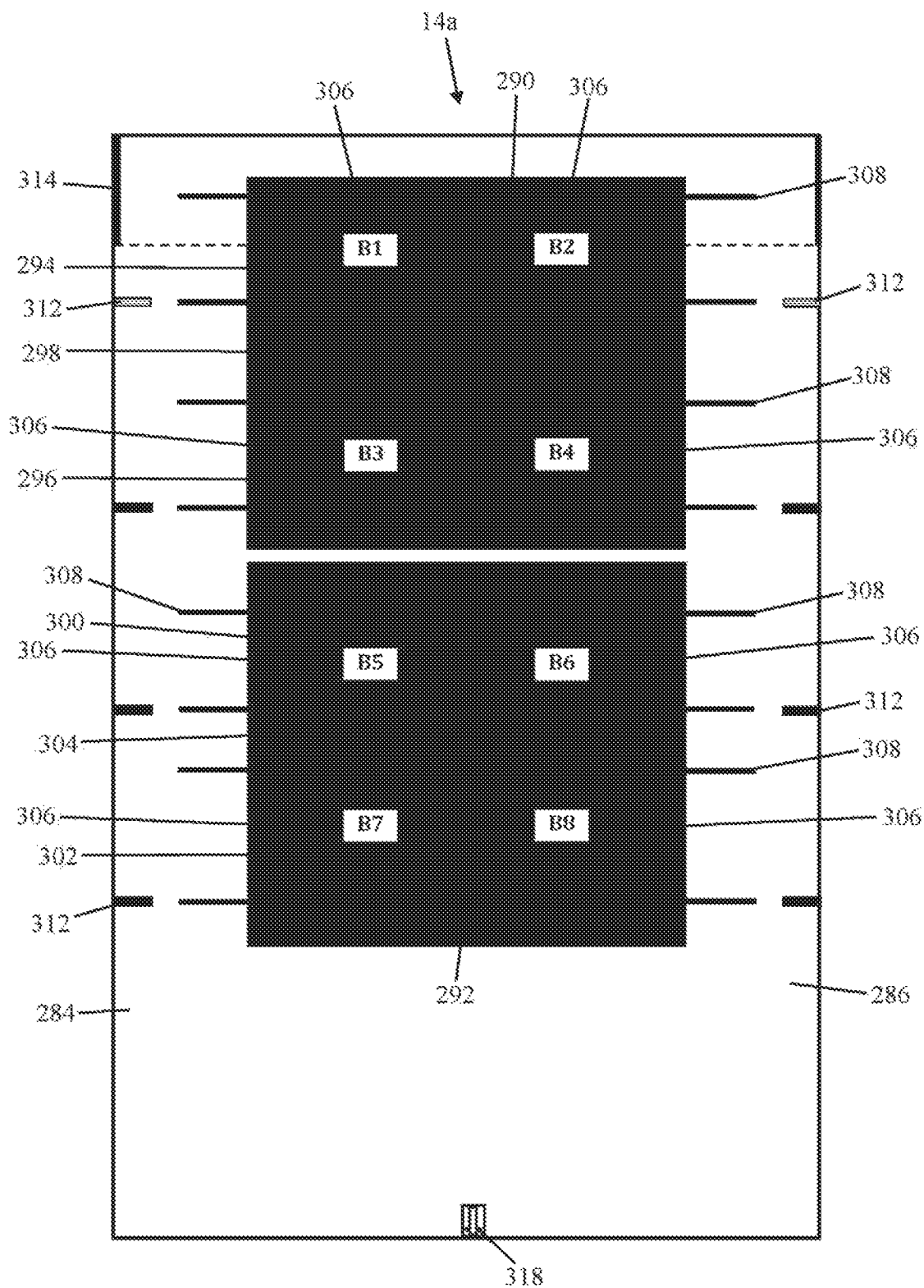
FIG. 34 is a front plan view of another example of a sterile identification barrier forming part of the surgical tray efficiency system of FIG. 1.
Figure 35:
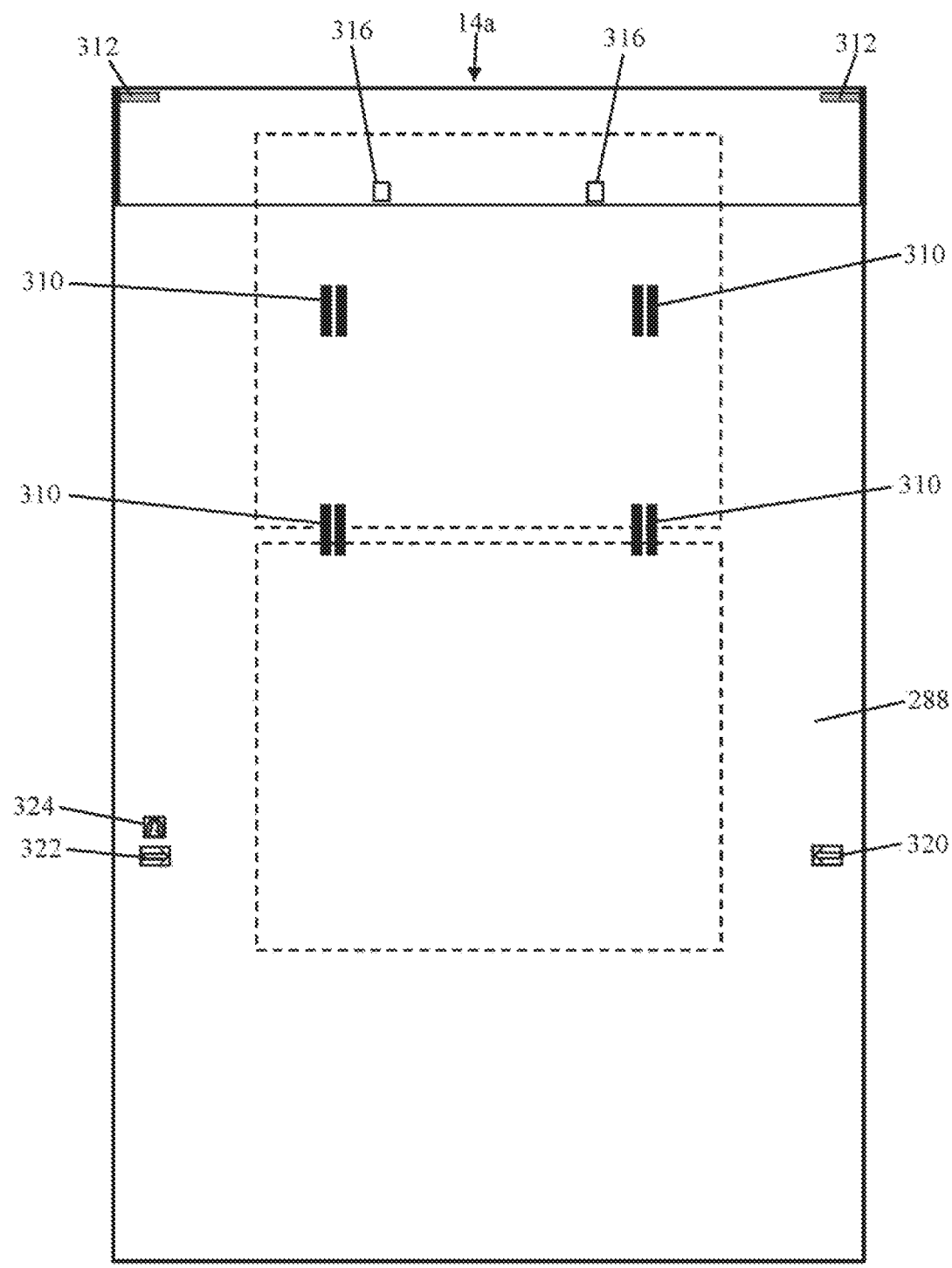
FIG. 35 is a rear plan view of the sterile identification barrier of FIG. 34.

FIGS. 34-35 illustrate an example of a sterile identification barrier 14a sized for use with a "double-wide" vertical rack assembly 12 having four shelves. The sterile identification barrier 14a of the instant example is virtually identical with respect to features and function as the sterile identification barrier 14 described above in relation to FIGS. 32-33 except that the overall size is smaller to accommodate a smaller "double-wide" vertical rack assembly 12 and the sterile identification barrier 14a of the instant example comprises a total of eight location indicia 306.

The sterile identification barrier 14a comprises a large sheet 284 of sterile material (e.g. PE) having an upper-facing surface 286 (FIG. 34) and a lower-facing surface 288 (FIG. 35). The upper facing surface 288 includes a plurality of thicker tray pads sized and configured for positioning within the various shelves of the vertical rack assembly 12 described above. The thicker tray pads are comprised of a resilient absorbent material (e.g. PSB 3030 with PE) to facilitate absorption of liquid as well as prevent perforation of the sterile identification barrier 14a due to contact with surgical instruments. The tray pads may be sized such that a single pad fits within a single shelf, or alternatively the tray pads may be sized such that a single pad covers more than one shelf. The sterile identification barrier 14a of the present example includes a first tray pad 290 and a second tray pad 292. The first tray pad 290 is positioned near one end of the large sheet 284 and is configured to cover the third and fourth shelves 34, 36 of the vertical rack assembly 12. The first tray pad 290 includes a first portion 294 sized and configured to rest within the fourth shelf 36, a second portion 296 sized and configured to rest within the third shelf 34, and a third portion 298 sized and configured to span the gap between the third and fourth shelves 34, 36. The second tray pad 292 is positioned adjacent to the first tray pad 290 and is sized and configured to cover the first and second shelves 30, 32 of the vertical rack assembly 12. The second tray pad 292 includes a first portion 300 sized and configured to rest within the second shelf 32, a second portion 302 sized and configured to rest within the first shelf 30, and a third portion 304 sized and configured to span the gap between the first and second shelves 30, 32.

As with the sterile identification barrier 14 described above, the sterile identification barrier 14a includes a plurality of location indicia 306 that direct the user to a specific area to place the correct instrument tray so that the instrument tray is in the same location on vertical rack assembly 12 as it is in the planogram 444 on the standardization software platform 16. The location indicia 306 may take any form that quickly and easily conveys information to a user, including but not limited to letters, numbers, symbols, shapes, colors, and/or words, alone or in combination. The sterile identification barrier 14a shown by way of example in FIG. 34 includes alphanumeric location indicia 306 to create differentiation in a case where there are multiple vertical rack assembly 12 units in the same operating room. For example, the location indicia 306 of the instant example are labeled "B1, B2, B3 . . . B8" to differentiate from another vertical rack assembly 12 in the room (which may be labeled "A1, A2, A3 . . . A12" for example).

As with the sterile identification barrier 14, the sterile identification barrier 14a further includes a plurality of coated wires 308 mounted partially on the large sheet 284 and partially on portions of the tray pads 290, 292. The coated wires 308 can be manipulated in order to conform the sterile identification barrier 14a to vertical rack assembly 12 and secure the positioning of the tray pads 290, 292 and/or tray pad portions 294, 296, 300, 302 within the respective shelves 36, 34, 32, 30 in the manner described above. The sterile identification barrier 14a may also include additional anti-migration features 310 (e.g. hook-and-loop fasteners) positioned on the lower facing surface 288 that interact with corresponding anti-migration features (not shown) on the vertical rack assembly 12 to help prevent shifting of the sterile identification barrier 14a during use. Additionally, a plurality of adhesive strips 312 placed about the perimeter of the sterile identification barrier 14a on both the upper-facing surface 286 and lower-facing surface 288 may be used to reduce any stack that might occur when the sterile identification barrier 14a is employed on the vertical rack assembly 12. A portion of material at the top of the sterile identification barrier 14a is folded over and heat-sealed to create a cuff 314 that fits over the back of the vertical rack assembly 12. The sterile identification barrier 14a may further include additional visual indicators to help direct users in the proper way to unfold the sterile identification barrier 14a. For example, a pair of visual indicators 316 (e.g. hand icons) may be positioned on the cuff 314 (on the lower-facing surface 288) to indicate to a user the proper spot for placement of hands during the unfolding process. Another visual indicator 318 (e.g. downward pointing arrow) may be positioned on the upper-facing surface 286 at the opposite end of the large sheet 284 from the cuff 314, indicating the direction in which the user must unfold that portion of the folded sterile identification barrier 14a. Additional visual indicators 320 (right-pointing arrow), 324 (left-pointing arrow) and 326 (U-shaped arrow) are positioned on the lower-facing surface 288 and perform similar functions to that of the visual indicator 318.

Figure 36:
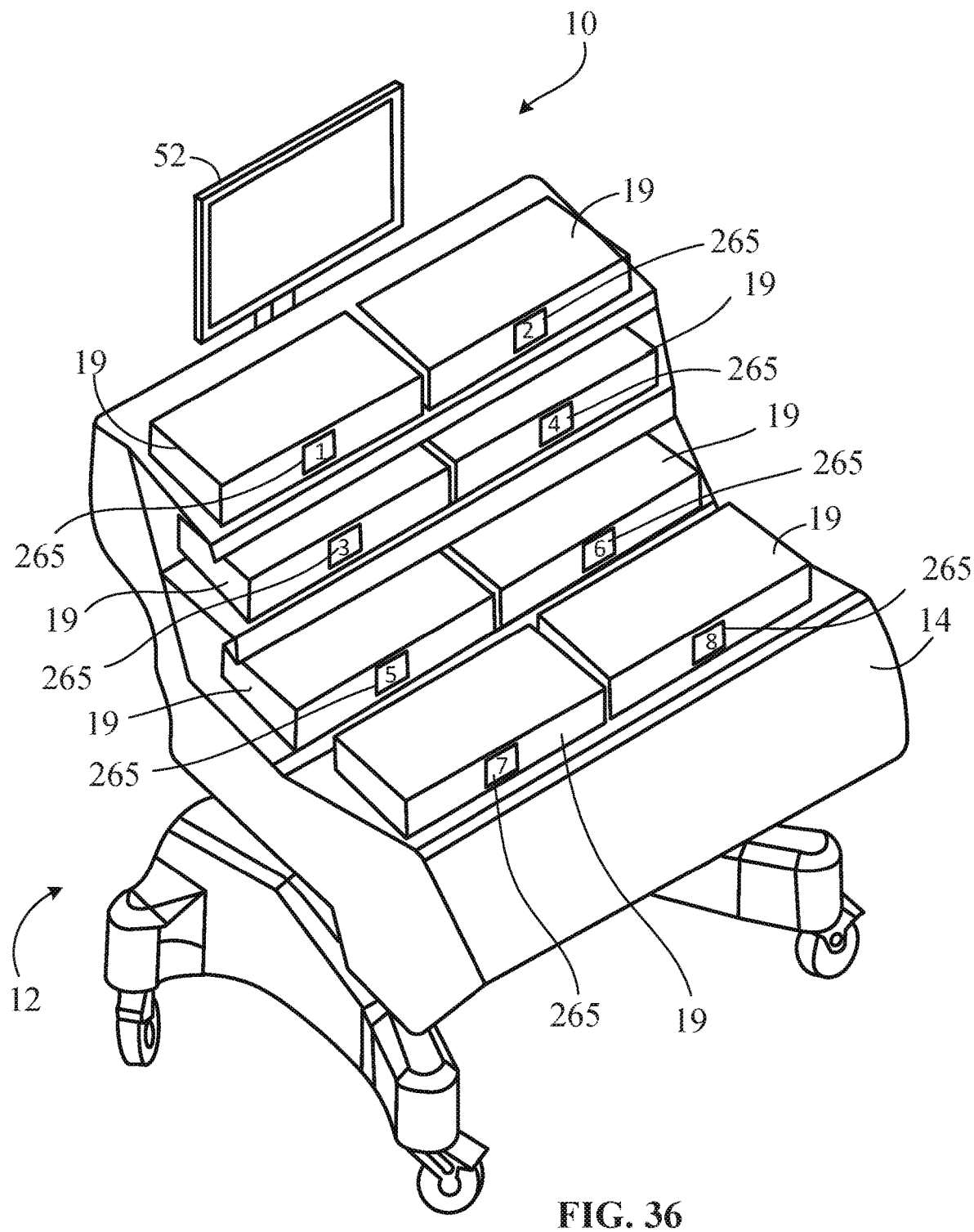
FIG. 36 is a perspective view of the vertical rack assembly of FIG. 2 combined with the sterile identification barrier of FIG. 34 and an associated plurality of surgical instrument trays.

FIG. 36 illustrates an example of a vertical rack assembly 12 having a sterile identification barrier 14 and a plurality of surgical instrument trays 19 deployed thereon. The vertical rack assembly 12 is a "double-wide" rack, where each shelf can hold at least two instrument trays 19. The instrument trays 19 of the instant example each include location indicia labels 265 affixed thereto that correspond with the location indicia of the sterile identification barrier 14 and the assigned location in the planogram. The location indicia 265 of the instant example comprise labels including sequential numbers (e.g. 1, 2, 3 . . . 8). It is important for the correct tray to be associated with a specific identification label 265, so that the information is coordinated with preset planogram of the standardized software platform 16.

Figure 37:
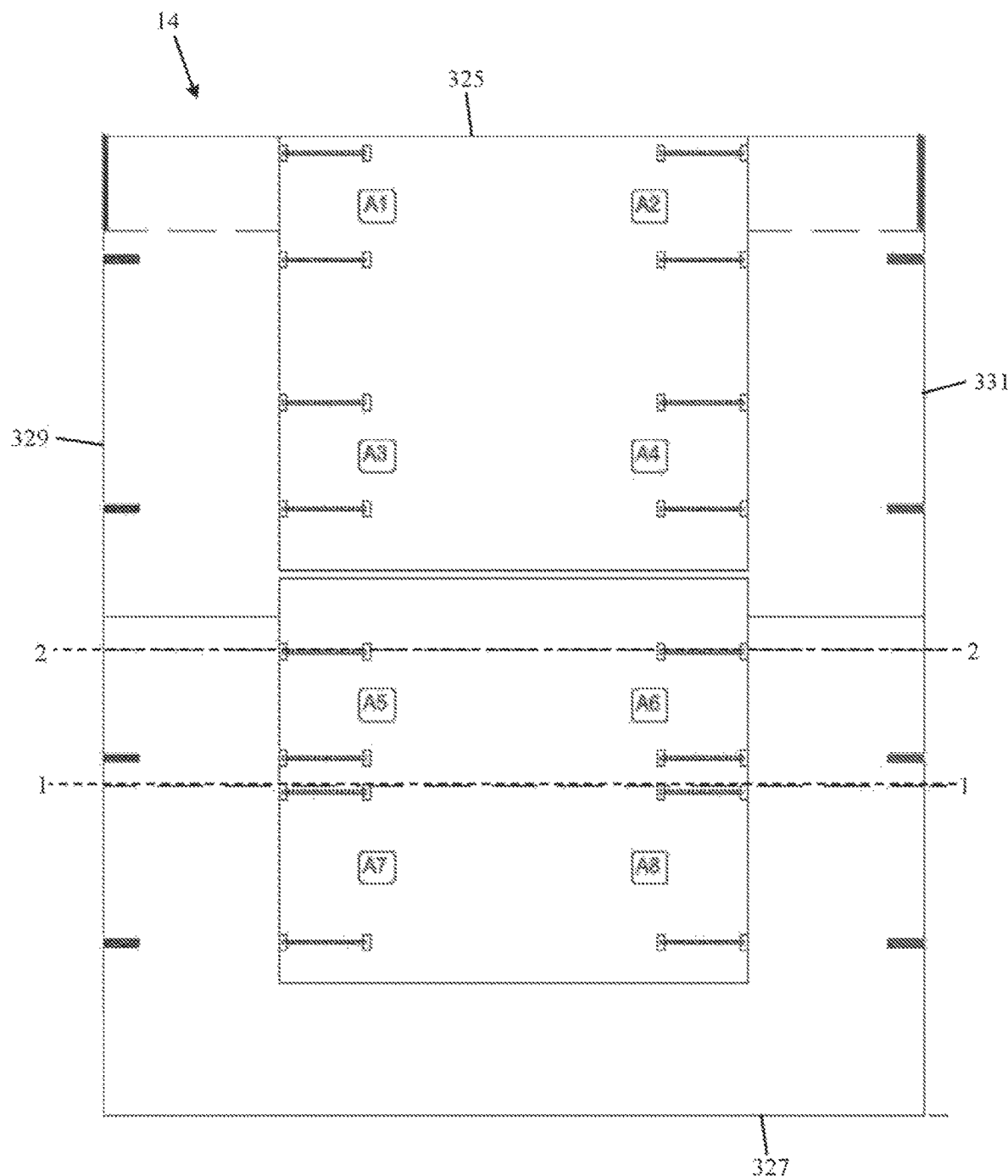
FIGS. 37-44 are perspective views of the sterile identification barrier of FIG. 34, illustrating a sequence of folding the sterile identification barrier.

FIGS. 37-50 illustrate the sequence of folding an example sterile identification barrier 14 (and/or 14a) so that the process of unfolding and draping a vertical rack assembly 12 does not break the sterile protocol or risk any contamination before, during and after a surgical procedure. The folding process includes a total of twenty specific folds $F_1$-$F_{20}$ in made in sequential order. FIG. 37 depicts one example of a sterile identification barrier 14 having a front-facing surface 286, a back-facing surface 288, a top edge 325, bottom edge 327, left edge 329, and right edge 331 laying flat and ready to be folded. The first fold $F_1$ is made by folding the bottom edge 327 back over the sterile identification barrier 14 along line 1-1. The second fold $F_2$ is made by folding the first fold $F_1$ back under the sterile identification barrier 14 along line 2-2.

Figure 38:
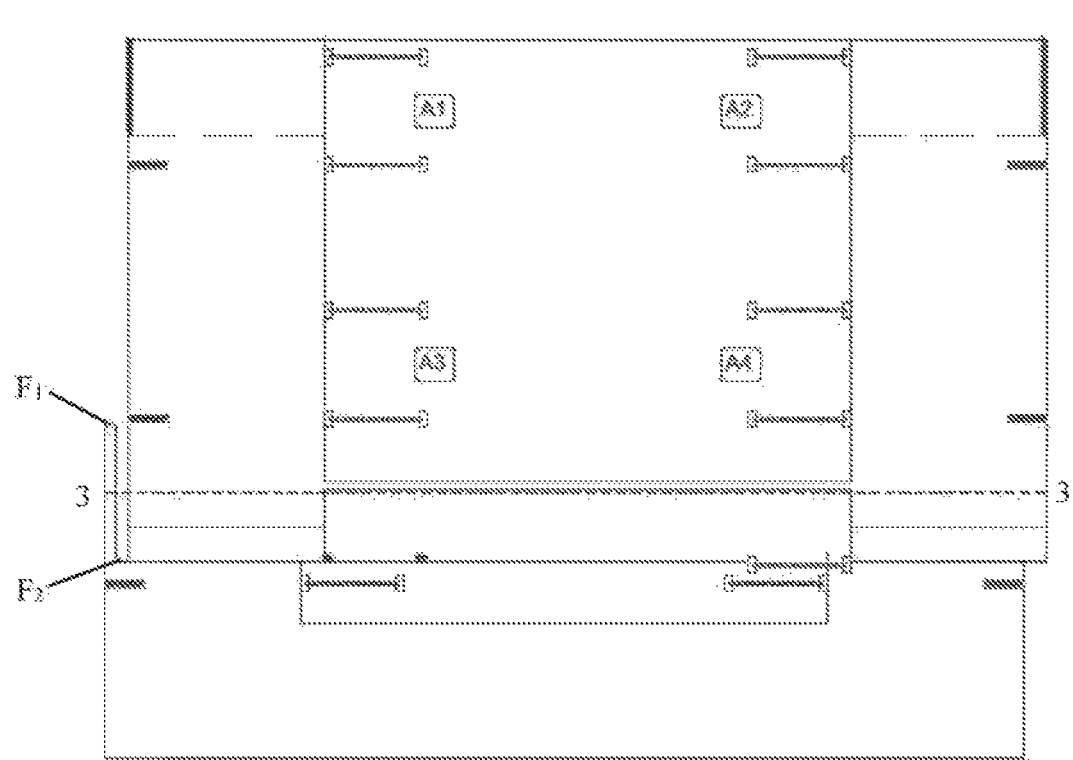
Figure 39:
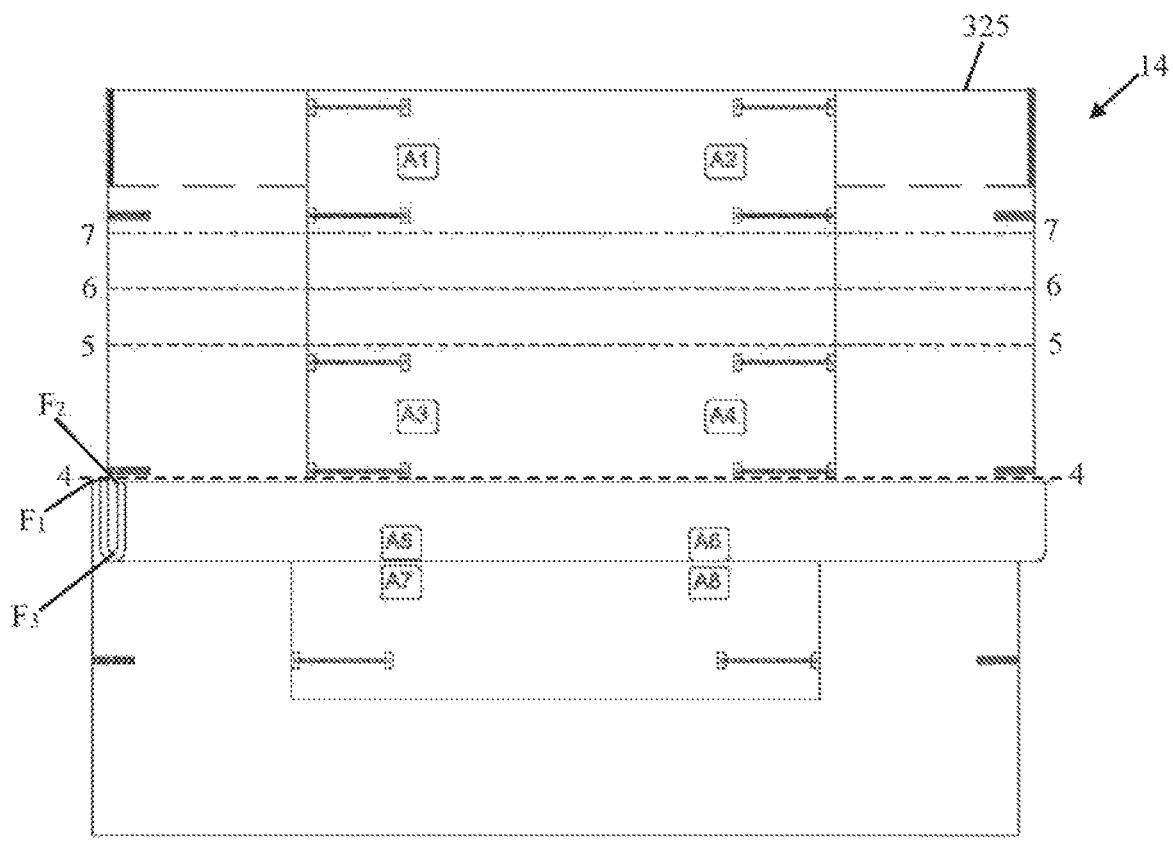

FIG. 38 depicts the example sterile identification barrier 14 after the first and second folds $F_1$, $F_2$ have been made. The third fold is made by folding the second fold $F_2$ up over line 3-3. FIG. 39 depicts the example sterile identification barrier 14 after the third fold $F_3$ has been made. The fourth fold $F_4$ is made by folding the top edge 325 back over the now folded stack along the line 4-4. The fifth fold $F_5$ is made by folding the top edge 325 back over the folded stack along the line 5-5. The sixth fold $F_6$ is made by folding the top edge 325 back over the folded stack along the line 6-6. The seventh fold $F_7$ is made by folding the top edge 325 back over the folded stack along the line 7-7.

Figure 40:
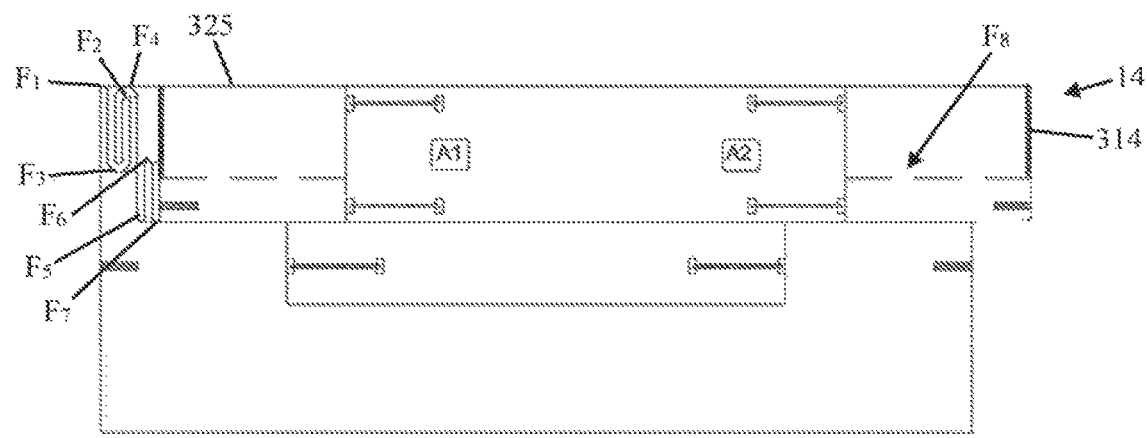
Figure 41:
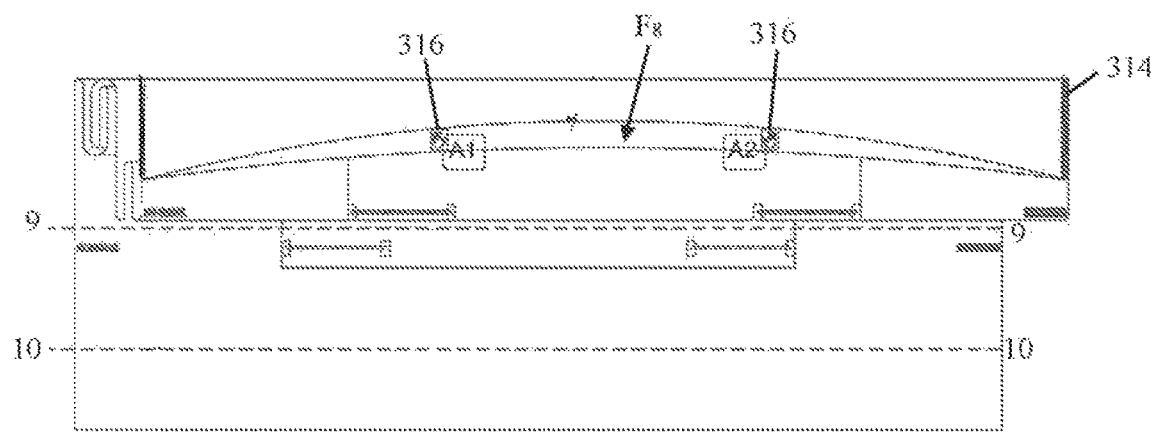

FIG. 40 depicts the example sterile identification barrier 14 after the seventh fold $F_7$ has been made. As depicted in the drawing (which is not necessarily to scale), at this point the top edge 325 of the sterile identification barrier 14 is even with the first fold $F_1$ and fourth fold $F_4$. The eighth fold $F_8$ is made by folding the cuff 314 inside out and then flipping the front edge of the cuff 314 up to reveal visual indicators 316 (e.g. hand prints icons) that communicate to the user where to place their hands when unfolding the sterile identification barrier 14. The partially folded sterile identification barrier 14 now should appear as depicted in FIG. 41. The ninth fold $F_9$ is made by folding the bottom edge 327 up and over the entire stack along the line 9-9 so that the portion that was just folded is on top of the stack. The tenth fold $F_{10}$ is made by folding the bottom edge 327 back over the top of the stack along line 10-10 so that visual indicator 318 (e.g. downward pointing arrow) is visible on the top of the folded stack.

Figure 42:
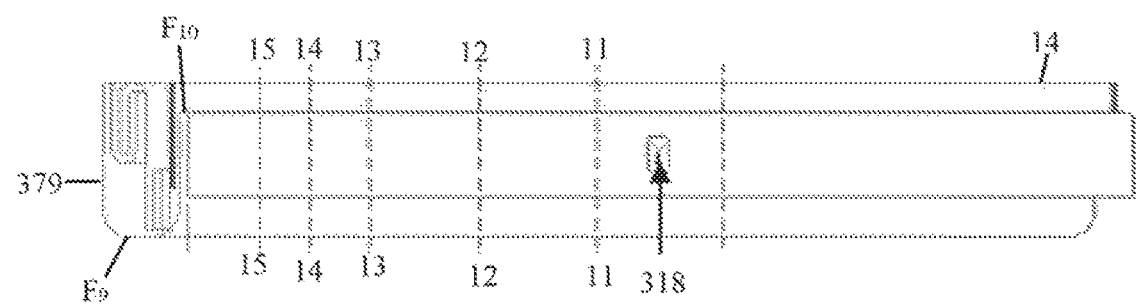

At this point in the folding process, the semi-folded sterile identification barrier 14 should look as depicted in FIG. 42, which also shows the folding lines for the next group of folds. The eleventh fold $F_{11}$ is made by folding the left edge 379 back over the top of the stack (to the right) along line 11-11. The twelfth fold $F_{12}$ is made by folding the left edge 379 back over the top of the stack (to the left) along line 12-12. The thirteenth fold $F_{13}$ is made by folding the left edge 379 back over the top of the stack (to the right) along line 13-13. The fourteenth fold $F_{14}$ is made by folding the left edge 379 back over the top of the stack (to the left) along line 14-14. The fifteenth fold $F_{15}$ is made by folding the left edge 379 back over the top of the stack (to the right) along line 15-15 so that the visual indicator 320 (e.g. left facing arrow) is on the top of the folded stack.

Figure 43:
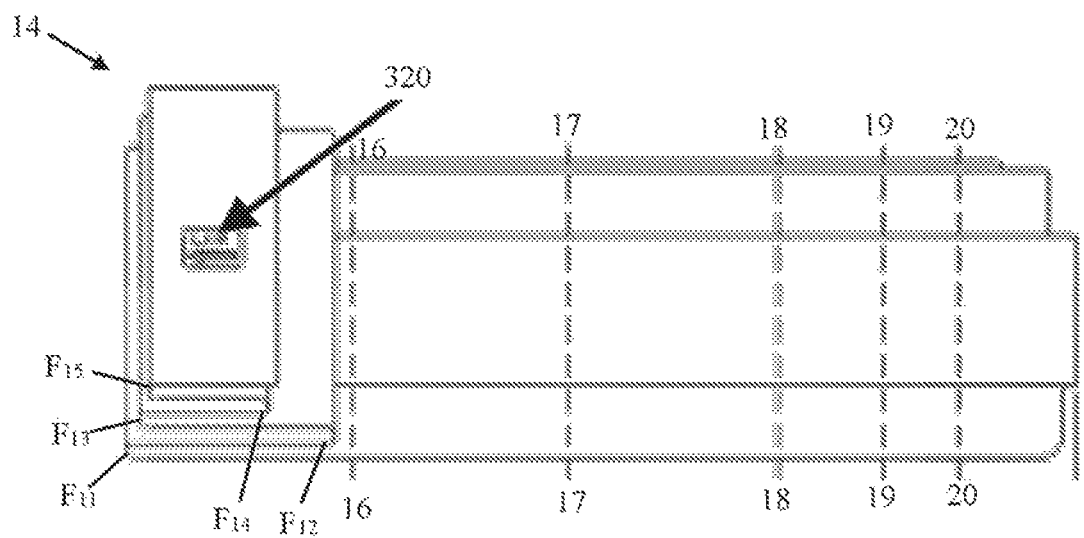
Figure 44:
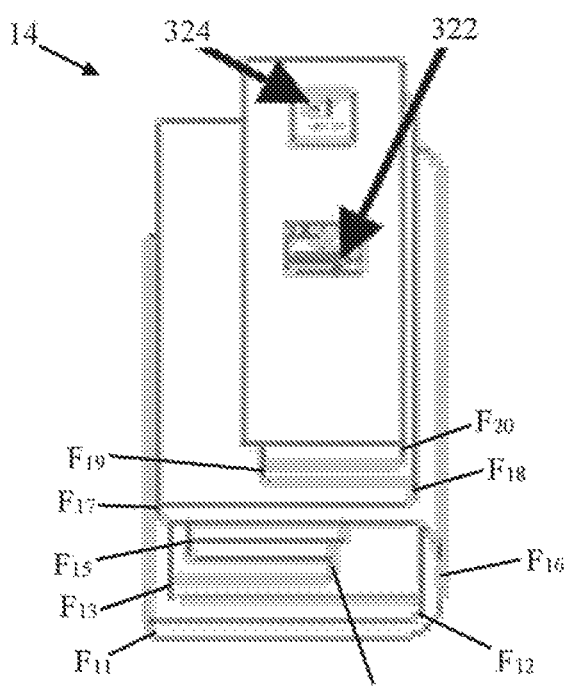
Figure 45:
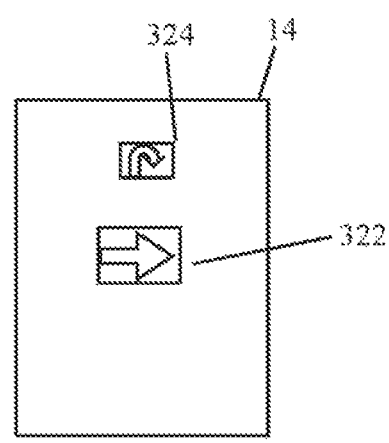
FIGS. 45-50 illustrate an example of a sequence of folding the folded sterile identification barrier of FIG. 44 within an outer wrap.
Figure 46:
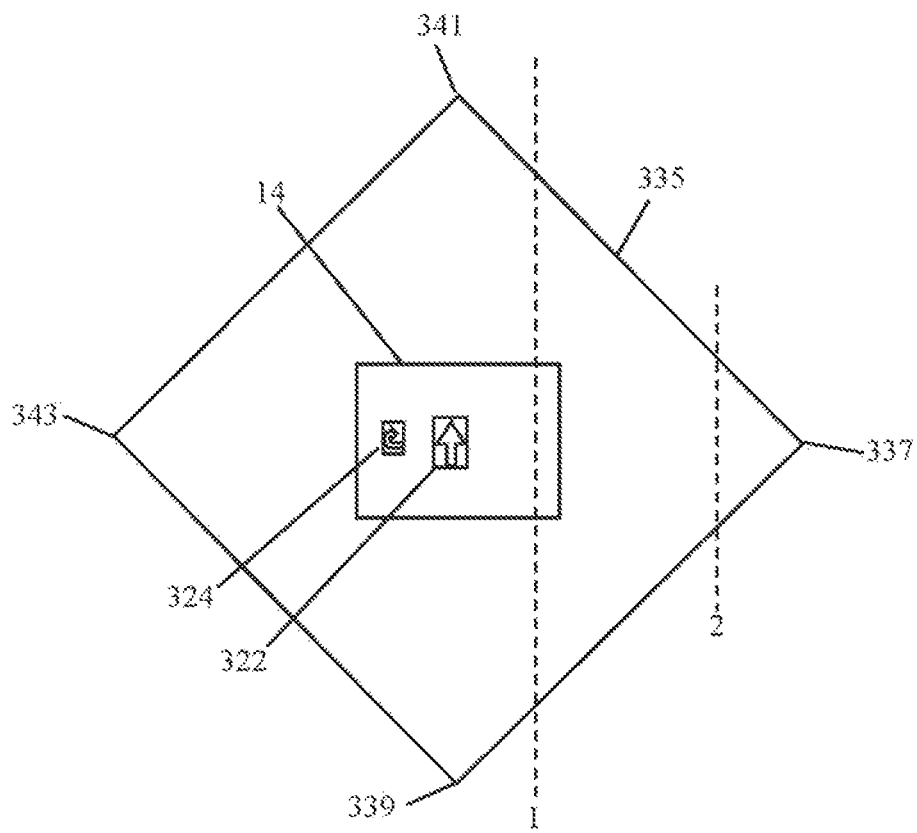
Figure 47:
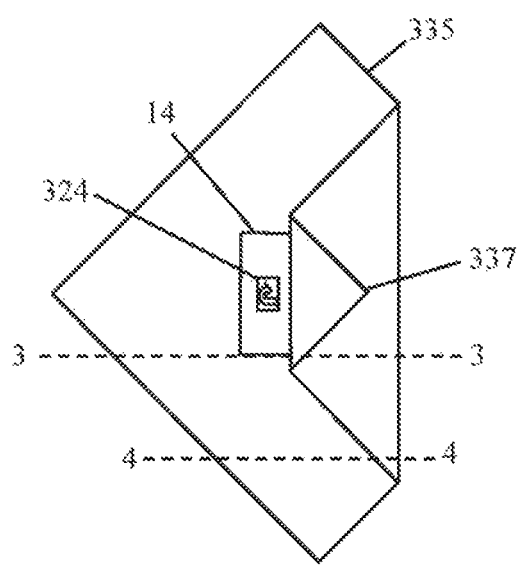
Figure 48:
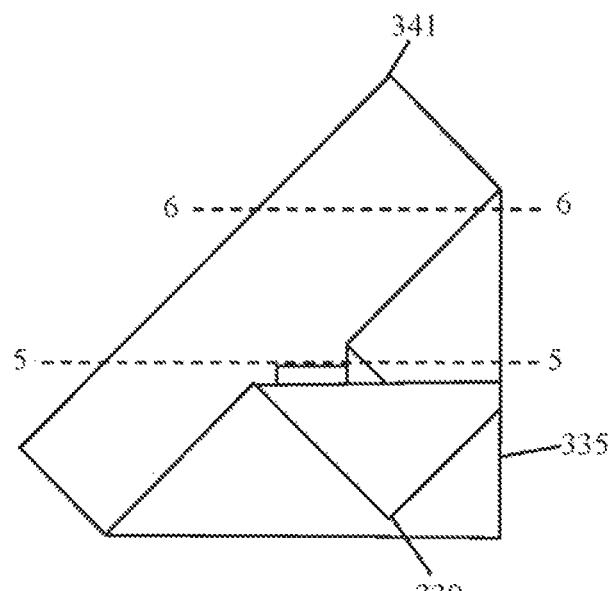
Figure 49:
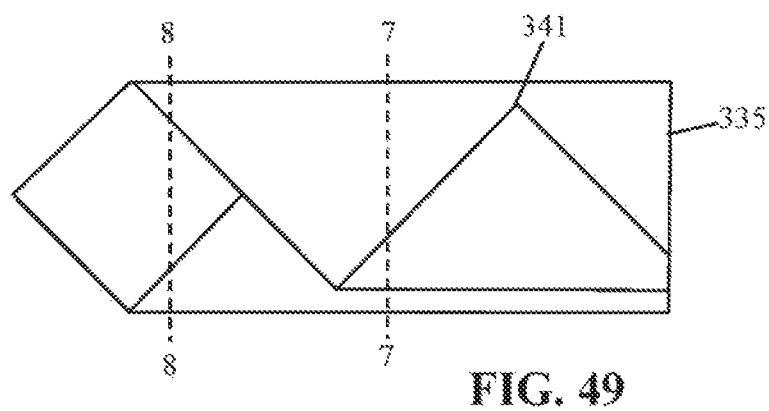

At this point in the folding process the semi-folded sterile identification barrier 14 should look as depicted in FIG. 43, which also shows the folding for the last group of folds. The sixteenth fold $F_{16}$ is made by folding the right edge 331 back over the top of the stack (to the left) along line 16-16. The seventeenth fold $F_{17}$ is made by folding the right edge 331 back over the top of the stack (to the right) along line 17-17. The eighteenth fold $F_{18}$ is made by folding the right edge 331 back over the top of the stack (to the left) along line 18-18. The nineteenth fold $F_{19}$ is made by folding the right edge 331 back over the top of the stack (to the right) along line 19-19. The twentieth fold $F_{20}$ is made by folding the right edge 331 back over the top of the stack (to the left) along line 20-20 so that the visual indicator 322 (e.g. left facing arrow) and the visual indicator 324 (U-shaped arrow) are on the top of the folded stack, as shown in FIGS. 44-45.

FIGS. 46-50 illustrate an example of a process of folding an outer wrap 335 around the folded sterile identification barrier 14. By way of example, the outer wrap may be square-shaped with each side being approximately 100 cm in length. However other sizes are possible. To set up the outer wrap 335 and folded sterile identification barrier 14 for folding, the outer wrap 335 is first arranged in a diamond shape with the folded sterile identification barrier 14 placed horizontally in the center of the diamond shape with the visual indicator 322 (e.g. arrow) pointed up. The outer wrap 335 has a first corner 337 positioned to the right of the sterile identification barrier 14 in the instant example, a second corner 339 positioned below the sterile identification barrier 14, a third corner 341 opposite the second corner 339, and a fourth corner 343 opposite the first corner 337.

Figure 50:
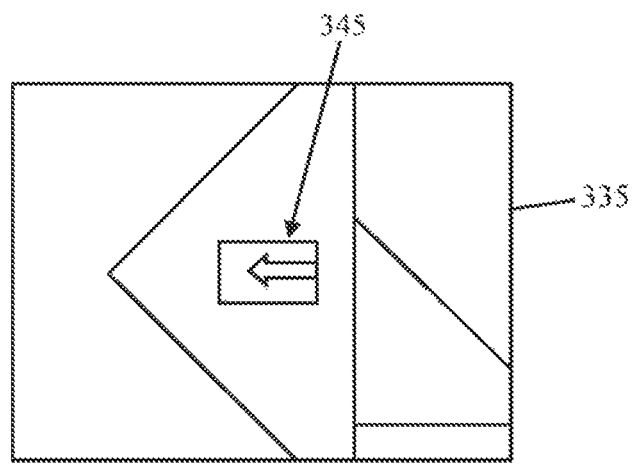

By way of example, the first group of folds may be made by folding the first corner 337 toward the sterile ID barrier 14 along line 1-1 and then folding the first corner 337 away from the sterile ID barrier 14 along line 2-2. The next group of folds may be made by folding the second corner 339 toward the sterile ID barrier 14 along line 3-3 in FIG. 47 and then folding the second corner 339 away from the sterile ID barrier 14 along line 4-4. The next group of folds may be made by folding the third corner 341 toward the sterile ID barrier 14 along line 5-5 in FIG. 48 and then folding the third corner 341 away from the sterile ID barrier 14 along line 6-6. The last group of folds may be made by folding the fourth corner 343 toward the sterile ID barrier 14 along line 7-7 in FIG. 49 and then folding the fourth corner 343 away from the sterile ID barrier 14 along line 8-8. The end result is an outer wrap 335 folded about the sterile identification barrier 14 as depicted in FIG. 50. When folded correctly, a visual indicator 345 (e.g. arrow) shows on top of the stack.

Figure 51:
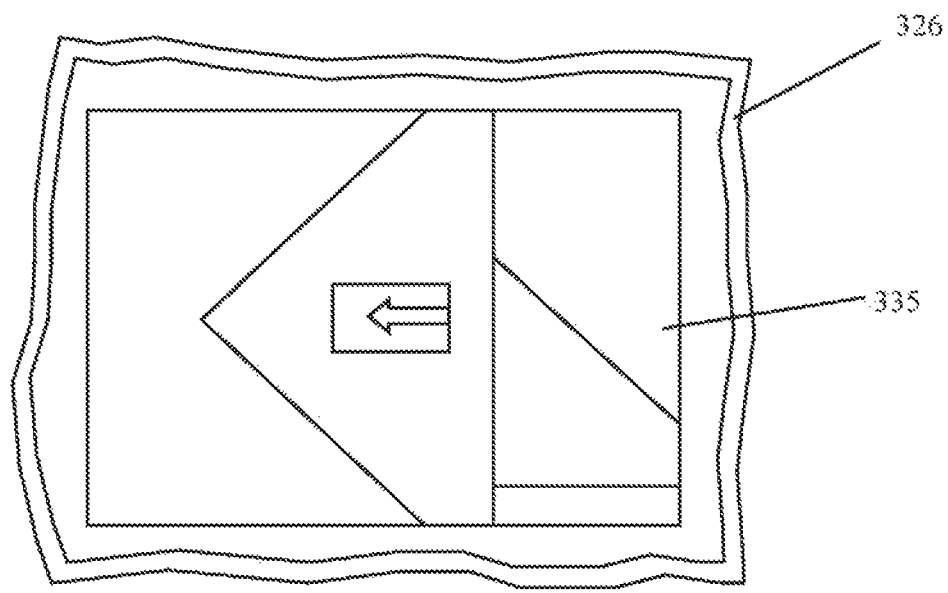
FIG. 51 is a perspective view of a folded sterilization barrier and outer wrap combination sealed within packaging.

FIG. 51 shows a folded sterile identification barrier 14 wrapped within an outer wrap 335 and sealed within a sterile package 326. To secure the sterile identification barrier 14 to the vertical rack assembly 12 (e.g the "draping" process), the above steps are essentially performed in the reverse order. By way of example, draping requires two users to complete, for example a circulating nurse and a scrub tech working in cooperation. As a first step, one person (e.g. circulating nurse) opens the sterile packaging, and centers the folded sterile identification barrier 14 (in the outer wrap 335) on the first shelf 30 with the arrow pointing away from them. Next the outer wrap 335 is unfolded. At this point, the folded sterile identification barrier 14 is exposed. The same person grabs the visual indicator 322 (e.g. right-facing arrow) and unfolds the sterile identification barrier 14 over the side of the vertical rack assembly 12. The other person (e.g. scrub tech) the grabs the visual indicator 320 (e.g. left-facing arrow) and unfolds the sterile identification barrier 14 over the opposite side of the vertical rack assembly 12. One person (e.g. circulating nurse) the grabs the sterile identification barrier 14 on both sides of the visual indicator 318 (e.g. downward arrow), and pulls it down over the front of the vertical rack assembly 12. The other person (e.g. scrub tech) secures the sterile identification barrier 14 by folding the coated wires 308 around the edges of the vertical rack assembly 12. The same person places their hands underneath the cuff 314, directly beneath the visual indicators 316 (e.g. hand prints), and lifts the sterile identification barrier 14 up and over the vertical rack assembly 12. The sterile identification barrier 14 is secured to the top level (e.g. fourth shelf 36) of the vertical rack assembly 12 using the coated wires 308. Next, the coated wires 308 are secured on the next level down (e.g. third shelf 34), as are the hook and loop fasteners 310 connecting the sterile identification barrier 14 to the vertical rack assembly. This process is repeated for all of the levels of the vertical rack assembly 12 until finished. The vertical rack assembly 12 is now ready to be set up with instrument trays according to the preselected planogram arrangement.

Figure 52:
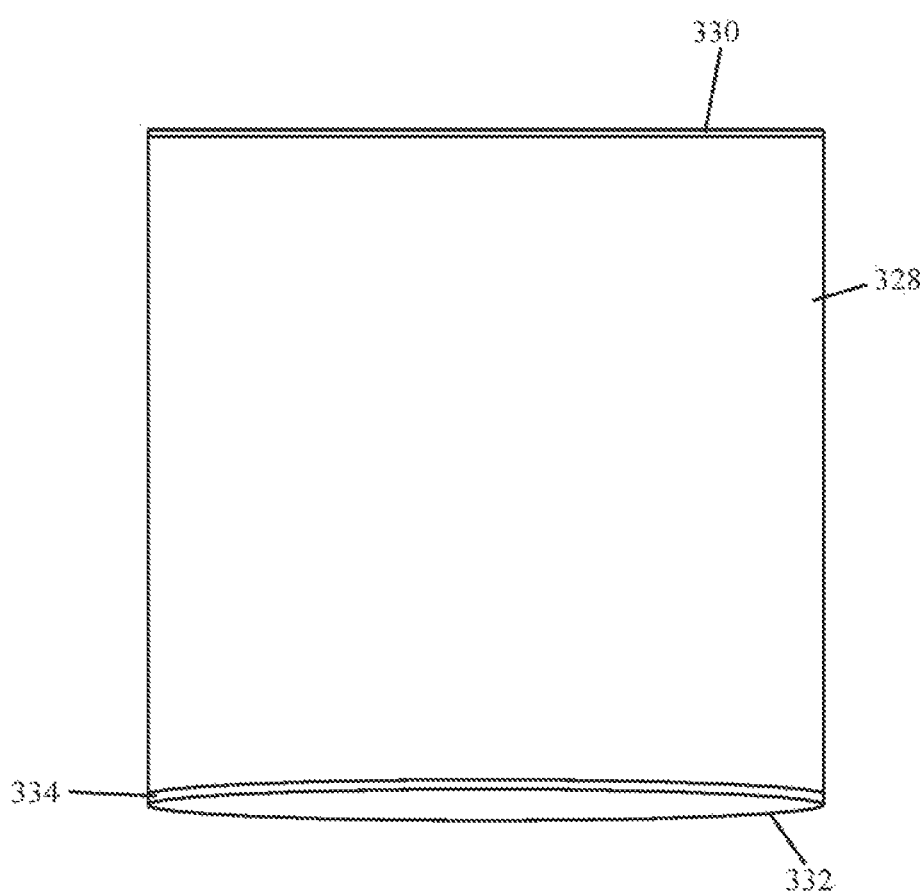
FIG. 52 is a perspective view of a monitor cover suitable for use with the surgical tray efficiency system of FIG. 1.

FIG. 52 displays a sterile monitor cover 328 sized and proportioned to fit over the monitor assembly 22 and extend downward past the upper most plane of vertical rack assembly 12. The sterile monitor cover 328 is manufactured from a single piece of clear material to maintain visibility of the monitor 52 when draped. The top edge 330 is heat sealed to create an enclosed bag with the bottom edge 332 having an elastic band 334 that cinches around the monitor assembly 22. The sterile monitor cover 328 may be stand-alone or alternatively may be attached or integrally formed with the sterile identification barrier 14. A smaller version of the sterile monitor cover 328 may be provided as a cover for the portable electronic device 17 (e.g. tablet computer, smart phone, etc) that is used to interface with the standardization software platform 16.

Figure 53:
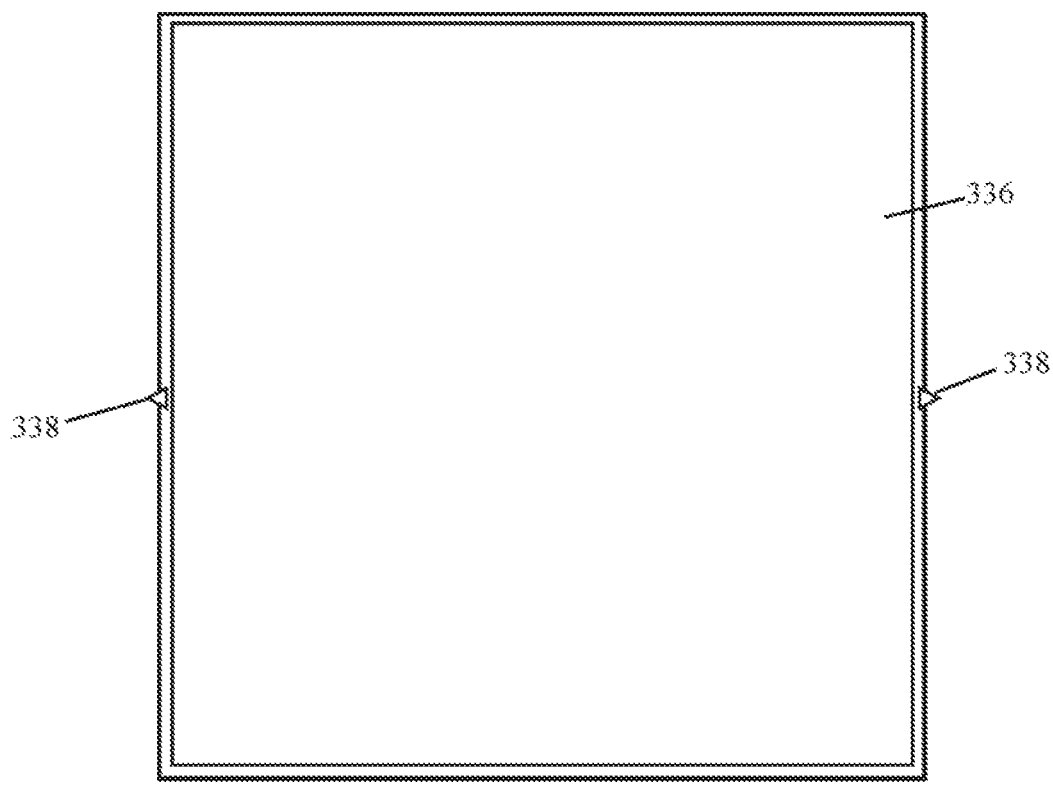
FIG. 53 is a plan view of a rack cover suitable for use with the surgical tray efficiency system of FIG. 1.

FIG. 53 illustrates a sterile clear cover 336 that can be used to cover a vertical rack assembly 12 and sterile identification barrier 14 when it is loaded with surgical instrument trays. The sterile clear cover 336 allows a user to maximize the sterility of instrumentation that may not be needed during the first portion of a surgical procedure. An attachment device such as but not limited to adhesive strips, Velcro or a draw string 338 around the perimeter of the sterile clear cover 336 helps to conform and maintain the correct position on the vertical rack assembly 12 until the user needs to remove the sterile clear cover 336 and use the surgical instruments that have maintained maximum sterility. By way of example, the sterile clear cover 336 may be employed for pre-setup racks that may be simply rolled into the operating room ready to use as soon as the disposable cover 336 is removed.

The surgical tray efficiency system 10 described herein is an integrated workflow management system designed to help perioperative staff standardize and improve their processes. While the efficiency gains manifest themselves during the surgical procedure, the groundwork is laid during the setup process. The setup process has two main goals: first, to ensure that all instruments needed for the surgery are present and accounted for, and second, to arrange the various instrument trays according to the planogram functionality such that their location is appropriate and optimized for all stakeholders.

Figure 54:
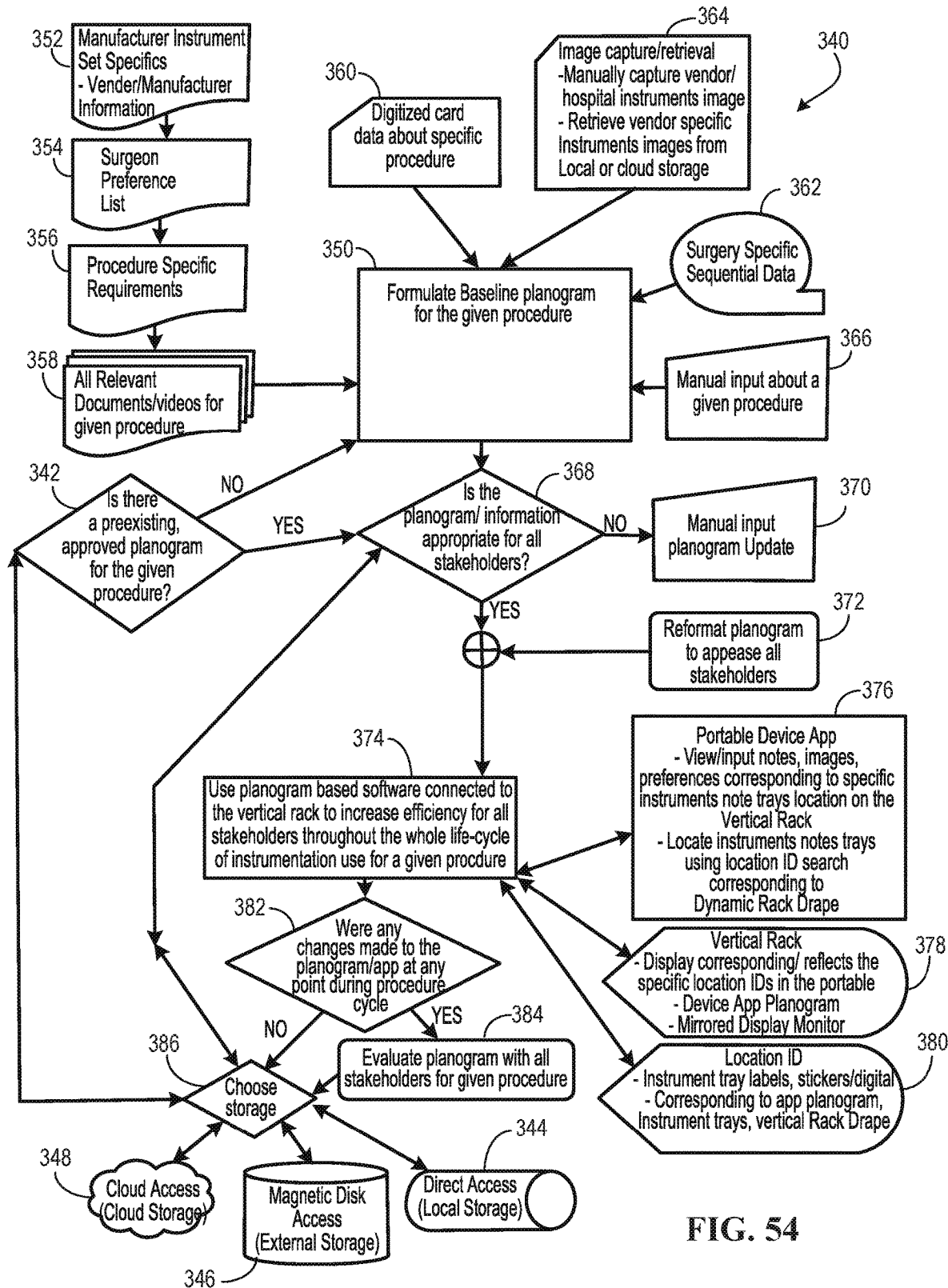
FIG. 54 is a flowchart depicting the framework and logic flow of the standardization software platform forming part of the surgical tray efficiency system of FIG. 1.

FIG. 54 depicts a flowchart 340 that lays out the framework and logic flow of the standardization software platform 16. The flowchart describes how data is input, used, changed and stored for a given surgical procedure. A goal of the standardization software platform 16 is to increase efficiency in the operating room environment by creating and employing a planogram for a given procedure that can be customized to suit a particular surgeon's needs and stored for future use. As used in this disclosure, a "planogram" is an interactive digital display of representations of surgical instrument trays arranged on a vertical rack assembly 12 for a given procedure, that also provides additional relevant information pertaining to the various instruments in each tray.

Initially, a user will engage the standardization software platform 16 to determine whether there is a pre-existing, approved planogram for a given procedure (342) that is accessible from direct access local storage 344 (e.g., memory that is contained within the computing system that includes the display), external storage 346 (e.g. magnetic disk or non-volatile memory), or cloud storage 348 (e.g., at one or more remote computing systems). If the answer is "no", then the user must formulate a baseline planogram for the given procedure (350). This includes digitally arranging the instruments and/or trays on a user interface using location ID (e.g. tray tags, stickers, digital location, and the like), creating and/or retrieving support media that pertain to specific instruments, sets, trays, or surgeons (e.g. videos, surgical techniques, marketing material, etc), and creating and/or retrieving notes that pertain to specific instruments, sets, trays, and/or surgeons. To create this initial formulation, the user can access materials/data from a variety of sources. Examples of data that might be "backend" available (e.g. preloaded or available for download via the Internet) include manufacturer instrument set specifics 352, surgeon preference lists 354, procedure-specific requirements 356, and other relevant documents/videos for a given procedure 358. The user can also import digitized card data about the specific procedure 360 and/or surgery specific sequential data 362 into the planogram. Another building block of the baseline planogram is the capture and/or retrieval of images (364). An important aspect of the planogram is the use of images to give a user a near-instant visual recognition of an instrument. The planogram can be loaded with any image the user might find useful, including but not limited to entire instrument trays, specific isolated instruments, and the like. Notably, the user is able to use the portable computer device's camera to manually capture images in addition to retrieving vendor specific images from local or cloud storage. The user may also manually input any other useful information about a given procedure into the planogram (366).

After initial setup of the planogram occurs, or if the answer to the initial question of whether there is a preexisting approved planogram (342) is "yes", the planogram is reviewed to determine whether the planogram is appropriate for all stakeholders (360). "Stakeholders" in this instance may include the specific doctor, hospital, and operating room technicians (including so-called "scrub-techs") that may be using the planogram software during the surgery. If the planogram is determined to be inadequate for any of the stakeholders, then the user may manually input a planogram update (370) and/or reformat the planogram to appease all stakeholders (372). "Appropriate" means acceptable and/or optimized for any of the various stakeholders, including most notably the surgeon(s) responsible for performing the surgery and the OR scrub technician(s) responsible for locating and handing the various surgical instruments (and implants, if applicable) to the surgeon(s) during the actual surgery. These steps may include (but are not limited to) changing the location of instrument trays, changing the accessible data regarding instruments or trays, updating additional notes pertaining to the surgery, etc.

Once the planogram is appropriate for all the stakeholders, the next step (374) is to use the planogram based software 16 connected to the vertical rack assembly 12 to increase efficiency for all stakeholders throughout the lifecycle of instrumentation use for a given procedure. This involves using the app on the portable device (376), the vertical rack (378), and the location ID (380). More specifically, the portable device app 376 is used interactively during the course of the surgical procedure to view and/or input notes, videos, images, and/or preferences corresponding to specific instruments, sets, trays, and/or locations on the vertical rack 12. The portable device app is also used to locate instruments, sets, and/or trays using the location ID function and/or search function to find a specific location for an instrument or tray that correlates to the vertical rack 12 and/or sterile identification barrier 14. The vertical rack 12 display corresponds to a position on the specific location IDs in the portable device app planogram. Additionally, as previously mentioned the portable device app planogram may be mirrored onto the display monitor attached to the vertical rack (or operating room wall, moveable stand, etc) so that multiple people in the room can view the user interface of the planogram at the same time. The location ID 380 pertains to the instrument tray labels, which also correspond to the device app planogram to ensure that the instrument tray is in the correct location.

After the procedure is completed, the user may review the procedure notes to determine whether any changes were made to the planogram at any point during the procedure cycle (382). If the answer is "Yes" then the planogram should be evaluated with all the stakeholders of a given procedure to harvest ideas for potential improvements (384), and the agreed-upon changes should be made so that the planogram is ready the next time the specific surgery is performed. Once this is completed (or if the answer to the previous question (382) was "No"), the planogram for the given procedure should be stored (386) using at least one of direct access local storage 344, external storage 346 (e.g. magnetic disk), or cloud storage 348.

Figure 55:
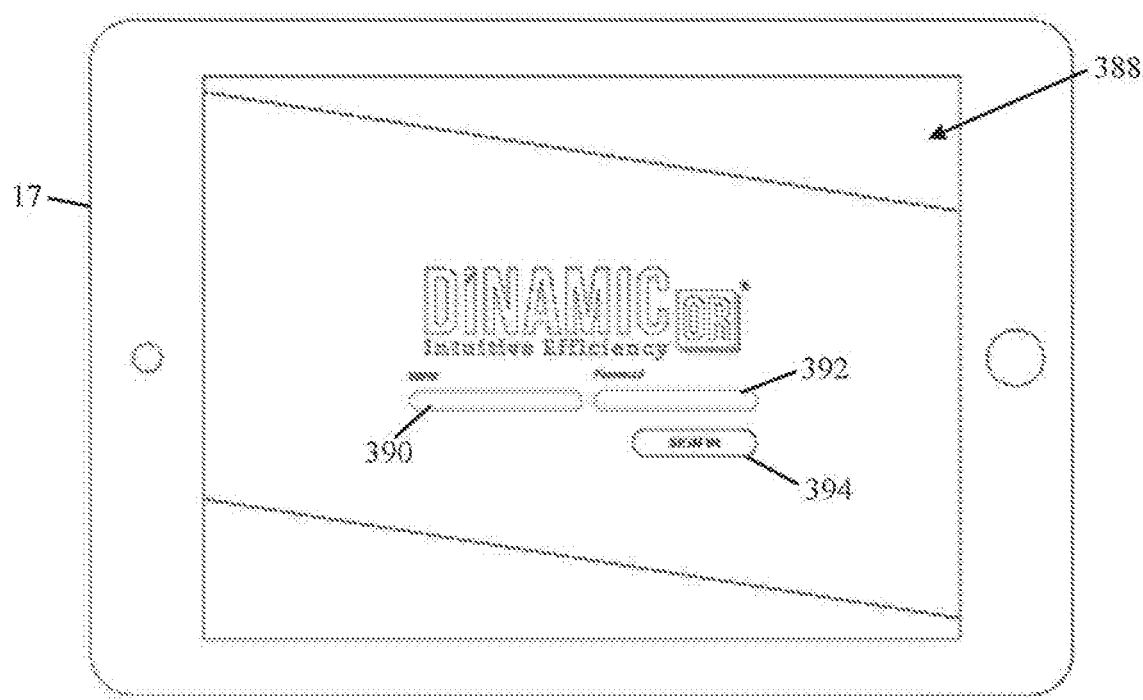
FIGS. 55-76 are plan views of various graphic user interface (GUI) screens forming part of the standardization software platform of FIG. 54.
Figure 56:
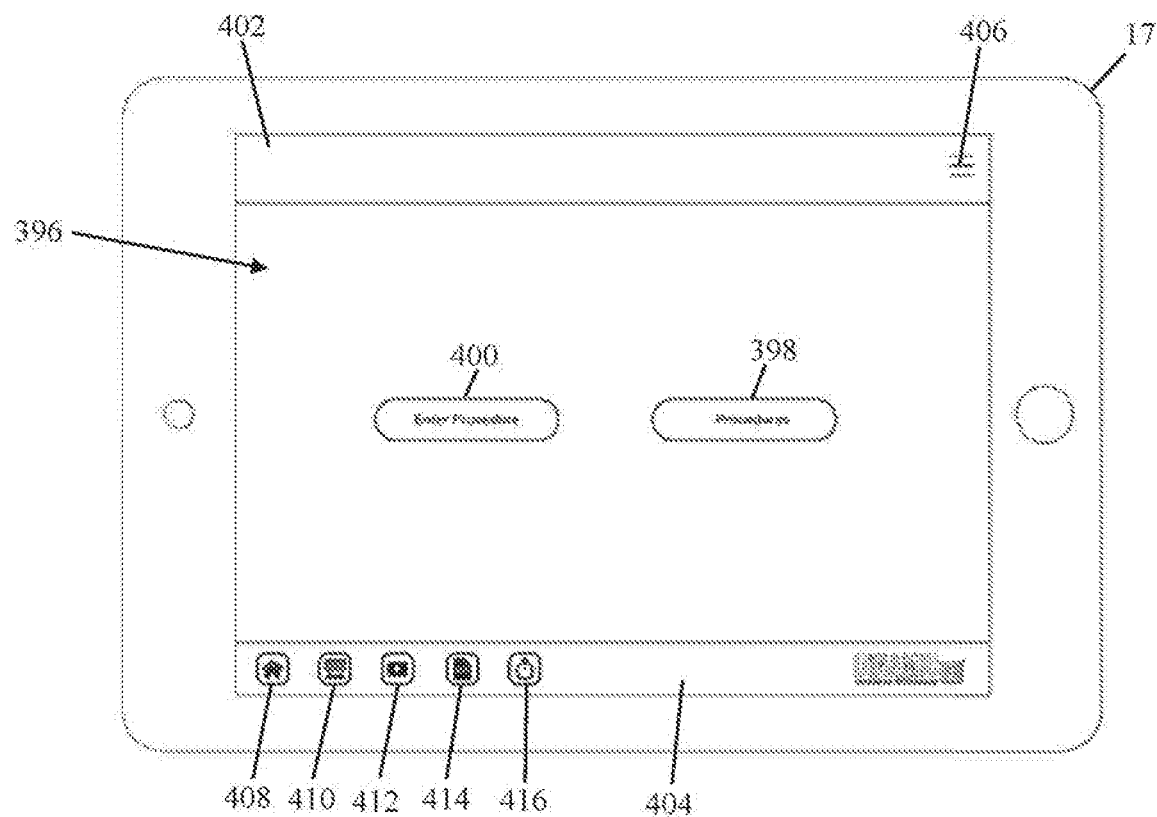

FIGS. 55-76 illustrate various graphic user interface (GUI) screens that an electronic device may present and that a user may encounter while using the standardization software platform 16 before, during, and/or after a surgical procedure. The surgical tray efficiency system 10 is compatible with any loaner, consigned, or facility-owned trays. The setup process generally occurs in a designated area for vendor representatives (e.g. for loaner or consigned trays) or hospital staff (e.g. for facility-owned) to assemble and check the surgical instruments and trays. The setup begins with a user (e.g. vendor representative or hospital staff) logging into the standardization software platform 16 located on a portable electronic device 17 (e.g. tablet computer or smart phone) having a touch-screen interface or laptop computer. FIG. 55 illustrates an example of an initial login screen 388 that verifies the name of the program and includes a name field 390 for the user to input their name and a password field 392 for the user to input their password to gain access to the software. By way of example, tapping on either the name field 390 or the password field 392 causes the electronic device to present a popup virtual keyboard (not shown), enabling the user to input the required information. After populating the name field 390 and password field 392 with the correct information, the user presses the "Sign In" button 394 (e.g., by contacting a location on the display at which the electronic device presents the "Sign In" button 394). The computer verifies the authentication data against a list of registered users and if the authentication data matches, the computer advances the user to the next screen.

Figure 57:
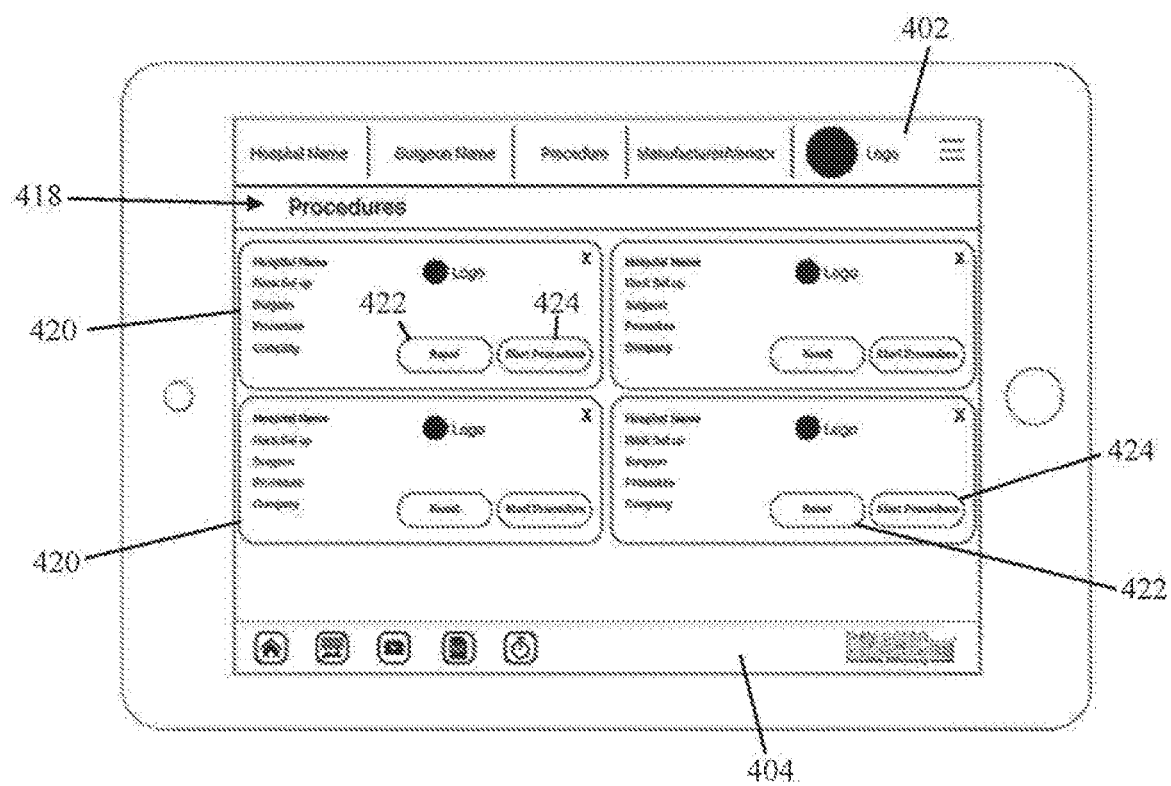

Once the user has successfully logged into the standardization software platform 16, he or she is directed to the home screen 396 (FIG. 56), which the electronic device 17 presents in response to determining that correct authentication data was entered. The display of the home screen 396 includes a "Procedures" button 398, an "Enter procedures" button 400, an information bar 402, and a default menu bar 404. If the imminent surgical procedure is one that has a preexisting planogram already set up, or if the user is unsure whether there is a preexisting planogram for the given surgical procedure, then the user may press the "Procedures" button 398 which prompts the computer to direct the user to the Procedures screen 418 (FIG. 57). If the imminent surgical procedure is not found in the list of procedures on the Procedures screen 418, or if the user knows that the imminent procedure has not been performed previously using the surgical tray efficiency system 10 of the present disclosure, then the user will press the "Enter procedure" button 400, which causes the computer to prompt the user to the Enter Procedure screen 426 (FIG. 58), from which point the user can input the necessary information to start the process of generating a planogram for the imminent surgical procedure.

Figure 59:
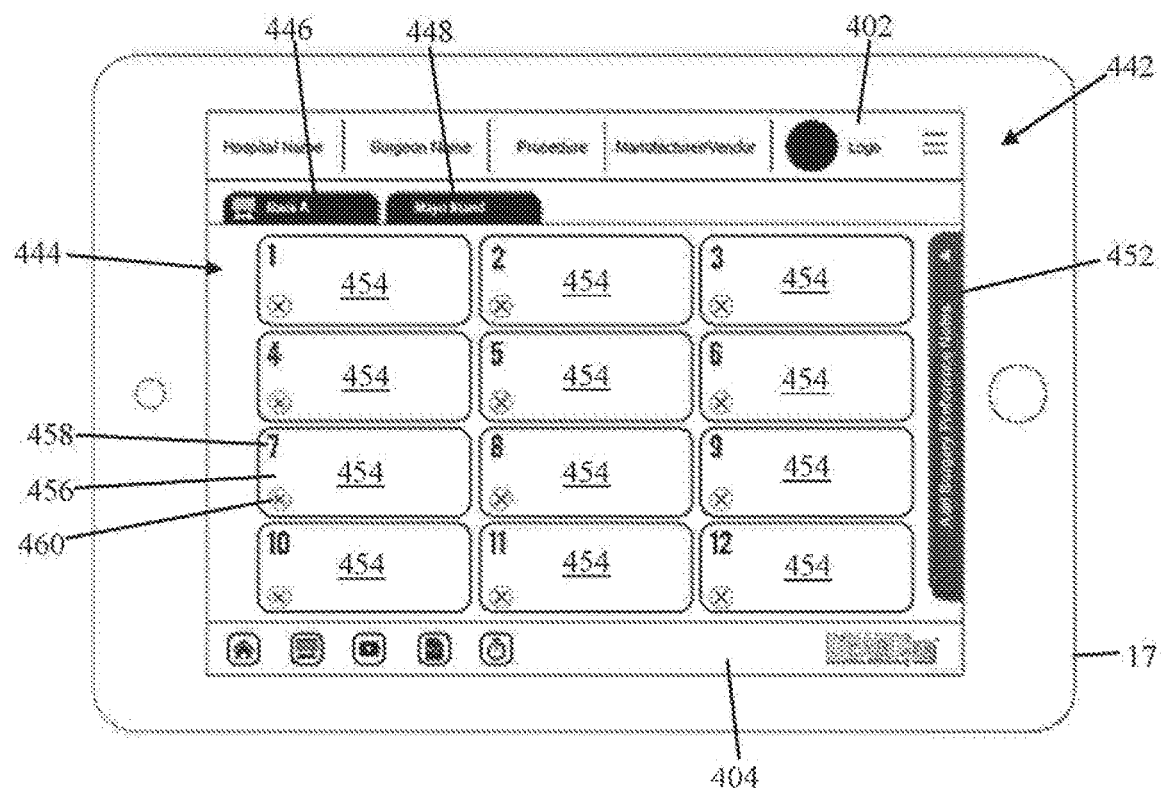
Figure 73:
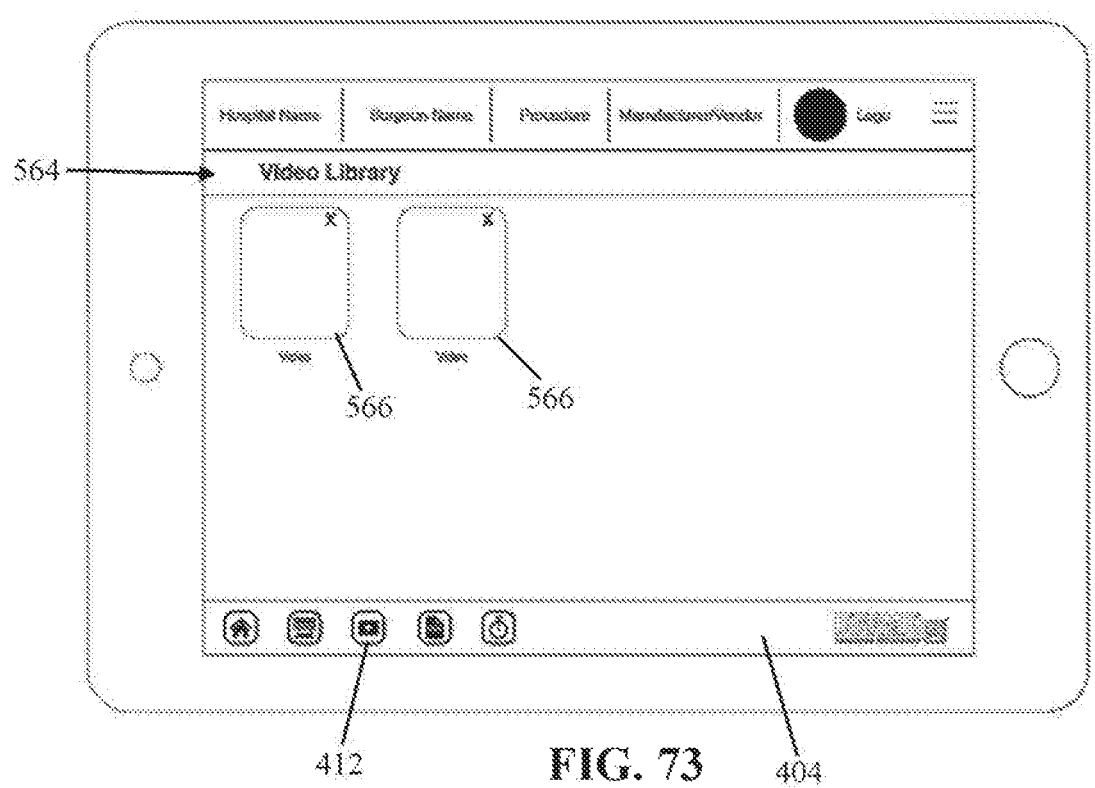
Figure 74:
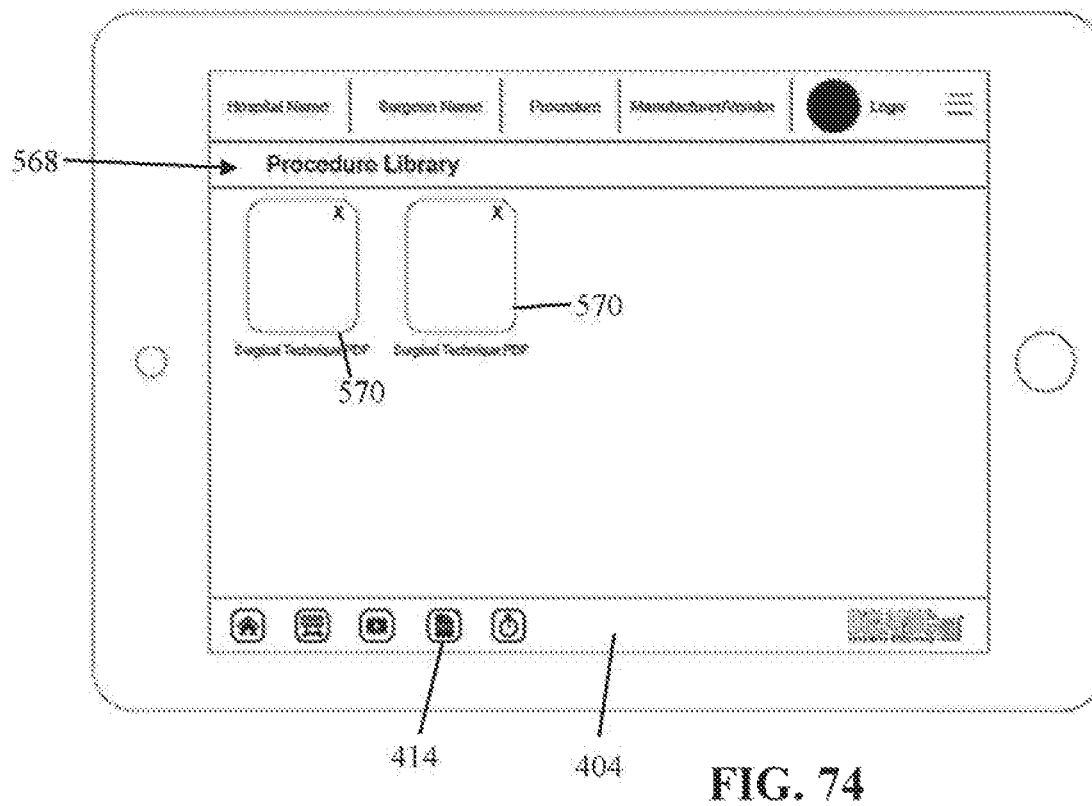
Figure 76:
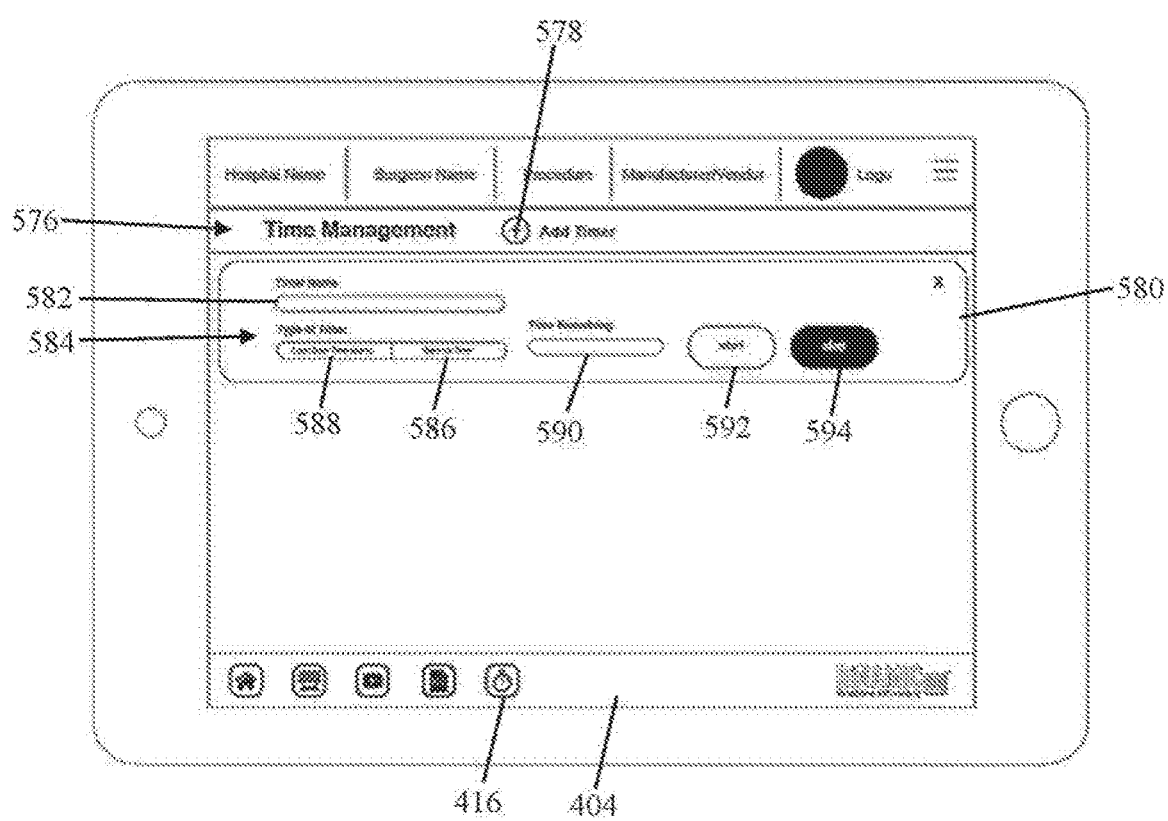

The information bar 402 is present at the top of most of the GUI screens in the app and displays information pertinent to the surgical procedure, as well as a drop-down menu 406 that will be discussed below in conjunction with FIG. 69. The default menu bar 404 is positioned at the bottom of the screen and also appears on most of the GUI screens in the app. By way of example, the default menu bar 404 includes a plurality of permanent "radio" buttons that prompt the computer to direct the user to a specific GUI screen when pressed. By way of example only, the default menu bar 404 includes a "home" button 408, a "planogram" button 410, a "video media" button 412, a "print media" button 414, and a time management button 416. Pressing the "home" button 408 prompts the computer to direct the user to the "home screen" 396 (which in the instant example may merely refresh the page since the user is on the home screen 396 already). Pressing the "planogram" button 410 prompts the computer to direct the user to the planogram screen 442 (FIG. 59). Pressing the "video media" button 412 prompts the computer to direct the user to the Video Library screen 564 (FIG. 73). Pressing the "print media" button 414 prompts the computer to direct the user to the Procedure Library screen 568 (FIG. 74). Pressing the "time management button" 416 prompts the computer to direct the user to the Time Management Screen 576 (FIG. 76).

Discussion herein of users pressing buttons and being directed by the computer to different screens includes the computer determining that user input was received at a location that corresponds to a display of a particular user interface element (e.g., a "button") and in response, and sometimes without receipt of further user input, transitioning the display of the computer from a first user interface screen to a second user interface screen.

FIG. 57 illustrates an example of the "Procedures" screen 418. By way of example, the Procedures screen 418 displays a plurality of procedure ID windows 420 that each display the identifying information for the specific surgical procedures that have preexisting planograms associated therewith. Each procedure ID window 420 includes information such as hospital name, rack set up, surgeon name, procedure name, and vendor name, however any useful information about a given procedure may be displayed. The procedure ID window 420 may also include the hospital logo, a "reset" button 422, and a "start procedure" button 424. Pressing the "reset" button 422 prompts the computer to reset an associated planogram that may be "checked in" already (e.g. FIG. 70) to "not checked in", thereby requiring the user to start the planogram verification process over again. As will be explained, instrument trays are "checked in" on the planogram when they are physically placed on the vertical rack 12 in the operating room. Thus, once all trays are checked in, the standardization software platform 16 (also referred to as "App") is ready for the procedure is ready to begin. Thus by pressing the "reset" button 422, the user is essentially telling the computer that the procedure is not yet ready to begin. Once the vertical rack 12 is set up and the procedure is ready to begin, the user may press the "start procedure" button 424, which tells the computer that the surgical procedure has begun. At this point, the computer may start a running timer to record the overall time necessary to complete the procedure, as well as collect/record other procedure-related data. In addition, the user is directed to the verified planogram screen 546 (FIG. 70) so that the user may use any of the interactive intraoperative features of the app 16.

Figure 58:
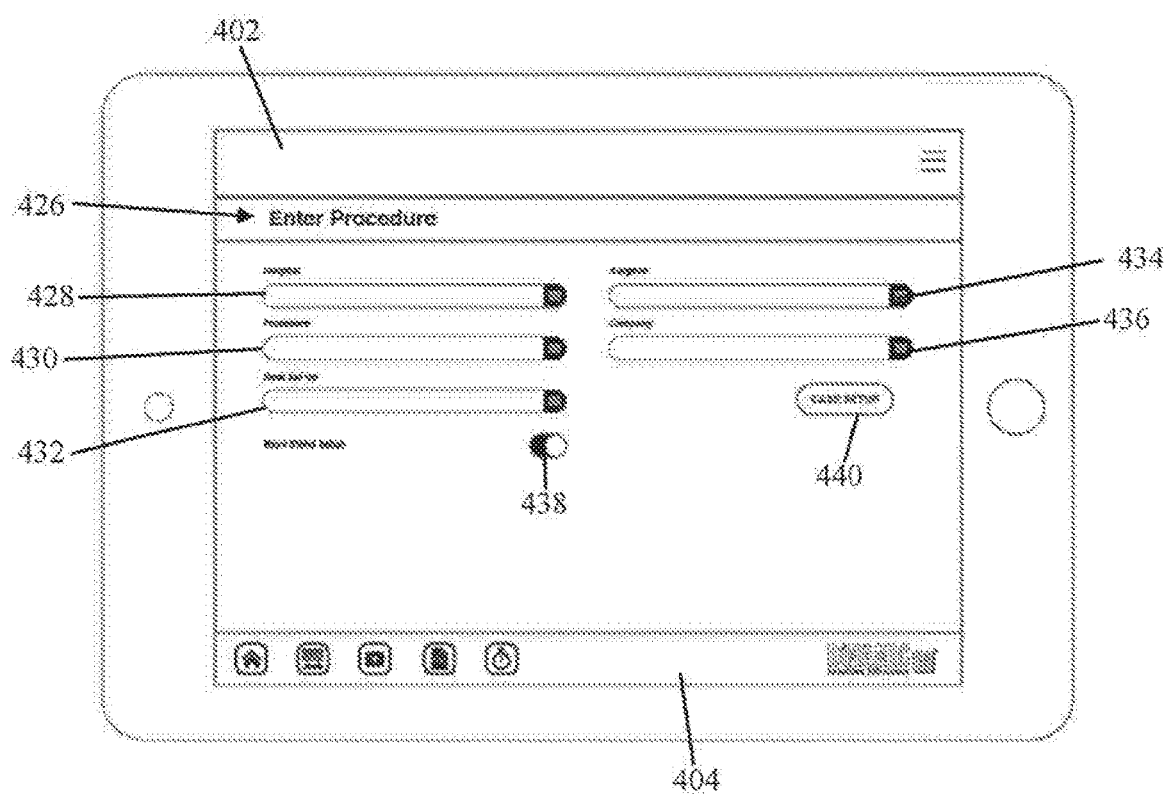

FIG. 58 illustrates an example of an Enter Procedure screen 426, to which a user is directed if a planogram needs to be set up for the imminent surgical procedure (e.g. prior to the first occurrence of a surgical procedure at a certain hospital, or to create a template). On this screen, the user can select various identifying information related to the imminent surgical procedure from a plurality of prepopulated dropdown menus. For example, the Enter procedure screen 426 includes a hospital menu 428, procedure menu 430, rack set up menu 432, surgeon menu 434, and company/vendor menu 436. The various dropdown menus are populated ahead of time whenever a new specific surgical procedure is scheduled. The user can also indicate whether there is a mayo stand setup by engaging a toggle 438. By way of example only, the mayo stand toggle 438 has a default setting of "ON", so in practice the user would deselect the toggle 438 if a mayo stand is not going to be used (or used in conjunction with the App 16). Once this information has been populated, the user presses the "Case Setup" button 440 to advance to the next screen to populate the digital planogram 444.

FIG. 59 illustrates an example of a blank planogram screen 442 that the computer will direct the user to when the user presses the "Case Setup" button 440 on the previous screen. In addition to the information bar 402 at the top of the screen (which by way of example only may now display various identifying information related to the specific procedure, including but not limited to hospital name and logo, surgeon name, procedure name, instrument vendor, and the like) and the default menu bar 404 at the bottom of the screen, the blank planogram screen 442 displays the interactive digital planogram 444 that corresponds to the location ID on the vertical rack assembly 12 (e.g., which may indicate a type of rack assembly 12 and thus its dimensions and available tray locations) and sterile identification barrier 14 (e.g., which may indicate the types and order of the location indicia previously discussed). By way of example, the blank planogram screen 442 includes a rack tab 446, a mayo stand tab 448, a surgery preference notes tab 452, and a plurality of interactive location windows 454. The rack tab 446 and mayo stand tab 448 toggle the user between the planogram setup screen for the rack (shown by way of example in FIG. 59) and a similar setup screen 558 for the mayo table (see FIG. 72 and associated description).

Each interactive location window 454 includes an image display 456, location ID label 458, and a verification toggle 460. In the current example screen, the image display 456 is blank because the user has not set anything up as of yet in the process. The location ID labels 458 correspond directly to the location indicia 264 of the sterile identification barrier 16 and the location indicia 265 affixed to the surgical instrument trays 19 as previously described, and is based upon the number of tray locations for the given vertical rack assembly 12 and sterile identification barrier 16. The discussion of location indicia 264 in relation to the sterile identification barrier 16 is fully applicable to the location ID labels 458 and will not be repeated. In the instant example, the vertical rack assembly 12 in use is a "triple-wide" rack, which includes 4 shelves each capable of holding at least 3 instrument trays. Thus a total of twelve location windows 454 are present in the example planogram described herein. It should be understood that differently-configured vertical rack assemblies (e.g. "double-wide", "single-wide" or other configurations) would require digital planograms 444 that have a different number of interactive location windows 454. By way of example, the interactive location windows 454 include location ID labels that are sequentially numbered 1, 2, 3 . . . 12. The verification toggle 460 may be pressed once the user fully populates the digital planogram 444 and the corresponding instrument trays are placed in the correct locations on the vertical rack assembly 12. This may then change the visual indicator associated with the verification toggle to indicate that the trays are verified as "checked in" for example from an "x" visual indicator that symbolizes "not checked in" to a check mark indicator that symbolizes "checked in."

To begin populating the interactive location windows 454, the user chooses a window and provides user input to select the window (e.g., by tapping on it with a finger or stylus or clicking on it with a mouse). This prompts the computer to direct the user to the tray view screen 462 for that particular tray location. FIGS. 60-66 illustrate an example of a tray view screen 462 (FIG. 60) and some of the various features that are accessible through the tray view screen (FIGS. 61-66).

Figure 60:
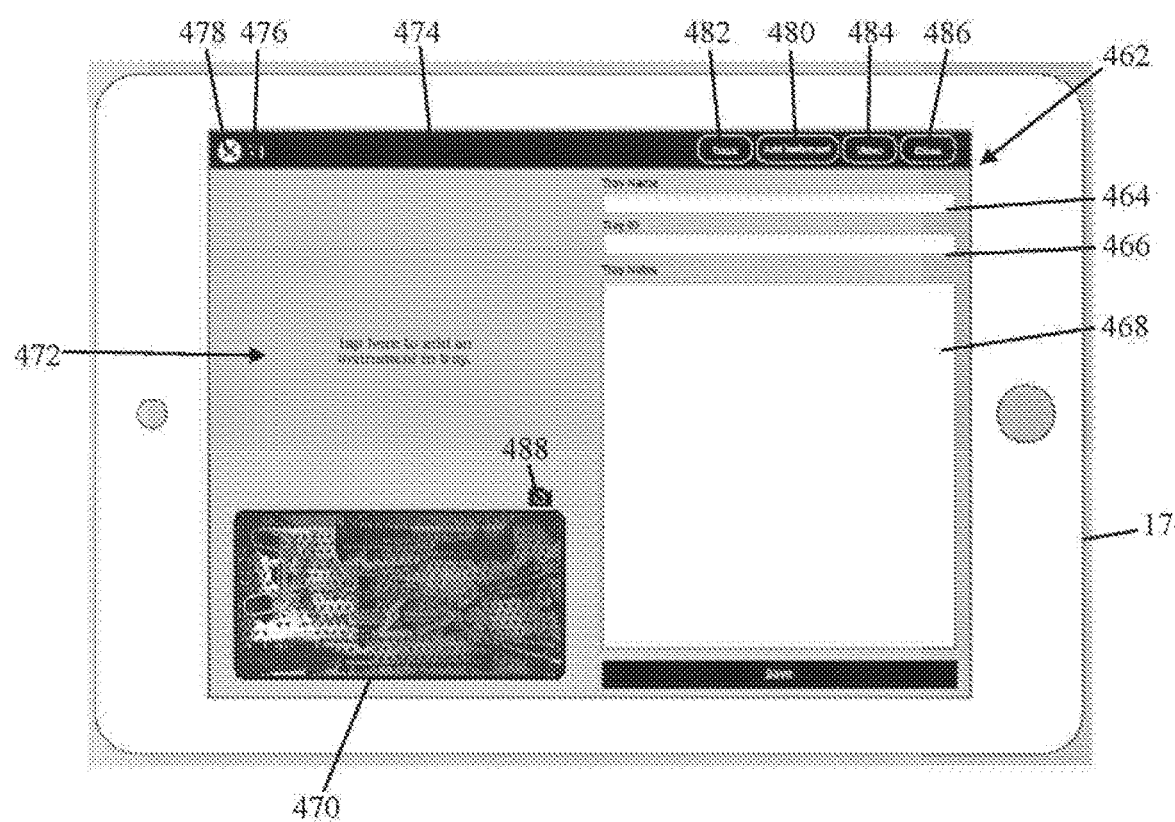

Referring first to FIG. 60, the tray view screen 462 is an interactive screen where the user can input and subsequently view data and media associated with a particular instrument tray 19 (or any other item that is located in the specific location ID spot). By way of example, the tray view screen 462 includes input fields for the tray name 464, tray ID 466, and tray notes 468. The tray name field 464 is customizable in that the user may choose the name for the tray, which for example may be whatever the specific surgeon chooses to call the tray. The tray ID 466 refers to the specific tray serial number (useful for instrument tracking), which may be manually entered or entered via RFID scan, for example. The tray notes field 468 may be used to input any additional notes that may be useful pertaining to a specific instrument tray, such as notes pertaining to surgeon preferences, alternate terminology, missing/broken instruments, etc.

Figure 61:
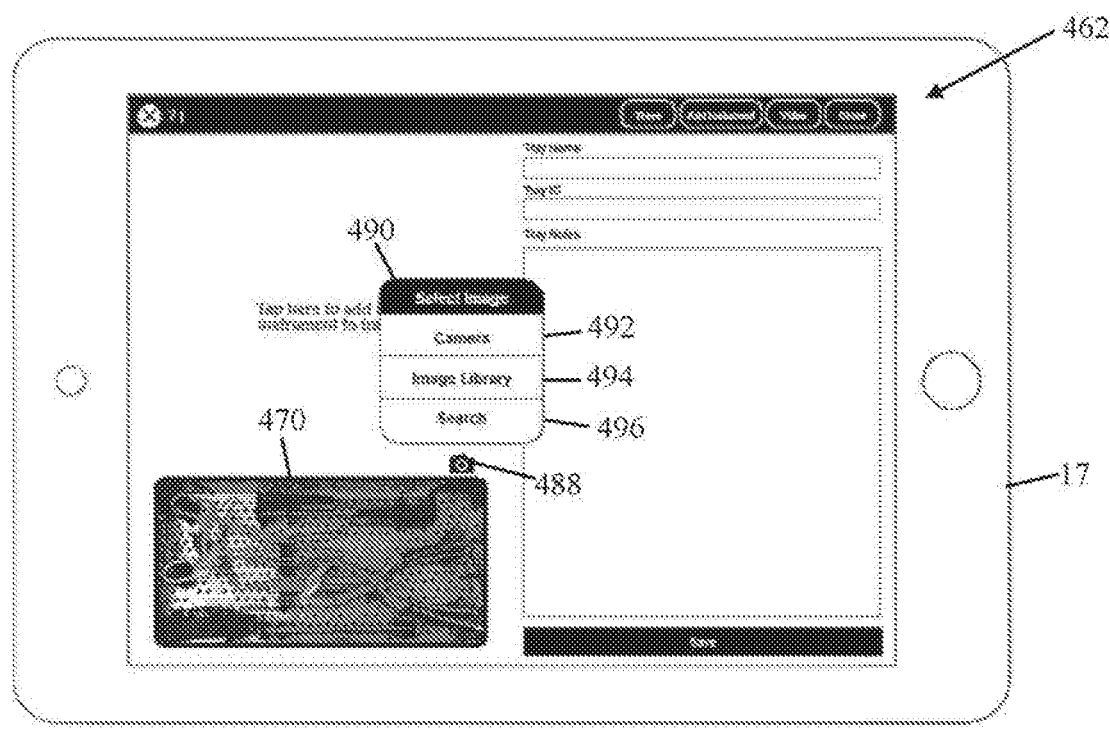
Figure 62:
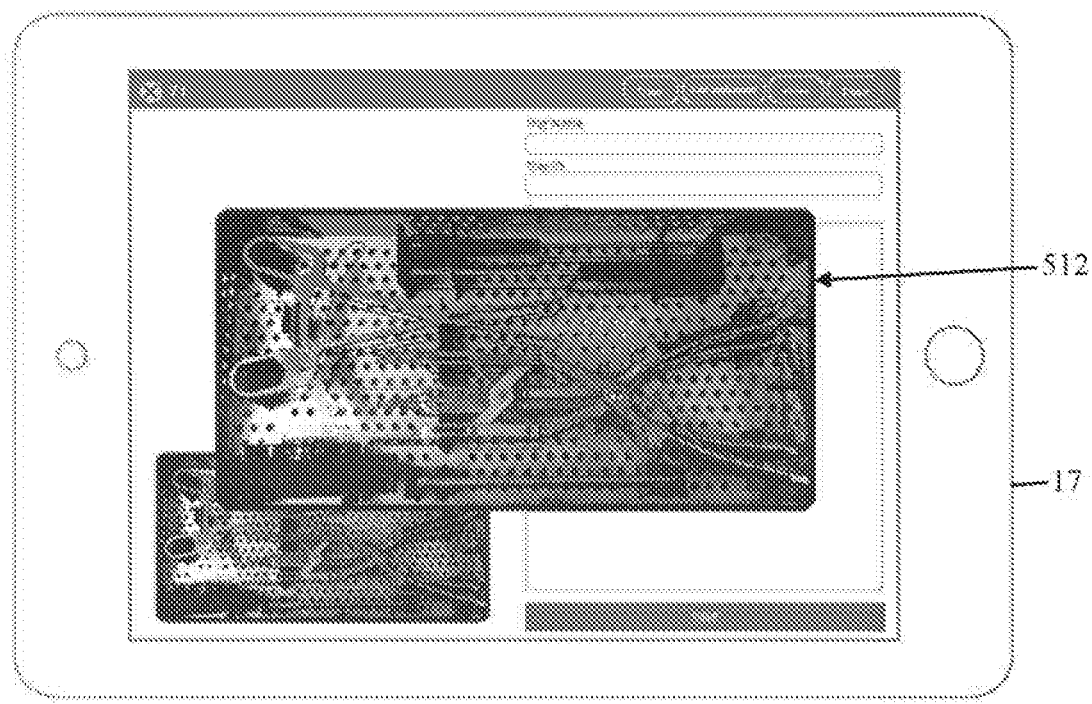

The tray view screen 462 further includes a tray image window 470, interactive instrument list 472, and a menu bar 474 on top of the screen that includes a tray identifier 476, tray verification indicator 478, an "add instrument" button 480, "trays" button 482, "video" button 484, and a "close" button 486. The tray image window 470 may be populated with an image of the instrument tray (or whatever else might be in that particular planogram location if not an instrument tray). To populate the tray image window 470 (or change the current image), the user presses a "camera" icon 488 positioned adjacent the tray image window 470, which causes a popup image selection menu 490 to appear (FIG. 61). On the popup image selection menu 490, the user can select to obtain an image using the device's own camera 492, view a local image library 494, or search the cloud 496 for an image. Once the tray image window 470 is populated, tapping on the image itself prompts the computer to activate the "zoom view" 512, which comprises an enlarged image of the instrument tray (FIG. 60).

Figure 63:
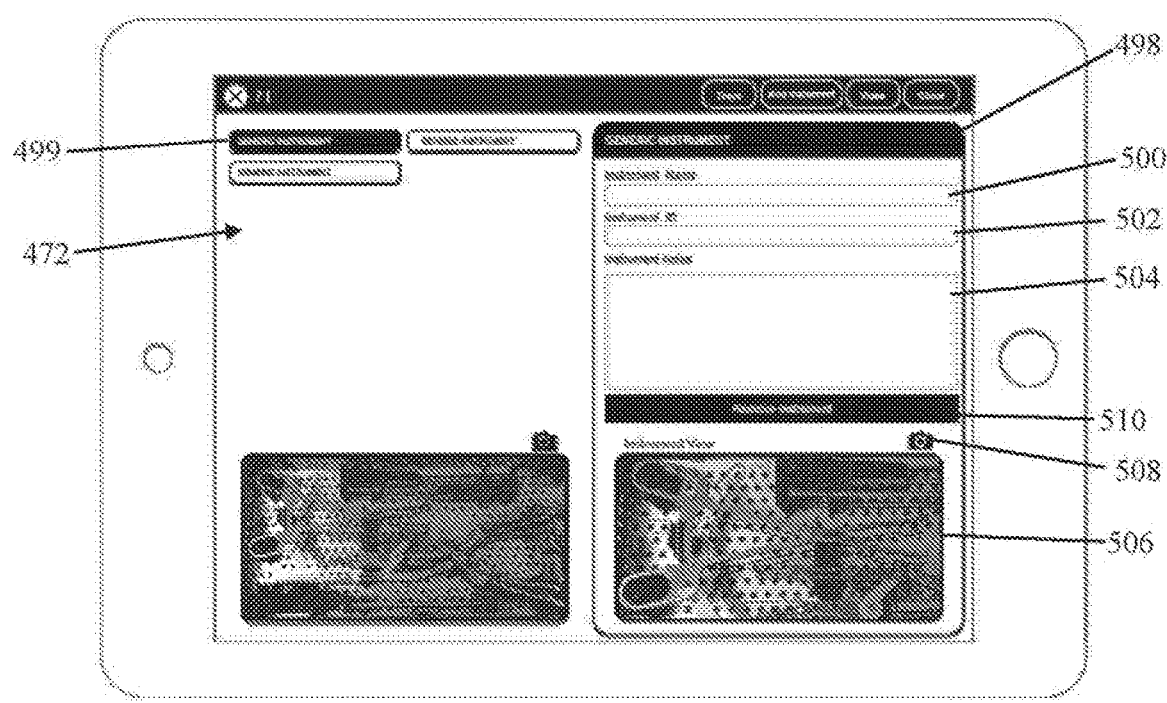

To add data (e.g. photo, video, notes, name, etc) about an instrument to the tray view screen 462, a user taps on the "add instrument" button 480 in the top menu bar 474 or alternatively taps in the interactive instrument list area 472. Referring now to FIG. 63, either action prompts the computer to open the instrument view window 498 over the portion of the tray view screen 462 that includes the tray name 464, ID 466 and notes 468, and create an interactive instrument ID tag 499 in the interactive instrument list 472. (Subsequently, pressing on an interactive instrument ID tag 499 will open the particular instrument view window 498 for that instrument). The instrument view widow 498 includes an instrument name field 500, instrument ID field 502, and instrument notes field 504. The user may input any name for the particular instrument that they want, but it should be noted that the name in the instrument name field 500 is the name that is searchable by the app 16. The instrument ID 502 refers to the specific instrument serial number (useful for instrument tracking), which may be manually entered or entered via RFID scan, for example. The instrument notes field 504 may be used to input any additional notes that may be useful pertaining to a specific instrument. The instrument view window 498 further includes an image window 506, camera icon 508, and a "remove instrument" button 510. The image-related functionality of the instrument view window 498 is identical to the image-related functionality of the tray view screen 462. Thus, the image window 506 and camera icon 508 operate in identical fashion to the tray image window 470 and camera icon 488 discussed above. Tapping on an image in the image window 506 opens a "zoom view" in the same manner as the tray view described above. Pressing the "remove instrument" button 510 deletes the instrument from the tray, which causes the computer to remove the instrument ID tag 499 in the interactive instrument list 472.

Figure 64:
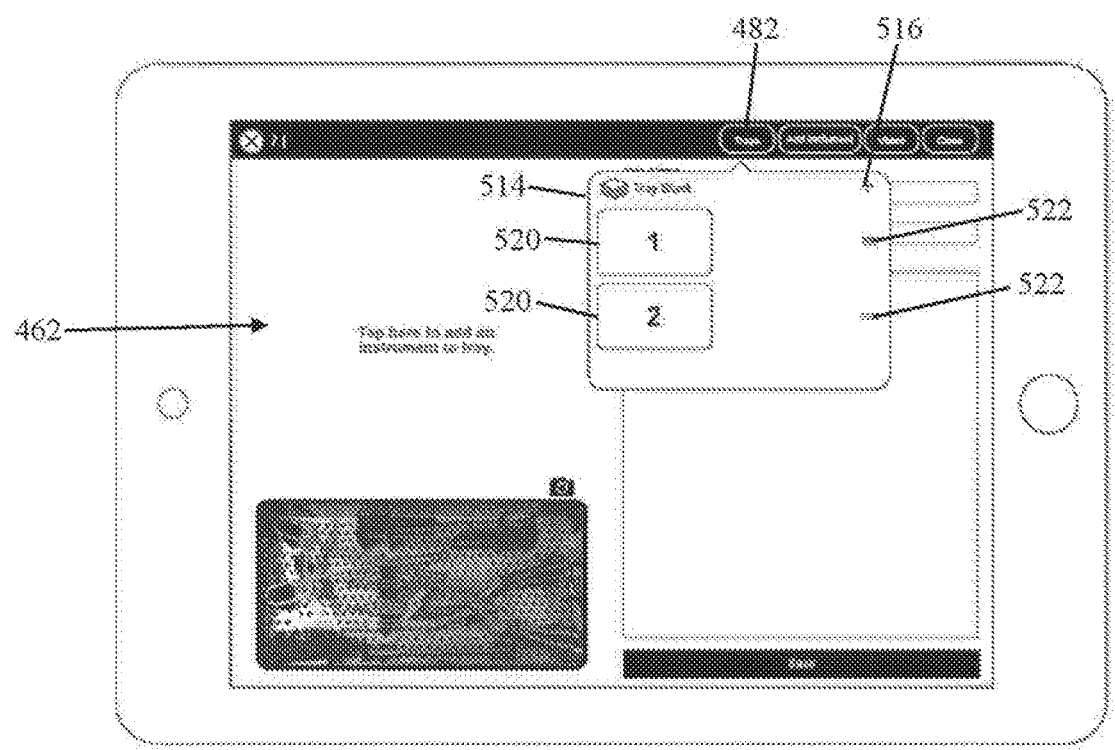

The standardization software platform 16 of the present disclosure is configured to recognize the possibility of stacking trays within the planogram. Referring to FIG. 64, pressing the "trays" icon 482 causes a stacked tray popup window 514 to appear. The stacked tray popup window 514 allows a user to create a tray stack by adding trays, and then managing the tray stack by toggling between tray views and adding or deleting trays as becomes necessary. To add a tray to the stack, a user presses the "+" icon 516 (for example). In the instant example the user has created a two-tray stack. To access the information in the first tray, the user taps on a first tray icon 518, for example a window with a "1" identifier (although other identifiers may be used). This causes the computer to display the tray view screen 462 for that specific instrument tray. The user can populate that tray view screen as described above. When the user desires to switch to the tray view screen 462 of the other tray in the stack, the user again presses the "trays" button 482, and then a second tray icon 520 in the stacked tray popup window 514, for example a window with a "2" identifier. This causes the computer to switch to the tray view screen 462 for the second stacked tray. To remove a tray in the stack, the user presses the "−" icon 522 that is specific to the stacked tray that the user would like to remove (for example).

Figure 65:
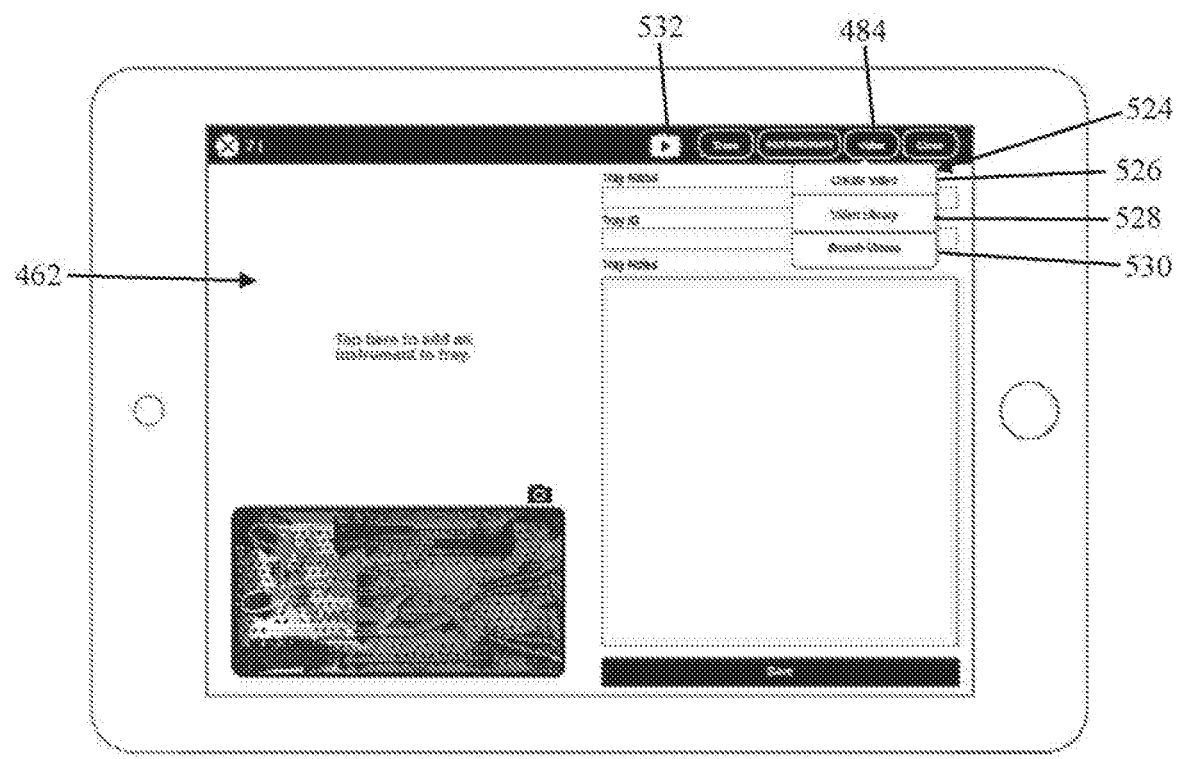

Referring to FIG. 65, the "video" button 484 on the tray view screen 462 allows the user to add, play, replace and remove videos that are input into standardization software platform 16 for that specific instrument tray. Videos may contain instructions about that specific instrument tray, including how to assemble or use various instruments within the tray. Pressing the "video" button 484 on the tray view screen 462 prompts a popup menu 524 including selectable options to create video 526, view library 528, and search videos 530. Choosing the "create video" 526 option prompts the computer to open the device's video camera function. The user can then record their own video and save it to the app 16. The "view library" 528 option allows the user to view the locally stored video library to select an appropriate video. The "search videos" 530 option prompts the user to do a cloud search for a relevant video. The computer presents a video icon 532 in the menu bar 474 on the tray view screen 462 as well as in the image display 456 of the planogram when the computer determines that there is at least one video associated with the instrument tray. Additionally, videos that are added in the tray view screen 462 are also added to the video library 564 for the procedure (FIG. 73). FIG. 64 shows the full-screen video 534 that pops up when a video is selected. The selected video will also show on any external mirrored displays, for example the monitor 52 on the vertical rack assembly 12 (or operating room wall). Any sound associated with the video can be heard through the speakers on portable electronic device 17 and/or speakers that may be provided on the vertical rack assembly 12.

When the user is finished setting up the tray view screen 462, the user may return to the planogram screen 442. The data previously entered is automatically saved. The interactive location window 454 associated with that particular instrument tray will now display the same image that is displayed in the tray image window 470.

Figure 67:
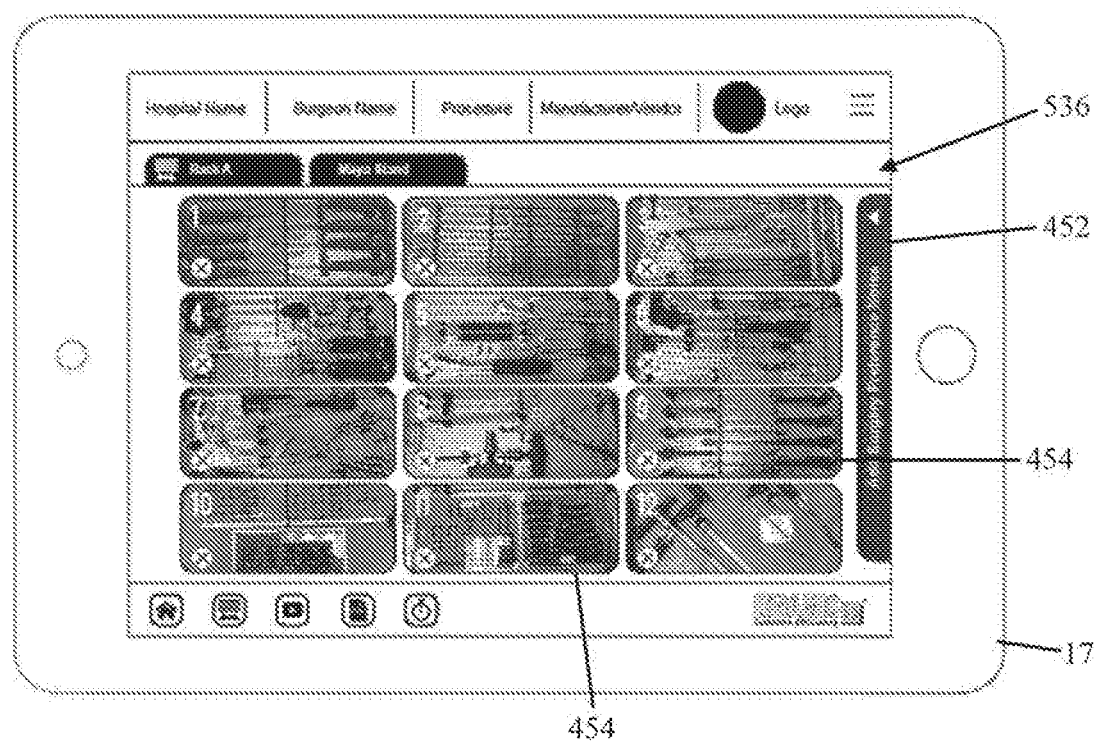

FIG. 67 illustrates an example of a populated but unverified planogram screen 536, which is what the user will see upon completion of the various tray view screens. At this point, each interactive location window 454 displays a representative image of the instrument tray (or other item) in each location. By way of example, the images shown are full tray images, however other identifiers may be used. In this view, the user may start to place instrument trays within the vertical rack assembly 12 as arranged in the planogram. If during this process (or any other time) the user decides to rearrange the trays in some way, the interactive location windows 454 may be moved to a different spot in the planogram. By way of example, this movement may be accomplished by the user pressing and holding his/her finger on the location window 454 until the window "releases" from the planogram, and then dragging the location window 454 to a new location, at which point the user releases his/her finger from the display at which time computer may determine a rearrangement of location windows to adapt to the new location of the dragged location window.

Figure 68:
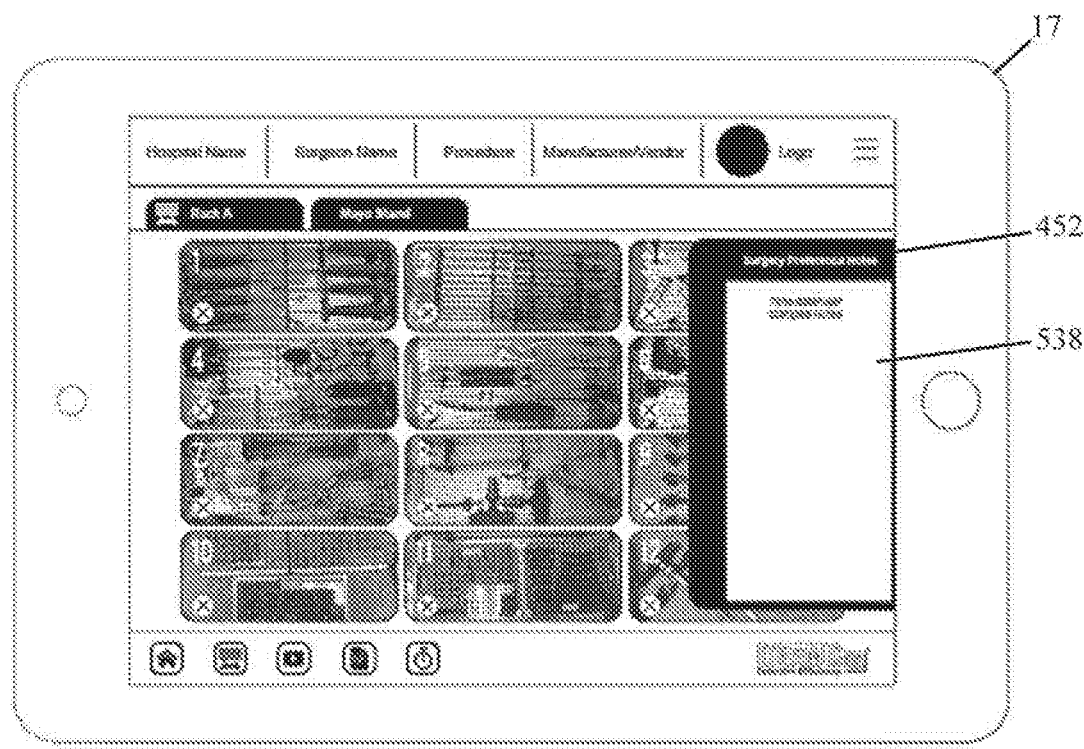

Referring to FIG. 68, at any time during the setup process or during the surgery, the user may input information into the surgery preference notes window 538, which pops open when the user taps on the surgery preference notes tab 452. By way of example, these notes may have certain associated data recorded when the notes are made, for example including but not limited to time stamp, date, user, and the like. When finished, the user simply taps on the border of the window 538 to collapse the window 538.

Figure 69:
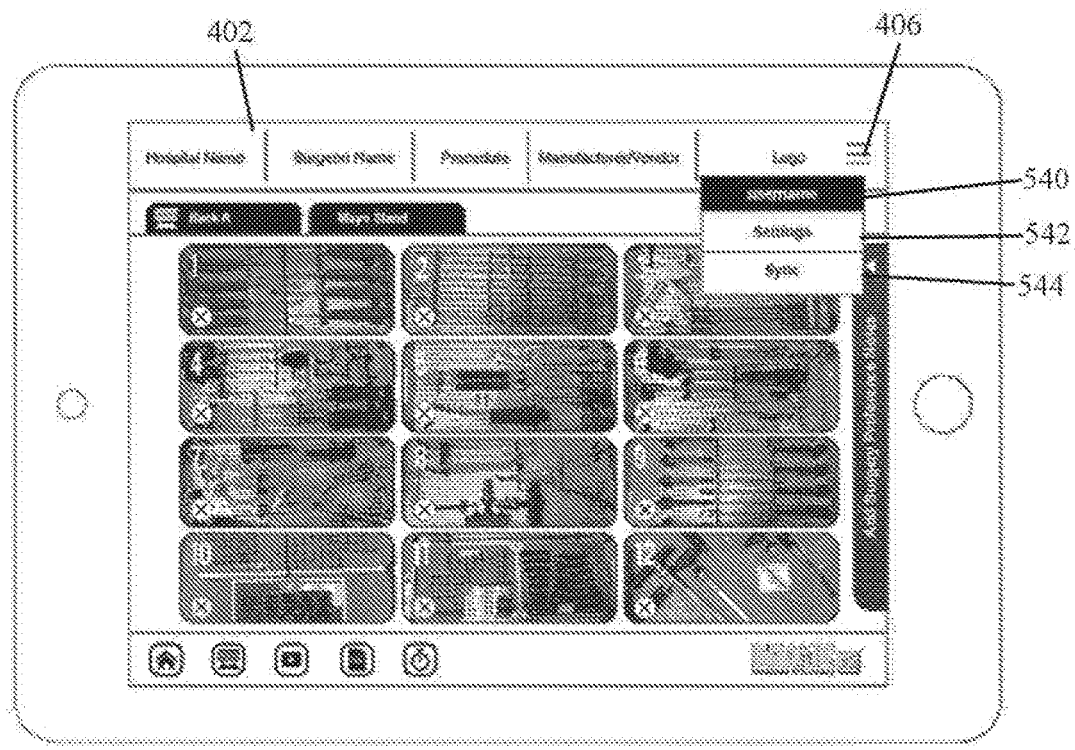

Referring to FIG. 69, the dropdown menu 406 in the information bar 402 includes options to select/view username 540, settings 542, and sync 544. Selecting the username option 540 displays user information. Selecting the settings option 542 opens a settings menu (not shown) to allow the user to adjust various settings. Selecting the sync option 544 allows the user to instruct the computer to sync the data stored in the app (via WiFi) to the user's cloud profile. This data may include new planogram settings as well as data collected during a surgery (e.g. user information, time stamps, duration, searches performed, tray movements, etc). By way of example, the app 16 may be configured to automatically sync periodically if the portable device 17 is connected to a WiFi network. This menu option gives the user the ability to instruct the app 16 to sync immediately.

Figure 70:
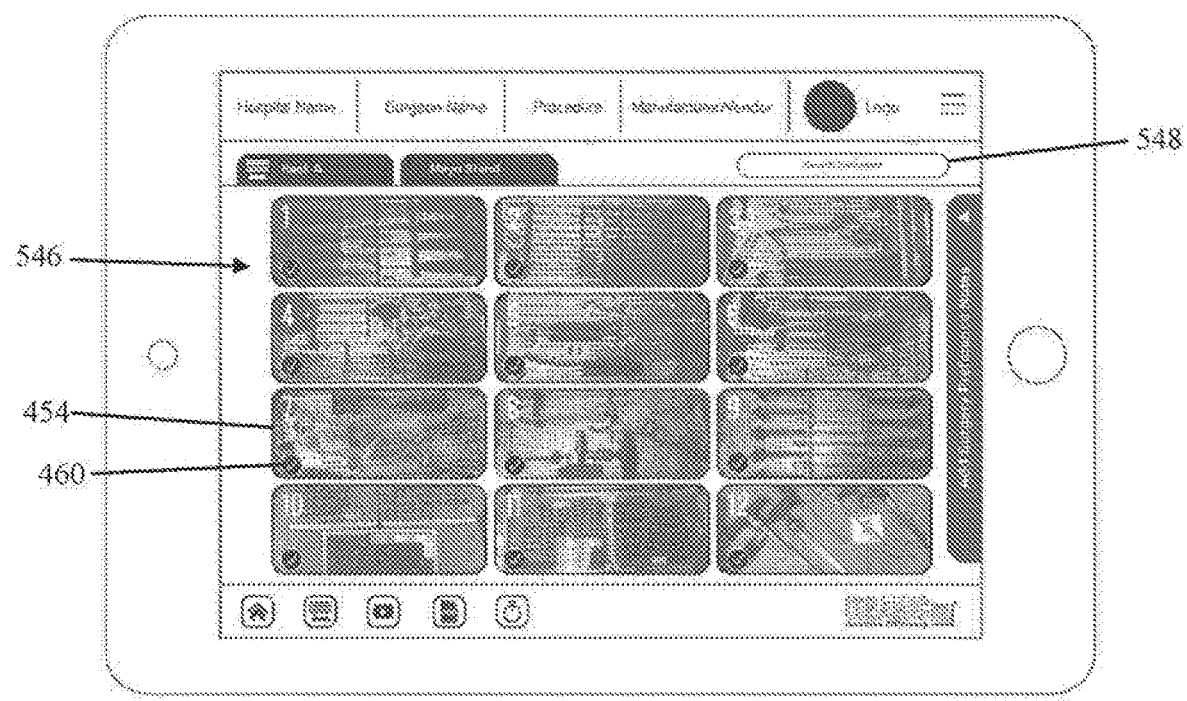

Referring to FIG. 70, an example of a verified planogram screen 546 is shown. Once the user has placed an instrument tray on the vertical rack assembly 12 in the location ID position corresponding to the planogram, the user may tap the verification toggle 460 to confirm this correct placement. This may then change the visual indicator associated with the verification toggle 460 to indicate that the tray is verified as "checked in" for example from an "x" visual indicator that symbolizes "not checked in" to a check mark indicator that symbolizes "checked in." When the verification toggles 460 in all of the interactive location windows 454 display a check mark indicator (in the current example), then all the instrument trays have been confirmed as placed in the correct position on the vertical rack assembly 12 and the setup process is complete. At this point the surgical tray efficiency system 10 is ready for the surgery to begin.

During the surgery, one advantageous feature of the surgical tray efficiency system 10 is the ability for a user to use the app 16 to search for a particular instrument, and have the app 16 reveal the location of said instrument. To do this, the user taps the "search instrument" button 548. Although currently shown as being associated with the verified planogram screen 546, it should be understood that the "search instrument" button 548 may be included in other app 16 screens as well. For example, the instrument data is searchable during setup, and not just after setup is complete.

Figure 71:
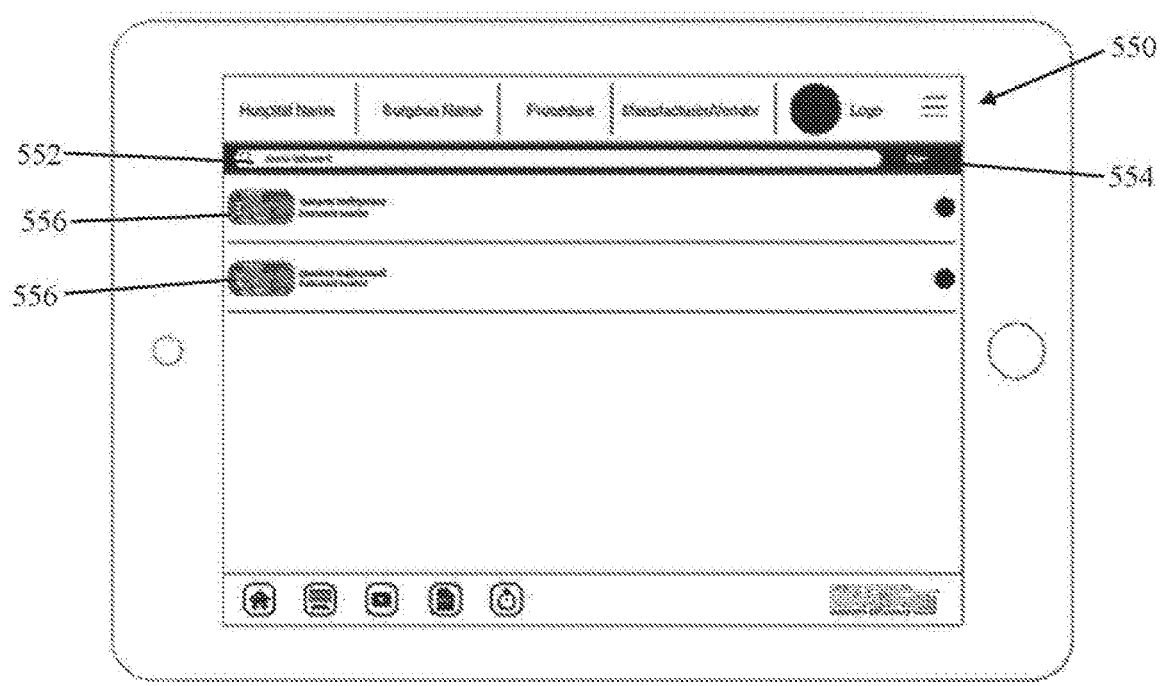

Tapping on the "search instrument" button 548 prompts the computer to direct the user to the search instrument screen 550, an example of which is shown in FIG. 71. The search instrument screen 550 includes a search instrument input field 552 positioned near the top of the screen. The user enters the name of the desired instrument into the search instrument field 552 and presses the "done" button 554 located on the right of the input field 552. The app 16 will search the instrument name data and provide a location listing 556 for each instance in which the searched-for appears. The location listing 556 lists the name and location of the instrument. Tapping on the location listing 556 prompts the computer to direct the user to the instrument view screen 498 for that particular instrument (e.g. FIG. 63).

Figure 72:
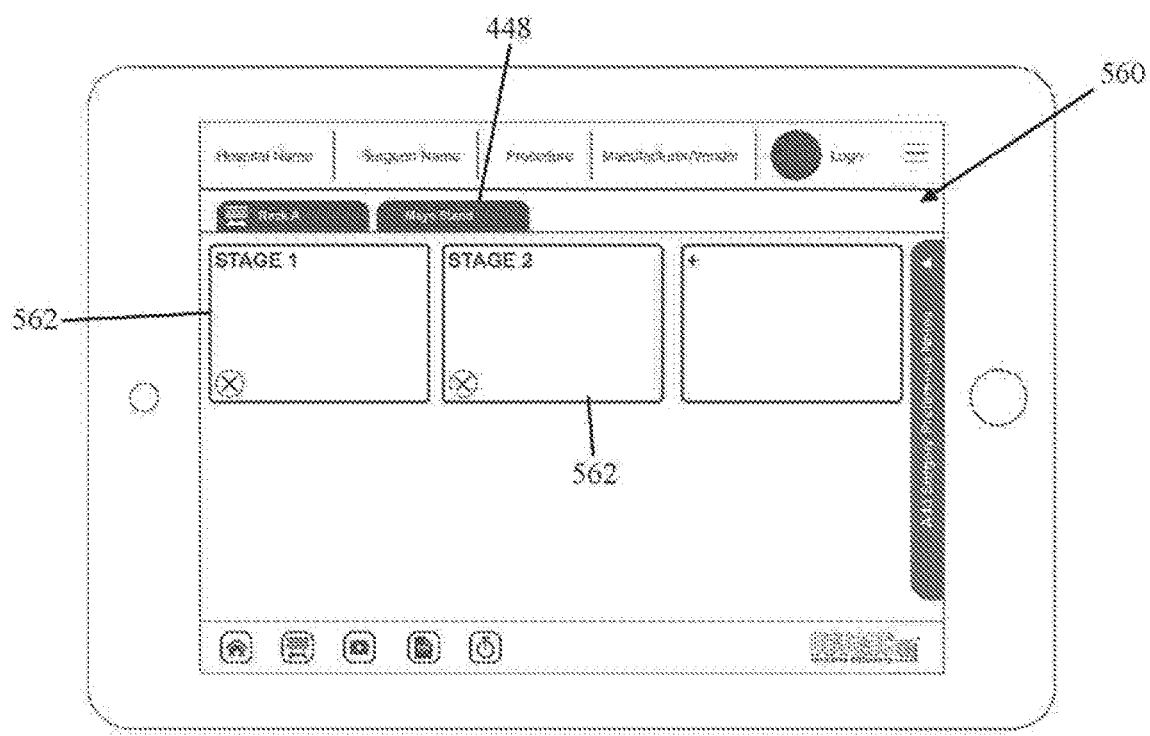

FIG. 72 illustrates an example of a mayo stand planogram screen 558 that a user is directed to when they tap on the mayo stand tab 448 described above. A mayo stand is basically a utility tray that is used as a staging area for surgical instruments and other material that is in the queue for impending use during the procedure. The standardization software system 16 provides for organizing the mayo stand in a similar fashion to the vertical rack assembly 12, with the main difference being that unlike the planogram 444 for the vertical rack assembly 12, the mayo stand "planogram" 560 does not have a predetermined number of location windows that correspond to a particular location. Instead, the mayo stand "planogram" 560 may have up to six stage windows 562 that are added at the user's discretion. The stage windows 562 may be populated with any instrument or combination of instruments that the user chooses. Tapping on the any of the stage windows 562 prompts the computer to direct the user to the stage view screen for that particular stage. The stage view screen is identical to the tray view screen 462 described previously in features and functionality.

Figure 66:
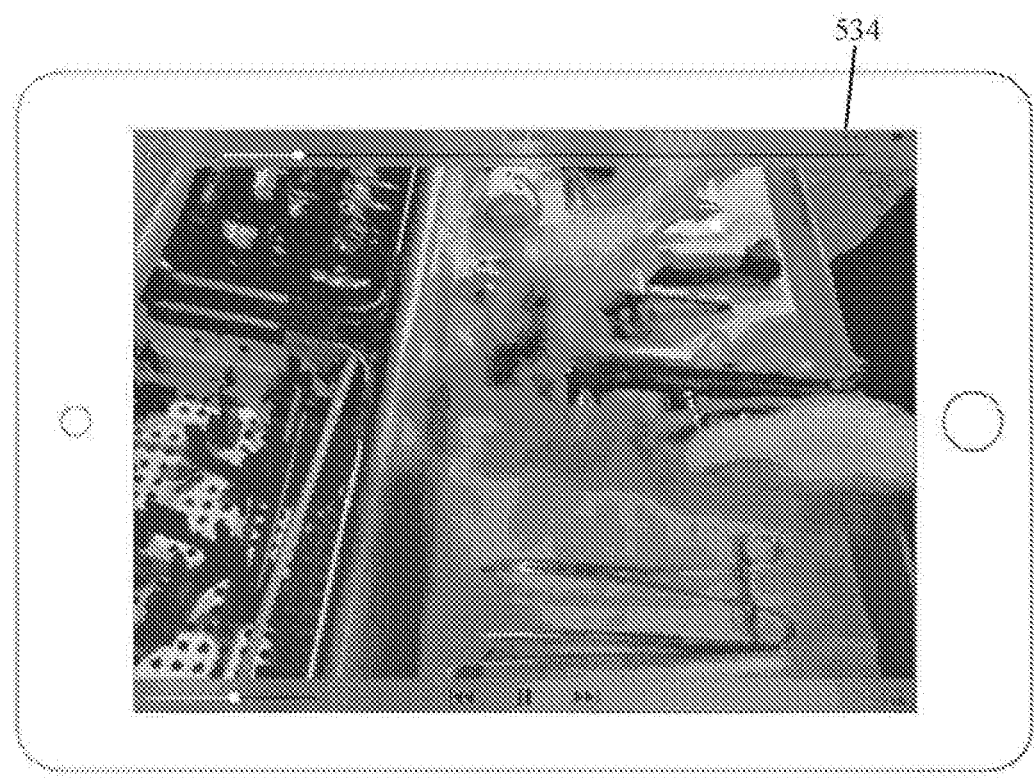

FIG. 73 provides an example of a video library screen 564 that may be accessed by tapping on the video media icon 412 on the default menu bar 404 that is present on most GUI screens in the app 16. The video library 564 includes a video icon 566 for each video that has been added to the surgery profile. Videos that pertain to specific instruments will be labeled with the instrument location. Tapping on any video will cause the video to play in a full-screen format (FIG. 66).

Figure 75:
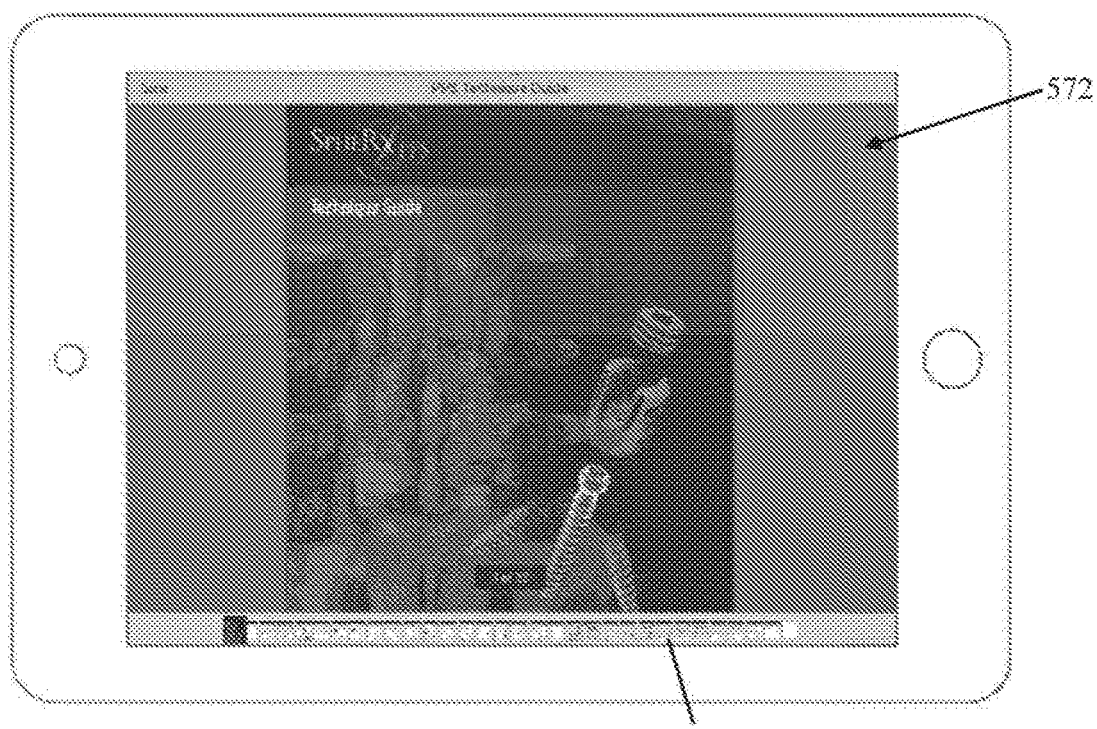

FIG. 74 illustrates an example of a procedure library screen 568 that may be accessed by tapping on the print media icon 414 on the default menu bar 404 that is present on most GUI screens in the app 16. The procedure library 568 is a storage collection for all PDF document files that are associated with the surgical procedure. Primarily these are likely to be various technique guides, however any PDF document associated with the procedure may be stored in the procedure library 568. The procedure library 568 includes a PDF icon 570 for each PDF file stored therein. Tapping on a PDF file will cause the PDF file to open in a full-screen PDF reader 572 (FIG. 75). The user can turn the page by swiping across the screen or by selecting a page from the page bar 574 at the bottom of the screen.

FIG. 76 illustrates an example of a time management screen 576 that may be accessed by tapping on the "time management" button 416 on the default menu bar 404 that is present on most GUI screens in the app 16. The time management screen 576 includes an "Add timer" button 578, that when pressed causes the computer to offer a timer window 580 to the user. The timer window 580 includes a name field 582 to allow the user to assign a name to the timer, a timer type selector 584 where a user chooses between a count up timer 586 and a countdown timer with alarm 588, a time indicator 590 that shows the time remaining on a countdown timer or the time elapsed on a count-up timer, a start button 592 and a stop button 594. The time management screen 576 allows the user to configure count up and count down timers that can be used to record and time certain features such as but not limited to the overall surgery time, cement set time, set up time and turnover time. Multiple timers can be used at the same time.

Many variations on the basic design are possible. For example, there may be more or fewer than four shelves on the vertical rack assembly, the angle at which they are mounted to the rack may be greater or less than thirty degrees, the shelf angle may be adjustable. The length of each shelf may be sufficient length for one or more surgical tray lengths. The shelves may include a sensor array (e.g. pressure, mechanical, electrical) to collect certain data. The sterile identification barrier also may vary in length and number of identification labels to correlate to the length of the vertical rack assembly. The standardization software platform also may vary depending on the number and configuration of vertical shelf assemblies used for a given surgical procedure.

Figure 77:
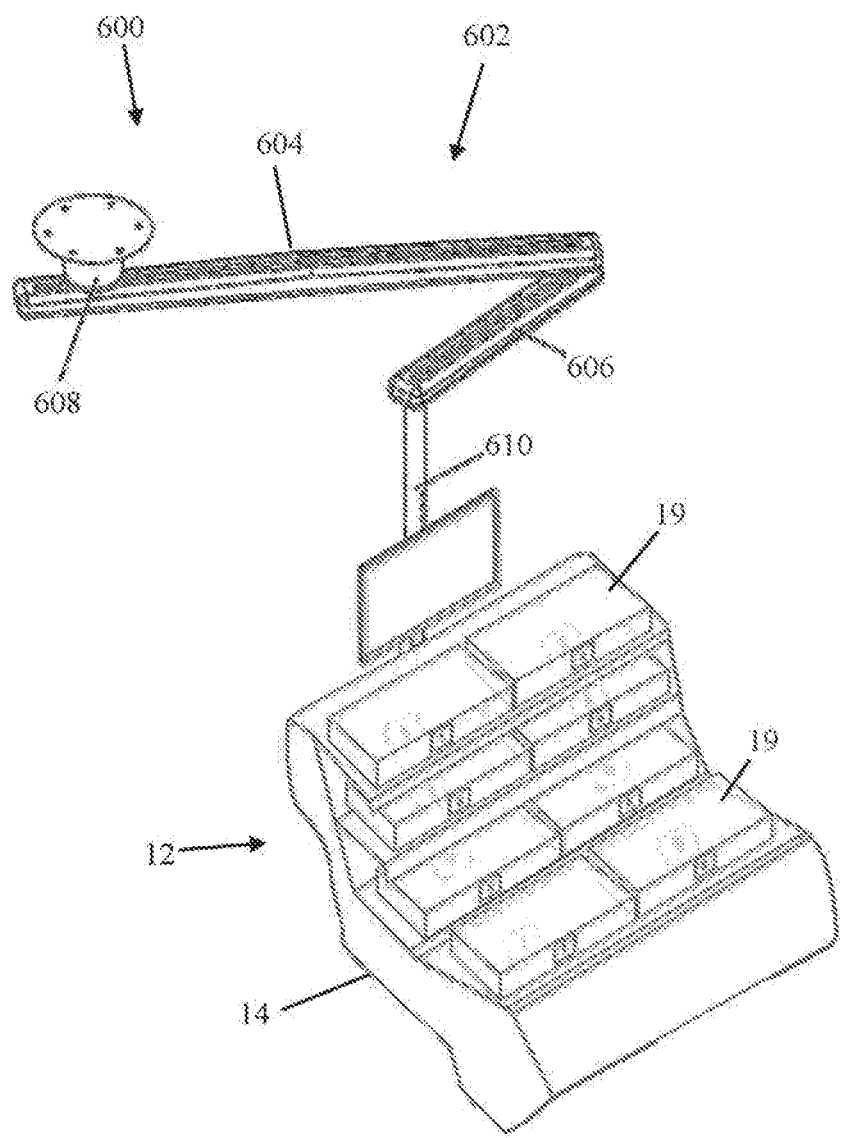
FIG. 77 is a perspective view of one example of a vertical rack assembly of FIG. 2 adapted to hang from a ceiling.

In some instances, it may be advantages to mount the surgical tray efficiency to the operating room wall or ceiling. FIG. 77 illustrates an example of a ceiling attachment feature 600 that can be used with a vertical rack assembly 12 to secure the vertical rack assembly 12 to the ceiling. By way of example, the ceiling attachment feature comprises a boom assembly 602, however any suitable mechanism of attachment to a wall or ceiling may be used. The boom assembly 602 includes (by way of example only) a first extension 604 pivotally associated with a second extension 606. A ceiling mount 608 for mounting the boom assembly 602 to the ceiling is rotatably attached to one end of the first extension 604. The second extension 606 is pivotally connected to the first extension 604 at the end of the first extension 604 that is opposite the ceiling mount 608. The second extension 606 is rotatably connected to a connector element 610 at the end of the second extension 606 that is opposite the first extension 604. The connector element 610 securely connects the vertical rack assembly 12 and the ceiling attachment feature 60. By way of example, the connector element 610 of the present example comprises a post that attaches to the pivot bar 50 (FIG. 7), however any mechanism capable of securely attaching the vertical rack assembly 12 to the ceiling attachment feature 600 may be used without departing from the scope of this disclosure.

Figure 78:
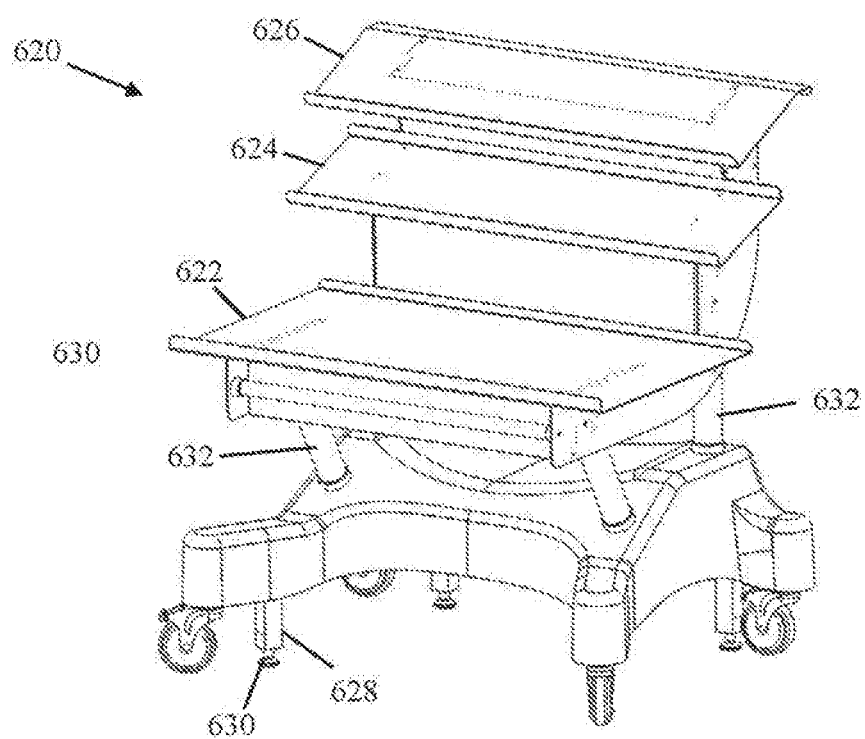
FIG. 78 is a perspective view of another example of a vertical rack assembly forming part of the surgical tray efficiency system of FIG. 1.

In some instances, it may be useful to have vertical rack assembly 12 with a different shelf configuration from the examples previously shown and described. FIG. 78 illustrates another example of a vertical shelf assembly 620 according to the disclosure. The vertical shelf assembly 620 includes a plurality of shelves configured to receive instrument trays. By way of example, the vertical shelf assembly 620 includes a first shelf 622, a second shelf 624, and a third shelf 626. The first shelf 622 is deep enough (e.g. front-to-back) to receive surgical instrument trays that are arranged perpendicular to a longitudinal axis running through the first shelf 622. By way of example, the second and third shelves 624, 626 are identical to the corresponding shelves described above.

Another notable feature highlighted by the present example is the extended height differential between the first shelf 622 and the second shelf 624. This may be useful to ensure proper access to all the instruments within a tray, particularly in the event that the trays situated in the first shelf 622 are rotated ninety degrees relative to the trays in the second shelf 624.

Figure 79:
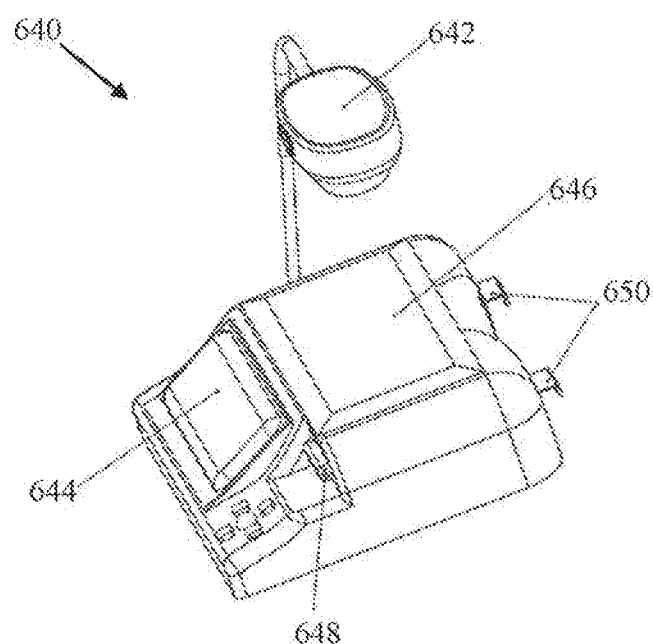
FIG. 79 is a perspective view of an example of an item identification unit for use with the surgical tray efficiency system of FIG. 1.

The vertical shelf assembly 620 shown by way of example further includes a plurality of risers 628 attached to the base frame. The risers 628 include telescoping feet 630 that endeavor to raise the height of the vertical rack assembly 620. Other ways of adjusting the height of the vertical rack assembly 620 may be possible, including but not limited to telescoping vertical supports 632 and/or a central telescoping post that may be expanded mechanically, electronically, pneumatically, hydraulically, etc. Additionally, the various shelves may be expandable (e.g. from "double-wide" to "triple-wide" and vice versa) without departing from the scope of the disclosure. Although the various shelves are shown and described herein by way of example as being fixed to the vertical rack assembly 12 at a particular angle, optionally one or more of the shelves may be angularly adjustable relative to the vertebral rack assembly and one another. In addition, the shelves may be height-adjustable relative to one another. By way of example only, the adjustment mechanisms may be manual, mechanical, electronic, magnetic, pneumatic, or hydraulic in nature. Taking into account the height-adjustability of the vertebral rack assembly, the vertical rack assembly may be fully adjustable to support a user's needs, FIG. 79 illustrates an example of an identification/tracking assembly 640 that may be used to create/capture data regarding certain surgical instruments (or other items) that may be imported into and displayed on the instrument view screen of the app 16 discussed above, and later analyzed for instrument tracking purposes. By way of example only, the identification assembly 640 comprises a camera/scanner 642, an identification interface 644, a scale 646, a label printer 648 and attachment element 650 that provides the support necessary to mount the identification assembly 640 onto a vertical rack assembly (not pictured). The camera/scanner 642 may be provided to take images of instruments to populate the planogram as described above, as well as for instrument tracking purposes. In one example the computer may include instrument recognition software that works with the camera/scanner 642 to automatically recognize assign identification data to various instruments as the image is captured. The camera/scanner 642 may be configured to scan MD, bar codes, etc to capture/load instrument data (for example stock photos, videos, technique guides, and the like) and tracking information. Instrument tracking may also be integrated with the cloud via WiFi. The scale 646 may be calibrated to determine weight at least to the nearest milligram.

Figure 80:
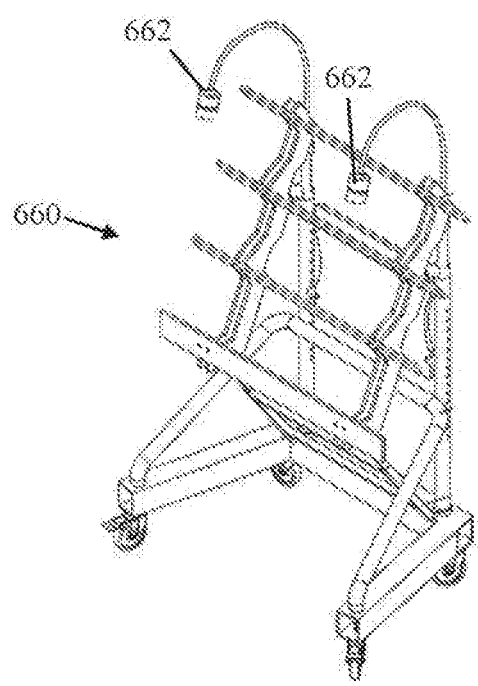
FIG. 80 is a perspective view of another example of a vertical rack assembly forming part of the surgical tray efficiency system of FIG. 1, highlighting the use of additional lighting.

FIG. 80 illustrates another example of a vertical rack assembly 660, illustrating in particular the feature of attached light elements 662. The attached light elements 662 provide additional lighting for the surgical instrument trays. The attached light elements 662 may be connected to a power source housed in the base of the vertical rack assembly 660 or alternatively be connected to an external power source, for example such as a wall socket. The attached light elements 662 may be positioned above the vertical rack assembly, on the shelves (e.g. luminescent track lighting), and/or within the shelves (e.g. for sterile non-metallic shelves). The attached light elements 662 may be configured to light up particular areas at particular times, for example when a user executes a search for a particular instrument in the planogram software, the computer not only displays the location ID of the instrument on the user's GUT but may also cause light elements 662 in the area of the identified location to illuminate.

In a similar configuration to the light elements 662, the vertical rack assembly 12 may be equipped with localized sterilization element such as aerosol, vacuum, and/or antimicrobial sprays. The sterilization elements may be controlled manually and/or automatically to sterilize according to a preset timer. The sterilization elements may be configured to cover all instruments at the same time, or alternatively (or in addition) be configured to act over a certain specified area (e.g. single tray, shelf, zone, quadrant, etc).

Figure 81:
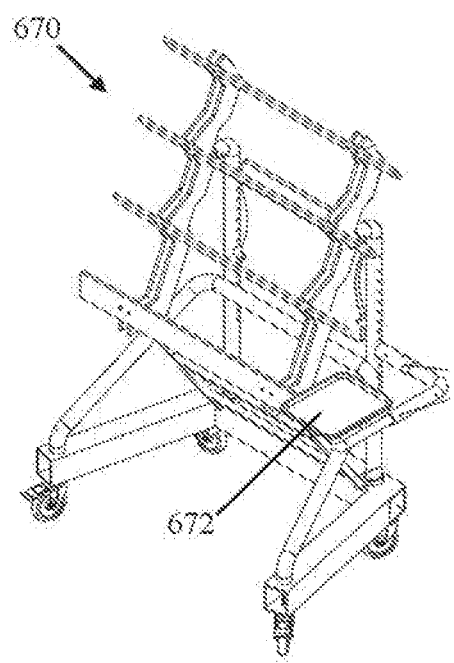
FIG. 81 is a perspective view of another example of a vertical rack assembly forming part of the surgical tray efficiency system of FIG. 1, highlighting the attachment of an additional utility tray.

FIG. 81 illustrates another example of a vertical rack assembly 670, illustrating in particular the feature of an attached basin or mayo stand 672. The attached basin or mayo stand 672 may be a useful staging area for instruments that are or will be imminently needed during a procedure. As the user is retrieving instruments for the mayo stand/basin, the user may populate the mayo stand planogram in the App 16 as described above. By way of example, the attached basin or mayo stand 672 may be attached to the side of the vertical rack assembly and be moveable to a more desirable position. Alternatively, the mayo stand/basin may be slideably attached to the vertical rack assembly for example above or below the grab handle 48.

Many variations to the standardization software platform 16 are also possible. For example, although the user input interface has been described herein as touch (or mouse) based, in some instances the standardization software platform 16 may include a voice recognition component, enabling the computer to respond to vocal input commands. For example, a user may initiate an instrument search by speaking aloud the name of the instrument (e.g. "Find reamer"). The computer receives the vocal input, analyzes the command and then displays the virtual location of the requested instrument on the planogram display (and optionally may cause the actual illumination of the instrument tray located on the vertical rack assembly 12). The software may continuously update in real time a digital planogram preference list, with smart tool integration such that the software "learns" (e.g. based on use patterns, etc.) the most-used tools/kits for a given procedure and the sequence of use of such tools to create a "most played list" where the more commonly-used tools are at the top of the list and thus more easily found. The software may be configured to provide the surgical team a pre-op walkthrough so everyone knows what to expect when it is time for the surgery.

The software may be configured to have more real time functionality, for example maintaining an up-to-date operating time line, with digital notification of certain events including but not limited to start time, procedure type, length, room location, complexity, staffing, timer expiration (integrated with time management function), and the like. Also, the software may enable/record secure, real time communication with offsite instrument vendor representatives, thereby reducing the need (e.g. expense, scheduling, crowding, etc.) for vendor representatives to be physically present in the operating room during a procedure. This communication may include video conferencing. The surgeon could be wearing a head-mounted camera (for example located on eyewear or a headband) to enable the offsite representative to "see" what the surgeon is seeing in real time. The software may be configured to record the video images captured through the head-mounted camera.

In some implementations, the planogram computer processes may be able to communicate with robotic devices that are directly or indirectly used in surgical procedures or other surgical-related tasks. For example, various different types of robotic devices may be used in surgical procedures, such as robotic devices performing surgical procedures autonomously, robotic devices operating under the direction of a surgeon, and robotic devices that are used to simply retrieve surgical instruments for the surgeon or another member of the surgical team.

The planogram computer processes may receive a request to provide a robotic device with a location of a particular surgical instrument. The request may have been issued by a different computer process that works communicatively with the robotic device to retrieve surgical instruments for the robotic device. In some examples, the request is issued autonomously by a robotic device that is working autonomously to perform a surgical procedure or a portion thereof (e.g., a robotic device that is autonomously stitching a wound may autonomously request the location on vertical rack assembly 12 of a different-sized needle). In some examples, the request is issued by the robotic device or corresponding computer process in response to user input that was provided by a user of the robotic device, such as a surgeon. Indeed, an on-site or remote surgeon operating the robotic device may provide input specifying the need for a different surgical instrument to cause the robotic device to retrieve the surgical instrument, rather than manually manipulating an arm or other portion of the robotic device to a location of a surgical instrument on vertical rack assembly 12.

The robotic computer process may transmit the request to the planogram software process through an Application Program Interface (API) of the planogram software process, and may specify the particular surgical instrument requested (e.g., by name or unique identifier). In response, the planogram computer process, may determine whether the instrument is stored by any tray in the vertical rack assembly. If so, then the planogram computer process may return to the robotic computer process an indication of a location of the requested instrument on the vertical rack assembly, or instructions for accessing the requested instrument.

In response to the robotic software process receiving the indication of the location of the requested instrument (or movements to perform to access the instrument), the robotic device or a component thereof may move to a tray at which the requested tool is located, and may perform operations to determine a location of the requested instrument on the tray.

Those additional actions can include analyzing one or more images that are captured by a camera attached to the robotic device, the vertical rack assembly 12, or one that is mounted elsewhere in the surgical room. A computing system can compare such images to pre-stored images of the surgical instrument, to identify which item located on a tram is the surgical instrument. Alternatively or additionally, the robotic device can include other types of sensors for use in determining or verifying the identity of a surgical instrument. For example, the surgical instrument may include unique identifiers that can be read by infrared sensors or RFID systems.

At this point, the robotic device may grab the requested instrument or otherwise perform actions for attaching the requested instrument to the robotic device. The robotic device may then give the robotic instrument to another robot, the surgeon or another member of the surgical team. Should the robotic device keep the instrument rather handing it off to a device or person, at this point the robotic device may use the instrument in the surgical procedure. Planogram computer processes may indicate that the instrument is in use.

Returning a surgical instrument generally involves performing similar operations, but in reverse. For example, an autonomous robotic device or an operator of a robotic device may determine that a different instrument is needed. At this point, the robotic device may either return its currently-attached or held robotic instrument to the location on a tray at which it was previously taken, or the computer processes operating in conjunction with the robotic device may send a request to the planogram computer processes to determine a location at which to place the robotic instrument, and the planogram computer process may send back information that identifies such a location. The robotic instrument may perform such a query to ensure that the robotic instrument is placed in its correct location, even if trays or instruments thereon have been moved since the time that the robotic instrument retrieved the instrument.

The robotic device may then return the instrument to its preferred location on a vertical rack assembly 12, and the planogram user interface may provide a graphical indication that the instrument is now stored on the vertical rack assembly 12.

Figure 82:
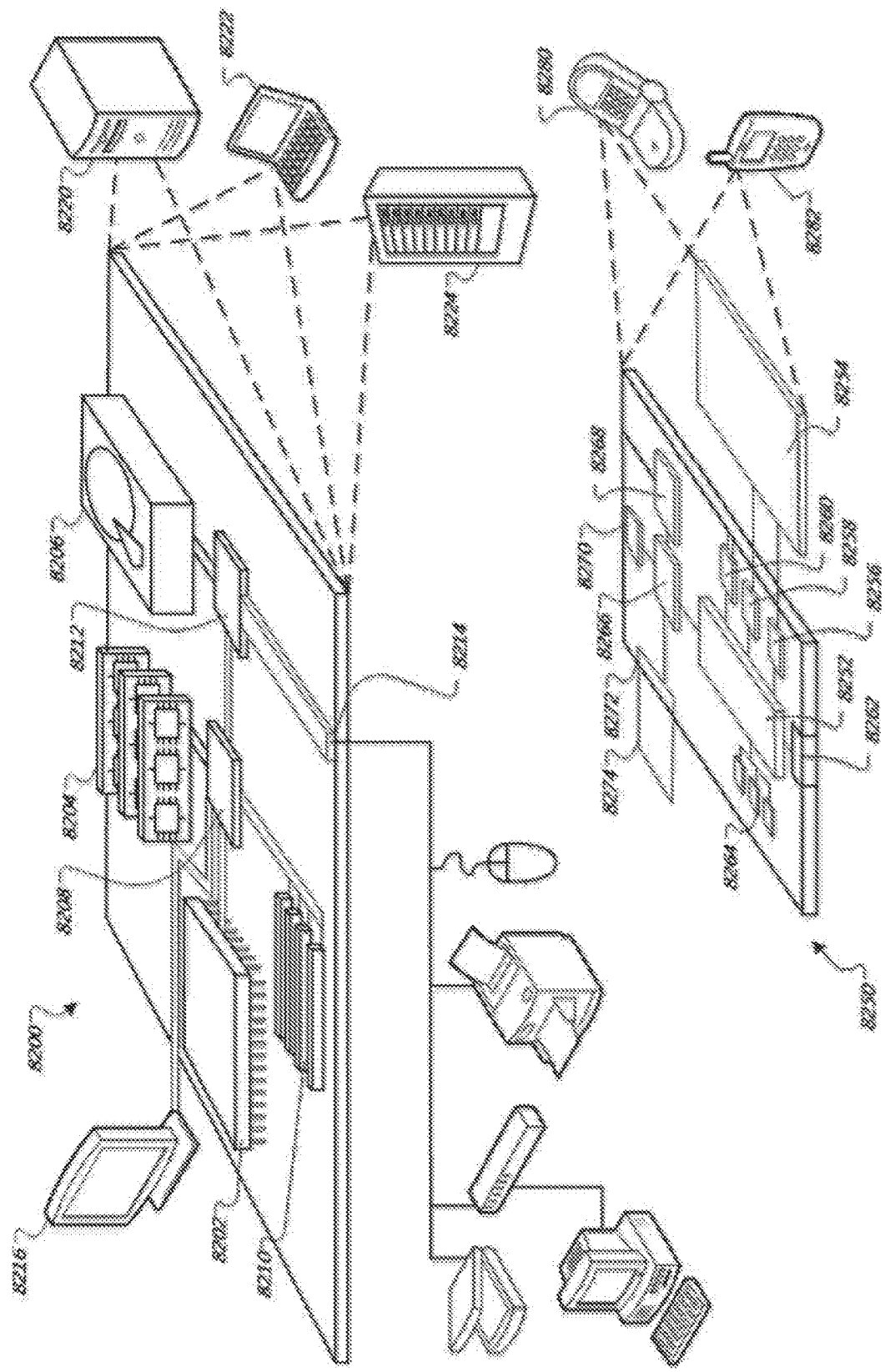
FIG. 82 is a block diagram of computer systems forming part of the surgical tray efficiency system of FIG. 1.

FIG. 82 is a block diagram of computing devices 7500, 7550 that may be used to implement the systems and methods described in this document, as either a client or as a server or plurality of servers. Computing device 7500 is intended to represent various forms of digital computers, such as laptops, desktops, workstations, personal digital assistants, servers, blade servers, mainframes, and other appropriate computers. Computing device 7550 is intended to represent various forms of mobile devices, such as personal digital assistants, cellular telephones, smartphones, and other similar computing devices. In this example, computing device 7550 may represent electronic device 17, while computing device 7500 may represent computing systems that serve as the "cloud" referenced in this disclosure. The components shown here, their connections and relationships, and their functions, are meant to be examples only, and are not meant to limit implementations described and/or claimed in this document.

Computing device 7500 includes a processor 7502, memory 7504, a storage device 7506, a high-speed interface 7508 connecting to memory 7504 and high-speed expansion ports 7510, and a low speed interface 7512 connecting to low speed bus 7514 and storage device 7506. Each of the components 7502, 7504, 7506, 7508, 7510, and 7512, are interconnected using various busses, and may be mounted on a common motherboard or in other manners as appropriate. The processor 7502 can process instructions for execution within the computing device 7500, including instructions stored in the memory 7504 or on the storage device 7506 to display graphical information for a GUI on an external input/output device, such as display 7516 coupled to high-speed interface 7508. In other implementations, multiple processors and/or multiple buses may be used, as appropriate, along with multiple memories and types of memory. Also, multiple computing devices 7500 may be connected, with each device providing portions of the necessary operations (e.g., as a server bank, a group of blade servers, or a multi-processor system).

The memory 7504 stores information within the computing device 7500. In one implementation, the memory 7504 is a volatile memory unit or units. In another implementation, the memory 7504 is a non-volatile memory unit or units. The memory 7504 may also be another form of computer-readable medium, such as a magnetic or optical disk.

The storage device 7506 is capable of providing mass storage for the computing device 7500. In one implementation, the storage device 7506 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 7504, the storage device 7506, or memory on processor 7502.

The high-speed controller 7508 manages bandwidth-intensive operations for the computing device 7500, while the low speed controller 7512 manages lower bandwidth-intensive operations. Such allocation of functions is by way of example only. In one implementation, the high-speed controller 7508 is coupled to memory 7504, display 7516 (e.g., through a graphics processor or accelerator), and to high-speed expansion ports 7510, which may accept various expansion cards (not shown). In the implementation, low-speed controller 7512 is coupled to storage device 7506 and low-speed expansion port 7514. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 7500 may be implemented in a number of different forms, as shown in the figure. For example, it may be implemented as a standard server 7520, or multiple times in a group of such servers. It may also be implemented as part of a rack server system 7524. In addition, it may be implemented in a personal computer such as a laptop computer 7522. Alternatively, components from computing device 7500 may be combined with other components in a mobile device (not shown), such as device 7550. Each of such devices may contain one or more of computing device 7500, 7550, and an entire system may be made up of multiple computing devices 7500, 7550 communicating with each other.

Computing device 7550 includes a processor 7552, memory 7564, an input/output device such as a display 7554, a communication interface 7566, and a transceiver 7568, among other components. The device 7550 may also be provided with a storage device, such as a microdrive or other device, to provide additional storage. Each of the components 7550, 7552, 7564, 7554, 7566, and 7568, are interconnected using various buses, and several of the components may be mounted on a common motherboard or in other manners as appropriate.

The processor 7552 can execute instructions within the computing device 7550, including instructions stored in the memory 7564. The processor may be implemented as a chipset of chips that include separate and multiple analog and digital processors. Additionally, the processor may be implemented using any of a number of architectures. For example, the processor 410 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 7550, such as control of user interfaces, applications run by device 7550, and wireless communication by device 7550.

Processor 7552 may communicate with a user through control interface 7558 and display interface 7556 coupled to a display 7554. The display 7554 may be, for example, a TFT (Thin-Film-Transistor Liquid Crystal Display) display or an OLED (Organic Light Emitting Diode) display, or other appropriate display technology. The display interface 7556 may comprise appropriate circuitry for driving the display 7554 to present graphical and other information to a user. The control interface 7558 may receive commands from a user and convert them for submission to the processor 7552. In addition, an external interface 7562 may be provided in communication with processor 7552, so as to enable near area communication of device 7550 with other devices. External interface 7562 may provide, for example, for wired communication in some implementations, or for wireless communication in other implementations, and multiple interfaces may also be used.

The memory 7564 stores information within the computing device 7550. The memory 7564 can be implemented as one or more of a computer-readable medium or media, a volatile memory unit or units, or a non-volatile memory unit or units. Expansion memory 7574 may also be provided and connected to device 7550 through expansion interface 7572, which may include, for example, a SIMM (Single In Line Memory Module) card interface. Such expansion memory 7574 may provide extra storage space for device 7550, or may also store applications or other information for device 7550. Specifically, expansion memory 7574 may include instructions to carry out or supplement the processes described above, and may include secure information also. Thus, for example, expansion memory 7574 may be provided as a security module for device 7550, and may be programmed with instructions that permit secure use of device 7550. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, cause performance of one or more methods, such as those described above. The information carrier is a computer- or machine-readable medium, such as the memory 7564, expansion memory 7574, or memory on processor 7552 that may be received, for example, over transceiver 7568 or external interface 7562.

Device 7550 may communicate wirelessly through communication interface 7566, which may include digital signal processing circuitry where necessary. Communication interface 7566 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 7568. In addition, short-range communication may occur, such as using a Bluetooth, WiFi, or other such transceiver (not shown). In addition, GPS (Global Positioning System) receiver module 7570 may provide additional navigation- and location-related wireless data to device 7550, which may be used as appropriate by applications running on device 7550.

Device 7550 may also communicate audibly using audio codec 7560, which may receive spoken information from a user and convert it to usable digital information. Audio codec 7560 may likewise generate audible sound for a user, such as through a speaker, e.g., in a handset of device 7550. Such sound may include sound from voice telephone calls, may include recorded sound (e.g., voice messages, music files, etc.) and may also include sound generated by applications operating on device 7550.

The computing device 7550 may be implemented in a number of different forms, some of which are shown in the figure. For example, it may be implemented as a cellular telephone 7580. It may also be implemented as part of a smartphone 7582, personal digital assistant, or other similar mobile device.

Additionally computing device 7500 or 7550 can include Universal Serial Bus (USB) flash drives. The USB flash drives may store operating systems and other applications. The USB flash drives can include input/output components, such as a wireless transmitter or USB connector that may be inserted into a USB port of another computing device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

While the inventive features described herein have been described in terms of a preferred embodiment for achieving the objectives, it will be appreciated by those skilled in the art that variations may be accomplished in view of these teachings without deviating from the spirit or scope of the invention. Furthermore, the various features of the invention have been described using several example embodiments. It should be understood that any feature or combination of features described with regard to a particular example embodiment may be applied to any other example embodiment in any combination without reservation.

I claim:

1. A method for organizing surgical instrumentation using multiple location identifiers that are presented in association with multiple surgical instrument trays, a sterile barrier on which the multiple surgical instrument trays are placed, and a representation by a computing system of the multiple surgical instrument trays, the method comprising:
   depicting, on a user interface of the computing system, the representation of the multiple surgical instrument trays, including multiple graphical elements that each represent a surgical instrument tray of the multiple surgical instrument trays and that are arranged in the user interface according to a planned arrangement of the multiple surgical instrument trays on the sterile barrier, the computing system presenting each of the multiple graphical elements in association with a corresponding location identifier of the multiple location identifiers;
   placing the sterile barrier over one or more surfaces that are configured to hold surgical instrument trays, to form a physical barrier between the one or more surfaces and a sterile field of an operating room in which the one or more surfaces are located, wherein the sterile barrier includes multiple location identifiers that each indicate a location at which a corresponding surgical instrument tray of the multiple surgical instrument trays is to be placed according to the planned arrangement of the multiple surgical instrument trays, wherein each of the multiple surgical instrument trays includes therewith a corresponding location identifier of the multiple location identifiers;
   placing the multiple surgical instrument trays on the sterile barrier according to the planned arrangement of the multiple surgical instrument trays, so that each of the multiple surgical instrument trays is placed at a location on the sterile barrier indicated by a location identifier on the sterile barrier that corresponds to the location identifier included with the respective surgical instrument tray, wherein each of the multiple surgical instrument trays that is placed on the sterile barrier has multiple surgical instruments located thereon;
   receiving, by the computing system, user input that specifies a name for a named surgical instrument; and
   presenting, by the computing system responsive to the computing system receiving the user input that specifies the name for the named surgical instrument, a location identifier of the multiple location identifiers that corresponds to a first surgical instrument tray of the multiple surgical instrument trays on which the named surgical instrument is located.

2. The method of claim 1, wherein the multiple location identifiers comprise letters, numbers, symbols, shapes, colors, and/or words.

3. The method of claim 1, wherein:
   the one or more surfaces comprise a first shelf of a multi-level shelf assembly and a second shelf of the multi-level shelf assembly;
   placing the sterile barrier over the one or more surfaces comprises placing the sterile barrier over the first shelf and the second shelf; and
   placing the multiple surgical instrument trays on the sterile barrier includes placing the first surgical instrument tray on a portion of the sterile barrier that covers the first shelf and placing a second surgical instrument tray of the multiple surgical instrument trays on a portion of the sterile barrier that covers the second shelf.

4. The method of claim 1, wherein each of the multiple surgical instrument trays includes a label, tag, or clip that is affixed thereto and that includes the location identifier for the respective surgical instrument tray of the multiple location identifiers.

5. The method of claim 1, further comprising affixing, to each of the multiple surgical instrument trays, the corresponding location identifier of the multiple locations identifiers.

6. The method of claim 1, wherein:
   each of the multiple graphical elements comprises an image of a surgical instrument tray that includes multiple surgical instruments, such that the representation of the multiple surgical instrument trays includes multiple images of multiple respective surgical instruments trays, each with a different collection of surgical instruments located thereon; and
   the computing system is configured to present, in the user interface upon user selection of a selected graphical element of the multiple graphical elements, names of multiple surgical instruments to be stored on the surgical instrument tray that is represented by the selected graphical element.

7. The method of claim 1, further comprising presenting, by the computing system responsive to the computing system receiving the user input that specifies the name for the named surgical instrument, a location identifier for a second surgical instrument tray of the multiple surgical instrument trays, in addition to presenting the location identifier for the first surgical instrument tray, indicating that a first instance of the named surgical instrument is located on the first surgical instrument tray and that a second instance of the named surgical instrument is located on the second surgical instrument tray.

8. The method of claim 1, wherein:
the sterile barrier includes multiple wires manipulatable to conform the sterile barrier to the one or more surfaces; and
the method further comprises bending the multiple wires around edges of the one or more surfaces to secure respective portions of the sterile barrier to the one or more surfaces.

9. The method of claim 1, further comprising:
receiving, by the computing system, user input that changes an order of the multiple graphical elements that are depicted in the user interface as part of the representation of the multiple surgical instrument trays.

10. The method of claim 1, further comprising:
opening a sterile package that includes the sterile barrier therein while the sterile barrier is folded, wherein placing the sterile barrier on the one or more surfaces includes placing the sterile barrier a portion of on the one or more surfaces while the sterile barrier remains folded; and
unfolding the sterile barrier after the sterile barrier has been placed on the portion of the one or more surfaces.

11. The method of claim 10, wherein the sterile barrier includes multiple visual indicators that indicate how to unfold the sterile barrier.

12. The method of claim 1, wherein the sterile barrier comprises a resilient absorbent material configured to facilitate absorption of liquid.

13. The method of claim 12, wherein the sterile barrier is configured to prevent perforation of the sterile barrier due to contact with surgical instruments.

14. The method of claim 1, wherein:
the user interface of the computing system is configured to present, for each surgical instrument tray of the multiple surgical instrument trays, a corresponding collection of surgical instruments to be located on the respective surgical instrument tray; and
placing, on each of the multiple surgical instrument trays, surgical instruments specified by the computing system in the collection of surgical instruments that corresponds to the respective surgical instrument tray.

15. The method of claim 14, wherein surgical instruments are placed on each of the multiple surgical instrument trays before the multiple surgical instrument trays are placed on the sterile barrier, such that the multiple surgical instrument trays are placed on the sterile barrier while surgical instruments are located on the multiple surgical instrument trays.

16. The method of claim 14, further comprising:
receiving, by the computing system, user input that assigns, to each of the multiple surgical instrument trays, the collection of surgical instruments that corresponds to the respective surgical instrument tray.

17. A method for organizing surgical instrumentation using multiple location identifiers that are presented in association with multiple surgical instrument trays, a sterile barrier on which the multiple surgical instrument trays are placed, and a representation by a computing system of the multiple surgical instrument trays, the method comprising:
depicting, on a user interface of the computing system, the representation of the multiple surgical instrument trays, including multiple graphical elements that each represent a surgical instrument tray of the multiple surgical instrument trays and that are arranged in the user interface according to a planned arrangement of the multiple surgical instrument trays on the sterile barrier, the computing system presenting each of the multiple graphical elements in association with a corresponding location identifier of the multiple location identifiers;
opening a sterile package that includes the sterile barrier therein while the sterile barrier is folded;
placing the sterile barrier, while the sterile barrier is folded, on a multi-level shelf assembly that is configured to hold surgical instrument trays;
unfolding the sterile barrier after the sterile barrier has been placed on the multi-level shelf assembly so that the sterile barrier covers a first shelf of the multi-level shelf assembly and a second shelf of the multi-level shelf assembly, to form a physical barrier between the first and second shelves and a sterile field of an operating room in which the multi-level shelf assembly is located, wherein the sterile barrier includes multiple location identifiers that each indicate a location at which a corresponding surgical instrument tray of the multiple surgical instrument trays is to be placed according to the planned arrangement of the multiple surgical instrument trays, wherein each of the multiple surgical instrument trays includes therewith a corresponding location identifier of the multiple location identifiers; and
placing the multiple surgical instrument trays on the sterile barrier according to the planned arrangement of the multiple surgical instrument trays, so that each of the multiple surgical instrument trays is placed at a location on the sterile barrier indicated by a location identifier on the sterile barrier that corresponds to the location identifier included with the respective surgical instrument tray, including placing a first surgical instrument tray of the multiple surgical instrument trays on a portion of the sterile barrier that covers the first shelf and placing a second surgical instrument tray of the multiple surgical instrument trays on a portion of the sterile barrier that covers the second shelf, wherein each of the multiple surgical instrument trays that is placed on the sterile barrier has multiple surgical instruments located thereon.

* * * * *